United States Patent
Dias et al.

(10) Patent No.: US 11,560,562 B2
(45) Date of Patent: Jan. 24, 2023

(54) LARGE-SCALE SYNTHESIS OF MESSENGER RNA

(71) Applicant: Translate Bio, Inc., Cambridge, MA (US)

(72) Inventors: Anusha Dias, Cambridge, MA (US); Daniel Crawford, Cambridge, MA (US); Frank DeRosa, Cambridge, MA (US); Jonathan Abysalh, Cambridge, MA (US); Michael Heartlein, Cambridge, MA (US)

(73) Assignee: Translate Bio, Inc., Waltham, MA (US)

(*) Notice: Subject to any disclaimer, the term of this patent is extended or adjusted under 35 U.S.C. 154(b) by 352 days.

(21) Appl. No.: 15/907,163

(22) Filed: Feb. 27, 2018

(65) Prior Publication Data
US 2018/0258423 A1    Sep. 13, 2018

Related U.S. Application Data

(60) Provisional application No. 62/464,043, filed on Feb. 27, 2017.

(51) Int. Cl.
| | |
|---|---|
| C12N 15/10 | (2006.01) |
| C12P 19/34 | (2006.01) |
| C12N 9/12 | (2006.01) |
| G01N 27/447 | (2006.01) |

(52) U.S. Cl.
CPC ....... C12N 15/1096 (2013.01); C12N 9/1247 (2013.01); C12N 15/1068 (2013.01); C12P 19/34 (2013.01); C12Y 207/07006 (2013.01); G01N 27/44778 (2013.01)

(58) Field of Classification Search
CPC .............. C12N 15/1096; C12N 9/1247; C12N 15/1068; C12N 15/10; C12P 19/34; C12Y 207/07006; C12Q 2521/119
See application file for complete search history.

(56) References Cited

U.S. PATENT DOCUMENTS

| | | | |
|---|---|---|---|
| 2016/0326575 A1 | 10/2016 | Von Der Mulbe et al. | |
| 2018/0161451 A1 | 1/2018 | Fotin-Mleczek et al. | |

FOREIGN PATENT DOCUMENTS

| | | | | |
|---|---|---|---|---|
| WO | 2012/170930 A1 | 12/2012 | | |
| WO | WO-2015188933 A1 * | 12/2015 | ............ | C12M 23/44 |
| WO | 2016/149508 A1 | 9/2016 | | |
| WO | WO-2016180430 A1 * | 11/2016 | .............. | C12P 19/34 |

OTHER PUBLICATIONS

Krieg, P.A. and Melton, D.A. In Vitro RNA Synthesis with SP6 RNA Polymerase. Methods in Enzymology 1987; 155: 397-415 (Year: 1987).*
Thurston et al. Electrophoresis of RNA Denatured with Glyoxal or Formaldehyde. Methods in Molecular Biology 1988; 4: 1-11 (Year: 1988).*
Yang, T.H. and Chang, P.L. Determination of RNA degradation by capillary electrophoresis with cyan light-emitted diode-induced fluorescence. Journal of Chromatography A 2012; 1239: 78-84 (Year: 2012).*
Skeidsvoll, J. and Ueland, P.M. Analysis of RNA by capillary electrophoresis. Electrophoresis 1996; 17: 1512-1517 (Year: 1996).*
He et al. Rapid Mutagensis and Purification of Phage RNA Polymerases. Protein Expression and Purification 1997; 9: 142-151 (Year: 1997).*
Gurevich et al. Preparative in vitro mRNA Synthesis Using SP6 and T7 RNA Polymerases. Analytical Biochemistry 1991; 195: 207-213 (Year: 1991).*
Pascolo, S. Vaccination with messenger RNA. Methods in Molecular Medicine 2006; 127: 23-40 (Year: 2006).*
Brito et al. Self-Amplifying mRNA Vaccines. Advances in Genetics 2015; 89: 179-233 (Year: 2015).*
Anonymous, "RiboMAX™ Large Scale RNA Production Systems-SP6 and T7", pp. 1-14 (2007) Retrieved from the Internet: https://france.promega.com/-/media/files/resources/protocols/technical-bulletins/0/ribomax-large-scale-rna-production-systemssp6-and-t7-protocol.pdf.
Gonzalez-Perez et al., "Scaling up in vitro transcription synthesis of RNA standards for competitive quantitative RT-PCR: Looking for bigger yields", Anal Biochem., 385(1): 179-81 (2009).
Robinson et al., "Lipid Nanoparticle-Delivered Chemically Modified mRNA Restores Chloride Secretion in Cystic Fibrosis", Molecular Therapy, 26(8): 1-13 (2018).
Yoshioka et al., "Efficient generation of human iPSCs by a synthetic self-replicative RNA", Cell Stem Cell, 13(2): 246-54 (2013).
S. Lee et al: "Tiny abortive initiation transcripts exert antitermination activity on an RNA hairpin-dependent intrinsic terminator", Nucleic Acids Research, vol. 38, No. 18, Oct. 1, 2010, pp. 6045-6053, XP055742462, ISSN: 0305-1048, DOI: 10.1093/nar/gkq450.

* cited by examiner

*Primary Examiner* — Angela M. Bertagna

(74) *Attorney, Agent, or Firm* — Proskauer Rose LLP; Fangli Chen; Nicholas C. Prairie

(57) ABSTRACT

The present invention provides methods for large-scale production of a composition enriched for full-length mRNA molecules using an SP6 RNA polymerase and compositions produced using such methods and uses thereof.

18 Claims, 32 Drawing Sheets
Specification includes a Sequence Listing.

hRS1 mRNA

SEQUENCE LISTING

<160> NUMBER OF SEQ ID NOS: 15

<210> SEQ ID NO 1
<211> LENGTH: 874
<212> TYPE: PRT
<213> ORGANISM: Bacteriophage SP6

<400> SEQUENCE: 1

Met Gln Asp Leu His Ala Ile Gln Leu Gln Leu Glu Glu Glu Met Phe
1               5                   10                  15

```
Asn Gly Gly Ile Arg Arg Phe Glu Ala Asp Gln Gln Arg Gln Ile Ala
             20                  25                  30
Ala Gly Ser Glu Ser Asp Thr Ala Trp Asn Arg Arg Leu Leu Ser Glu
         35                  40                  45
Leu Ile Ala Pro Met Ala Glu Gly Ile Gln Ala Tyr Lys Glu Glu Tyr
 50                  55                  60
Glu Gly Lys Lys Gly Arg Ala Pro Arg Ala Leu Ala Phe Leu Gln Cys
65                  70                  75                  80
Val Glu Asn Glu Val Ala Ala Tyr Ile Thr Met Lys Val Val Met Asp
             85                  90                  95
Met Leu Asn Thr Asp Ala Thr Leu Gln Ala Ile Ala Met Ser Val Ala
            100                 105                 110
Glu Arg Ile Glu Asp Gln Val Arg Phe Ser Lys Leu Glu Gly His Ala
        115                 120                 125
Ala Lys Tyr Phe Glu Lys Val Lys Lys Ser Leu Lys Ala Ser Arg Thr
        130                 135                 140
Lys Ser Tyr Arg His Ala His Asn Val Ala Val Ala Glu Lys Ser
145                 150                 155                 160
Val Ala Glu Lys Asp Ala Asp Phe Asp Arg Trp Glu Ala Trp Pro Lys
                165                 170                 175
Glu Thr Gln Leu Gln Ile Gly Thr Thr Leu Leu Glu Ile Leu Glu Gly
            180                 185                 190
Ser Val Phe Tyr Asn Gly Glu Pro Val Phe Met Arg Ala Met Arg Thr
        195                 200                 205
Tyr Gly Gly Lys Thr Ile Tyr Tyr Leu Gln Thr Ser Glu Ser Val Gly
210                 215                 220
Gln Trp Ile Ser Ala Phe Lys Glu His Val Ala Gln Leu Ser Pro Ala
225                 230                 235                 240
Tyr Ala Pro Cys Val Ile Pro Pro Arg Pro Arg Thr Pro Phe Asn
                245                 250                 255
Gly Gly Phe His Thr Glu Lys Val Ala Ser Arg Ile Arg Leu Val Lys
            260                 265                 270
Gly Asn Arg Glu His Val Arg Lys Leu Thr Gln Lys Gln Met Pro Lys
        275                 280                 285
Val Tyr Lys Ala Ile Asn Ala Leu Gln Asn Thr Gln Trp Gln Ile Asn
        290                 295                 300
Lys Asp Val Leu Ala Val Ile Glu Glu Val Ile Arg Leu Asp Leu Gly
305                 310                 315                 320
Tyr Gly Val Pro Ser Phe Lys Pro Leu Ile Asp Lys Glu Asn Lys Pro
                325                 330                 335
Ala Asn Pro Val Pro Val Glu Phe Gln His Leu Arg Gly Arg Glu Leu
            340                 345                 350
Lys Glu Met Leu Ser Pro Glu Gln Trp Gln Gln Phe Ile Asn Trp Lys
        355                 360                 365
Gly Glu Cys Ala Arg Leu Tyr Thr Ala Glu Thr Lys Arg Gly Ser Lys
        370                 375                 380
Ser Ala Ala Val Val Arg Met Val Gly Gln Ala Arg Lys Tyr Ser Ala
385                 390                 395                 400
Phe Glu Ser Ile Tyr Phe Val Tyr Ala Met Asp Ser Arg Ser Arg Val
                405                 410                 415
Tyr Val Gln Ser Ser Thr Leu Ser Pro Gln Ser Asn Asp Leu Gly Lys
            420                 425                 430
Ala Leu Leu Arg Phe Thr Glu Gly Arg Pro Val Asn Gly Val Glu Ala
```

```
            435                 440                 445
Leu Lys Trp Phe Cys Ile Asn Gly Ala Asn Leu Trp Gly Trp Asp Lys
450                 455                 460

Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                    485                 490                 495

Ala Lys Ala Asp Ala Pro Tyr Glu Phe Leu Ala Trp Cys Phe Glu Tyr
                500                 505                 510

Ala Gln Tyr Leu Asp Leu Val Asp Glu Gly Arg Ala Asp Glu Phe Arg
            515                 520                 525

Thr His Leu Pro Val His Gln Asp Gly Ser Cys Ser Gly Ile Gln His
        530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                    565                 570                 575

Val Ile Lys Lys Asn Ala Leu Tyr Met Asp Ala Asp Asp Ala Thr Thr
                580                 585                 590

Phe Thr Ser Gly Ser Val Thr Leu Ser Gly Thr Glu Leu Arg Ala Met
            595                 600                 605

Ala Ser Ala Trp Asp Ser Ile Gly Ile Thr Arg Ser Leu Thr Lys Lys
        610                 615                 620

Pro Val Met Thr Leu Pro Tyr Gly Ser Thr Arg Leu Thr Cys Arg Glu
625                 630                 635                 640

Ser Val Ile Asp Tyr Ile Val Asp Leu Glu Glu Lys Glu Ala Gln Lys
                    645                 650                 655

Ala Val Ala Glu Gly Arg Thr Ala Asn Lys Val His Pro Phe Glu Asp
                660                 665                 670

Asp Arg Gln Asp Tyr Leu Thr Pro Gly Ala Ala Tyr Asn Tyr Met Thr
            675                 680                 685

Ala Leu Ile Trp Pro Ser Ile Ser Glu Val Val Lys Ala Pro Ile Val
        690                 695                 700

Ala Met Lys Met Ile Arg Gln Leu Ala Arg Phe Ala Ala Lys Arg Asn
705                 710                 715                 720

Glu Gly Leu Met Tyr Thr Leu Pro Thr Gly Phe Ile Leu Glu Gln Lys
                    725                 730                 735

Ile Met Ala Thr Glu Met Leu Arg Val Arg Thr Cys Leu Met Gly Asp
                740                 745                 750

Ile Lys Met Ser Leu Gln Val Glu Thr Asp Ile Val Asp Glu Ala Ala
            755                 760                 765

Met Met Gly Ala Ala Pro Asn Phe Val His Gly His Asp Ala Ser
        770                 775                 780

His Leu Ile Leu Thr Val Cys Glu Leu Val Asp Lys Gly Val Thr Ser
785                 790                 795                 800

Ile Ala Val Ile His Asp Ser Phe Gly Thr His Ala Asp Asn Thr Leu
                    805                 810                 815

Thr Leu Arg Val Ala Leu Lys Gly Gln Met Val Ala Met Tyr Ile Asp
                820                 825                 830

Gly Asn Ala Leu Gln Lys Leu Leu Glu Glu His Glu Val Arg Trp Met
            835                 840                 845

Val Asp Thr Gly Ile Glu Val Pro Glu Gln Gly Glu Phe Asp Leu Asn
        850                 855                 860
```

```
Glu Ile Met Asp Ser Glu Tyr Val Phe Ala
865                 870
```

<210> SEQ ID NO 2
<211> LENGTH: 2625
<212> TYPE: DNA
<213> ORGANISM: Bacteriophage SP6

<400> SEQUENCE: 2

| | | | | | |
|---|---|---|---|---|---|
| atgcaagatt | tacacgctat | ccagcttcaa | ttagaagaag | agatgtttaa | tggtggcatt | 60 |
| cgtcgcttcg | aagcagatca | acaacgccag | attgcagcag | gtagcgagag | cgacacagca | 120 |
| tggaaccgcc | gcctgttgtc | agaacttatt | gcacctatgg | ctgaaggcat | tcaggcttat | 180 |
| aaagaagagt | acgaaggtaa | gaaggtcgt | gcacctcgcg | cattggcttt | cttacaatgt | 240 |
| gtagaaaatg | aagttgcagc | atacatcact | atgaaagttg | ttatggatat | gctgaatacg | 300 |
| gatgctaccc | ttcaggctat | tgcaatgagt | gtagcagaac | gcattgaaga | ccaagtgcgc | 360 |
| ttttctaagc | tagaaggtca | cgccgctaaa | tactttgaga | aggttaagaa | gtcactcaag | 420 |
| gctagccgta | ctaagtcata | tcgtcacgct | cataacgtag | ctgtagttgc | tgaaaaatca | 480 |
| gttgcagaaa | aggacgcgga | cttttgaccgt | tgggaggcgt | ggccaaaaga | aactcaattg | 540 |
| cagattggta | ctaccttgct | tgaaatctta | gaaggtagcg | ttttctataa | tggtgaacct | 600 |
| gtatttatgc | gtgctatgcg | cacttatggc | ggaaagacta | tttactactt | acaaacttct | 660 |
| gaaagtgtag | gccagtggat | tagcgcattc | aaagagcacg | tagcgcaatt | aagcccagct | 720 |
| tatgcccctt | gcgtaatccc | tcctcgtcct | tggagaactc | catttaatgg | agggttccat | 780 |
| actgagaagg | tagctagccg | tatccgtctt | gtaaaggta | accgtgagca | tgtacgcaag | 840 |
| ttgactcaaa | agcaaatgcc | aaaggtttat | aaggctatca | acgcattaca | aaatacacaa | 900 |
| tggcaaatca | caaggatgt | attagcagtt | attgaagaag | taatccgctt | agaccttggt | 960 |
| tatggtgtac | cttccttcaa | gccactgatt | gacaaggaga | caagccagc | taaccccggta | 1020 |
| cctgttgaat | ccaacacct | gcgcggtcgt | gaactgaaag | agatgctatc | acctgagcag | 1080 |
| tggcaacaat | tcattaactg | gaaaggcgaa | tgcgcgcgcc | tatataccgc | agaaactaag | 1140 |
| cgcggttcaa | agtccgccgc | cgttgttcgc | atggtaggac | aggcccgtaa | atatagcgcc | 1200 |
| tttgaatcca | tttacttcgt | gtacgcaatg | gatagccgca | gccgtgtcta | tgtgcaatct | 1260 |
| agcacgctct | ctccgcagtc | taacgactta | ggtaaggcat | tactccgctt | taccgaggga | 1320 |
| cgccctgtga | tggcgtaga | agcgcttaaa | tggttctgca | tcaatggtgc | taaccttggg | 1380 |
| ggatgggaca | agaaaacttt | tgatgtgcgc | gtgtctaacg | tattagatga | ggaattccaa | 1440 |
| gatatgtgtc | gagacatcgc | cgcagaccct | ctcacattca | cccaatgggc | taaagctgat | 1500 |
| gcaccttatg | aattcctcgc | ttggtgcttt | gagtatgctc | aataccttga | tttggtggat | 1560 |
| gaaggaaggg | ccgacgaatt | ccgcactcac | ctaccagtac | atcaggacgg | tctttgtca | 1620 |
| ggcattcagc | actatagtgc | tatgcttcgc | gacgaagtag | gggccaaagc | tgttaacctg | 1680 |
| aaaccctccg | atgcaccgca | ggatatctat | ggggcggtgg | cgcaagtggt | tatcaagaag | 1740 |
| aatgcgctat | atatggatgc | ggacgatgca | accacgttta | cttctggtag | cgtcacgctg | 1800 |
| tccggtacag | aactgcgagc | aatggctagc | gcatgggata | gtattggtat | acccgtagc | 1860 |
| ttaaccaaaa | agcccgtgat | gaccttgcca | tatggttcta | ctcgcttaac | ttgccgtgaa | 1920 |
| tctgtgattg | attacatcgt | agacttagag | gaaaaagagg | cgcagaaggc | agtagcagaa | 1980 |
| gggcggacgg | caaacaaggt | acatccttttt | gaagacgatc | gtcaagatta | cttgactccg | 2040 |

```
ggcgcagctt acaactacat gacggcacta atctggcctt ctatttctga agtagttaag    2100
gcaccgatag tagctatgaa gatgatacgc cagcttgcac gctttgcagc gaaacgtaat    2160
gaaggcctga tgtacaccct gcctactggc ttcatcttag aacagaagat catggcaacc    2220
gagatgctac gcgtgcgtac ctgtctgatg ggtgatatca agatgtccct tcaggttgaa    2280
acggatatcg tagatgaagc cgctatgatg ggagcagcag cacctaattt cgtacacggt    2340
catgacgcaa gtcaccttat ccttaccgta tgtgaattgg tagacaaggg cgtaactagt    2400
atcgctgtaa tccacgactc ttttggtact catgcagaca acaccctcac tcttagagtg    2460
gcacttaaag ggcagatggt tgcaatgtat attgatggta atgcgcttca gaaactactg    2520
gaggagcatg aagtgcgctg gatggttgat acaggtatcg aagtacctga gcaaggggag    2580
ttcgacctta acgaaatcat ggattctgaa tacgtatttg cctaa                   2625

<210> SEQ ID NO 3
<211> LENGTH: 18
<212> TYPE: DNA
<213> ORGANISM: Bacteriophage SP6

<400> SEQUENCE: 3
atttaggtga cactatag                                                  18

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
atttagggga cactatagaa gag                                            23

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
atttagggga cactatagaa gg                                             22

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
atttagggga cactatagaa ggg                                            23

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
atttaggtga cactatagaa                                                20
```

```
<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
atttaggtga cactatagaa ga                                              22

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
atttaggtga cactatagaa gag                                             23

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
atttaggtga cactatagaa gg                                              22

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 11
atttaggtga cactatagaa ggg                                             23

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: n = any nucleotide
<220> FEATURE:
<221> NAME/KEY: misc_feature
<222> LOCATION: (22)..(22)
<223> OTHER INFORMATION: n is a, c, g, or t

<400> SEQUENCE: 12
atttaggtga cactatagaa gng                                             23

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
catacgattt aggtgacact atag                                            24
```

```
<210> SEQ ID NO 14
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 14
taatacgact cactatagga cagatcg                                        27

<210> SEQ ID NO 15
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 15
cgatctgtcc tatagtgagt cgtatta                                        27
```

LARGE-SCALE SYNTHESIS OF MESSENGER RNA

RELATED APPLICATIONS

This application claims priority to U.S. Provisional Application Ser. No. 62/464,043, filed on Feb. 27, 2017, the entire disclosure of which is hereby incorporated by reference.

SEQUENCE LISTING

The present specification makes reference to a Sequence Listing (submitted electronically as a .txt file named MRT-2000 US_ST25 on 11/05/2020). The .txt file was generated on 10/20/2020 and is 13,940 bytes in size. The entire contents of the sequence are herein incorporated by reference.

BACKGROUND OF THE INVENTION mRNA therapy becomes increasingly important for treating various diseases. During in vitro synthesis of mRNA, RNA Polymerase (RNAP) recognizes its cognate promoter leading to the local melting of a DNA double strand template to form the transcriptional "initiation complex". Transcription during this stage is characterized by the repetitive synthesis and release of two to six nucleotides called "abortive cycling", which was known to be common to all RNAPs. Even at saturating nucleotide concentrations, abortive transcripts are present in reactions in vitro, although their lengths differ among different RNAPs. After the synthesis of about eight to twelve nucleotides, the polymerase undergoes a major structural rearrangement and dissociates from the promoter (promoter clearance) to enter into the processive synthesis of RNA, forming the "elongation complex" until transcription termination (FIG. 1). Since the initiation complex is unstable, when compared to the elongation complex, abortive transcripts are repeatedly released until the polymerase engages in productive transcription, which produces full-length transcripts. It was reported that both T7 and SP6 RNA polymerases generate abortive transcripts during in vitro synthesis of mRNA. (Nam et al. 1988, The Journal of Biological Chemistry, 263: 34, pp 18123-18127; Lee et al., Nucleic Acids Research 2010, 1-9). The presence of such abortive transcripts in a therapeutic composition based on in vitro synthesized mRNA could impact its safety and efficacy.

Accordingly, a need exists for a large scale synthesis method that produces mRNA enriched for full-length mRNA transcripts.

SUMMARY OF THE INVENTION

The present invention addresses this need by providing a large-scale in vitro synthesis method that produces mRNA significantly enriched with full-length transcripts. The invention is based in part upon the surprising discovery that, despite the common beliefs, SP6 RNA Polymerase (RNAP) synthesizes mRNA with significantly reduced abortive transcripts as compared to T7 RNA polymerase. As described in more detail below, including the Examples section, mRNA molecules synthesized by an SP6 RNA polymerase are significantly more uniform and homogeneous enriched with full-length mRNA molecules as compared to the mRNA molecules synthesized by a T7 RNA polymerase which have a more heterogeneous profile with lower molecular weight pre-aborted transcripts present, when characterized by Glyoxal agarose gel electrophoresis or capillary electrophoresis after capping and tailing. This data demonstrates that the mRNA synthesized by SP6 RNA polymerase has a significantly higher quality, as compared to that synthesized by T7 RNA polymerase. Indeed, mRNA synthesized by an SP6 RNA polymerase resulted in more efficient translation once transfected into cells. Specifically, SP6-derived mRNA resulted in higher expression and activity level of the protein encoded by the mRNA as compared to the same amount of T7 derived mRNA. These unique and advantageous properties of SP6 RNA polymerase were not appreciated prior to the present invention and are truly unexpected especially because the prior art specifically teaches that both T7 and SP6 RNA polymerases generate abortive transcripts. Based on this unexpected discovery of SP6 RNA polymerase, the present inventors have successfully developed a large-scale production method to synthesize mRNA molecules that are enriched with full-length transcripts. As shown below, the large-scale mRNA production process provided by the present invention can produce at least 100 mg of mRNA (e.g., at least 500 mg, 1 kg, 10 kg, 50 kg, 100 kg, or higher amounts of mRNA) in a single batch with undetectable level of abortive transcripts. Thus, the present invention significantly improves large-scale commercial production of high quality mRNA for therapeutic use.

An aspect of the present invention is a method for large-scale production of a composition enriched for full-length mRNA molecules. The method includes a step of synthesizing in vitro mRNA using an SP6 RNA polymerase. In some embodiments, at least 80% of the synthesized mRNA molecules are full-length. In some embodiments, at least 100 mg of mRNA is synthesized in a single batch.

In some embodiments, at least 81%, 82%, 83%, 84%, 85%, 86%, 87%, 88%, 89%, 90%, 91%, 92%, 93%, 94%, 95%, 96%, 97%, 98%, 99%, 99.5%, or 99.9% of the synthesized mRNA molecules are full-length. In some embodiments, the synthesized mRNA molecules are substantially full-length.

In some embodiments, a composition includes less than 20%, 19%, 18%, 17%, 16%, 15%, 14%, 13%, 12%, 11%, 10%, 9%, 8%, 7%, 6%, 5%, 4%, 3%, 2%, 1%, 0.5%, or 0.1% of abortive transcripts. In some embodiments, a composition according to the present invention is substantially free of abortive transcripts.

In some embodiments, the full-length or abortive transcripts of mRNA are detected by gel electrophoresis (e.g., agarose gel electrophoresis) where the mRNA is denatured by Glyoxal before agarose gel electrophoresis ("Glyoxal agarose gel electrophoresis"). The mRNA synthesized according to the method of the invention contains undetectable amount of abortive transcripts on Glyoxal agarose gel electrophoresis.

In some embodiments, the full-length or abortive transcripts of mRNA are detected by capillary electrophoresis, e.g., capillary electrophoresis coupled with a fluorescence-based detection or capillary electrophoresis coupled with UV absorption spectroscopy detection. When detection is by capillary electrophoresis coupled with fluorescence based detection or by capillary electrophoresis coupled with UV absorption spectroscopy, the relative amount of full-length or abortive transcripts of synthesized mRNA is determined by the relative peak areas corresponding to the full-length or abortive transcripts.

Full-length or abortive transcripts of mRNA may be detected prior to capping and/or tailing the synthesized mRNA.

In some embodiments, the method further includes steps of capping and/or tailing the synthesized mRNA. The full-length or abortive transcripts of mRNA may be detected after capping and/or tailing of the synthesized mRNA.

In some embodiments, the full-length mRNA molecule is at least 100 bases, 200 bases, 300 bases, 400 bases, 500 bases, 600 bases, 700 bases, 800 bases, 900 bases, 1 kb, 1.5 kb, 2 kb, 2.5 kb, 3 kb, 3.5 kb, 4 kb, 4.5 kb, or 5 kb in length.

In some embodiments, at least 200 mg, 300 mg, 400 mg, 500 mg, 600 mg, 700 mg, 800 mg, 900 mg, 1 g, 5 g, 10 g, 25 g, 50 g, 75 g, 100 g, 150 g, 200 g, 250 g, 500 g, 750 g, 1 kg, 5 kg, 10 kg, 50 kg, 100 kg, 1000 kg, or more of mRNA is synthesized in a single batch.

In some embodiments, the method further includes a step of purifying synthesized mRNA to remove abortive transcripts or the method does not include a step of specifically removing abortive transcripts.

In some embodiments, the SP6 RNA polymerase is a naturally occurring SP6 RNA polymerase or the SP6 RNA polymerase is a recombinant SP6 RNA polymerase. The recombinant SP6 RNA polymerase may include a tag, e.g., a his-tag.

In some embodiments, the mRNA is synthesized by the SP6 RNA polymerase based on a DNA template, e.g., a DNA template including an SP6 promoter operably linked to a DNA sequence encoding the mRNA sequence to be synthesized. The DNA sequence may be optimized, e.g., to reduce the chance of a hairpin structure forming in the synthesized mRNA.

In some embodiments, the mRNA is synthesized in a reaction mixture comprising NTPs at a concentration ranging from 1-10 mM (e.g., 1-8 mM, 1-6 mM, 1-5 mM, 2-10 mM, 2-8 mM, 2-6 mM, and 4-5 mM) for each NTP, the DNA template at a concentration ranging from 0.01-0.5 mg/ml (e.g., 0.05-0.4 mg/ml, 0.05-0.3 mg/ml, 0.05-0.2 mg/ml, and 0.05-0.15 mg/ml), and the SP6 RNA polymerase at a concentration ranging from 0.01-0.1 mg/ml (e.g., 0.02-0.08 mg/ml, and 0.04-0.06 mg/ml). In some embodiments, the reaction mixture comprises NTPs at a concentration of 5 mM, the DNA template at a concentration of 0.1 mg/ml, and the SP6 RNA polymerase at a concentration of 0.05 mg/ml.

In some embodiments, the mRNA is synthesized at a temperature ranging from 37-42° C. (e.g., about 37° C., 38° C., 39° C., 40° C., 41° C., and 42° C.).

In some embodiments, the NTPs suitable for the present invention are naturally-occurring NTPs. In other embodiments, the NTPs suitable for the present invention comprise modified NTPs.

An aspect of the present invention is a method for large-scale production of a composition enriched for full-length mRNA comprising synthesizing in vitro mRNA using an SP6 RNA polymerase. The method is for the production of at least 1 kg of mRNA, which is synthesized in a single batch and the composition contains undetectable amount of abortive transcripts, after capping and tailing, by Glyoxal agarose gel electrophoresis or capillary electrophoresis.

Another aspect of the present invention is a composition comprising mRNA synthesized according to the method described in any one of its embodiments or any combination of its embodiments.

In some embodiments, the mRNA of the composition is associated with a liposome, e.g., a liposome including one or more of cationic lipids, non-cationic lipids, sterol-based lipids, and PEG-modified lipids.

In some embodiments, the mRNA of the composition is associated with a polymer.

Yet another aspect of the present invention is a method of delivering mRNA for in vivo protein production. The method includes a step of administering a composition of the prior aspect or any one of its embodiments or any combination of its embodiments.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the Drawings and the following Detailed Description, including the Examples, and the claims.

BRIEF DESCRIPTION OF THE DRAWINGS

The above and further features will be more clearly appreciated from the following detailed description when taken in conjunction with the accompanying drawings. The drawings however are for illustration purposes only; not for limitation.

Figure 5:
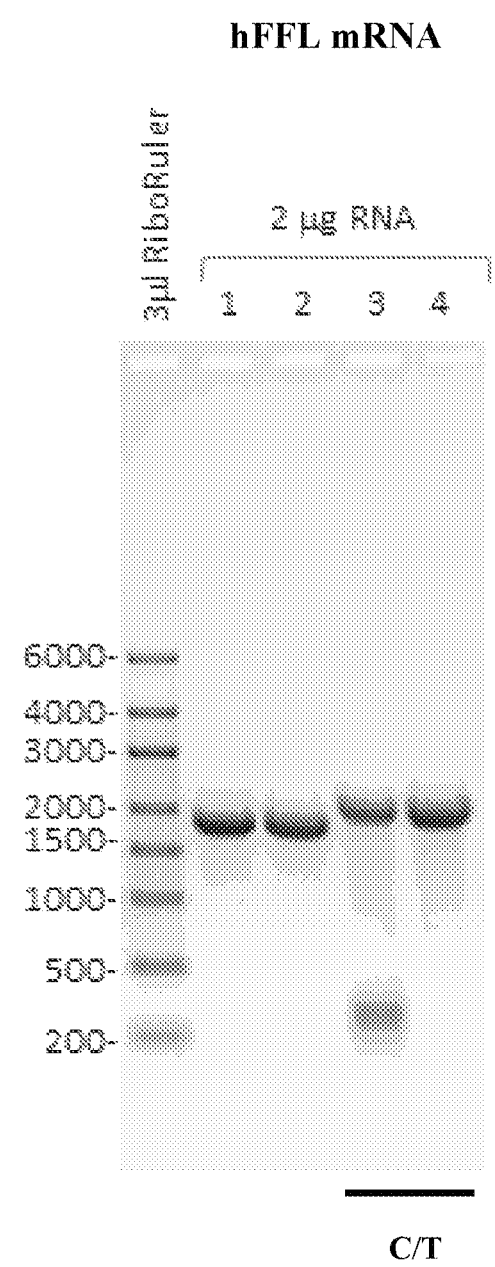

FIG. 5 is a digital image of an agarose gel of Firefly Luciferase (FFL) mRNA transcribed with SP6 versus T7 polymerase. FFL mRNA was transcribed with SP6 or T7 polymerase and the capped and tailed product was run on a 1% agarose gel in Glyoxal gel loading dye for 60 minutes. Lanes: lane 1, FFL T7 IVT; lane 2, FFL SP6 IVT; lane 3, FFL T7 transcript after C/T; and lane 4, FFL T7 transcript after C/T.

Figure 6:
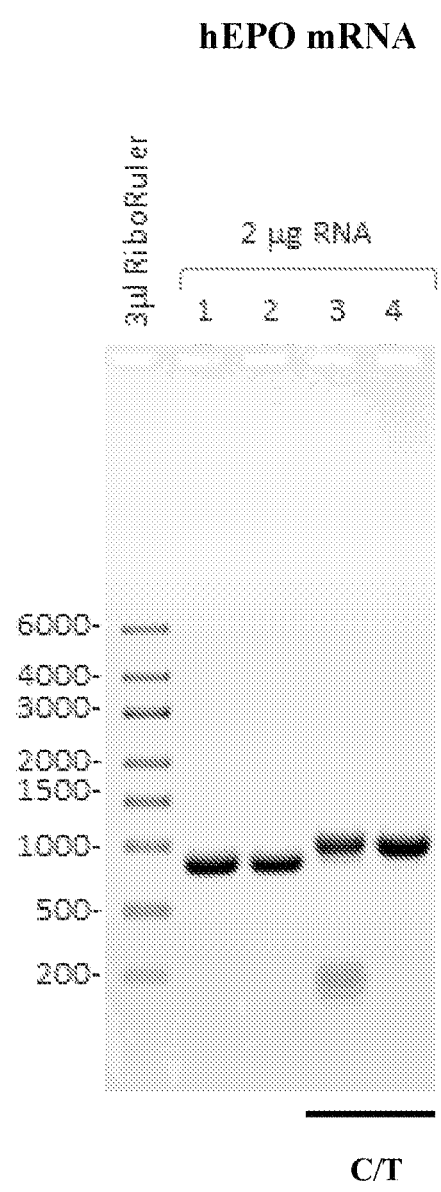

FIG. 6 is a digital image of an agarose gel of human erythropoietin (EPO) mRNA transcribed with SP6 versus T7 polymerase. EPO RNA was transcribed with SP6 or T7 polymerase and the capped and tailed product was run on a 1% agarose gel in Glyoxal gel loading dye for 60 minutes. Lanes: lane 1, EPO T7 IVT; lane 2, EPO SP6 IVT; lane 3, EPO T7 transcript after C/T; and lane 4, EPO T7 transcript after C/T.

Figure 7:
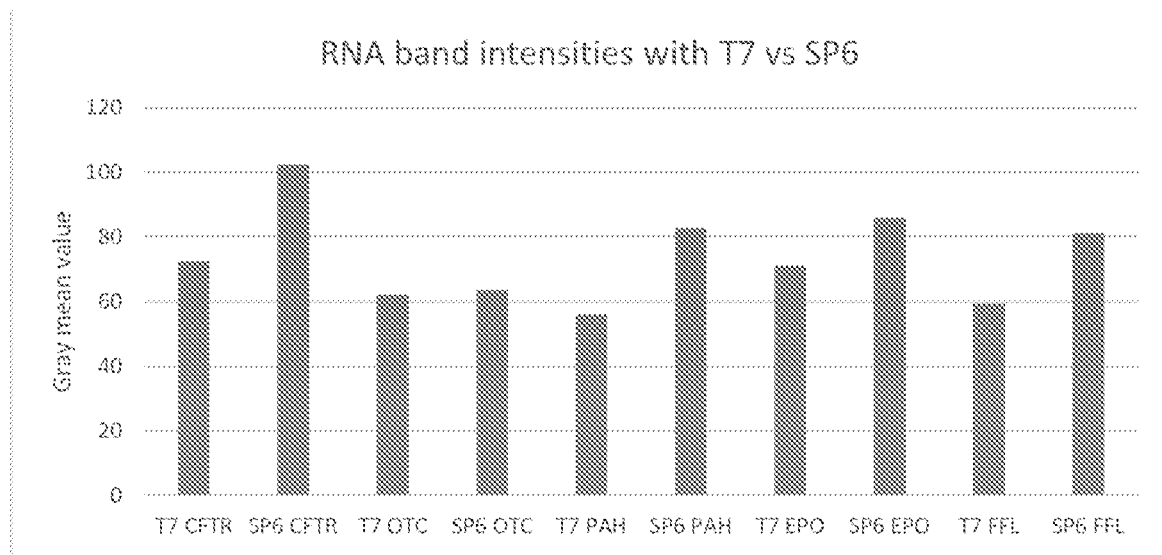

FIG. 7 depicts a graph of densitometric scan values of the full-length mRNA bands from T7-derived and SP6-derived mRNA samples.

Figure 8:
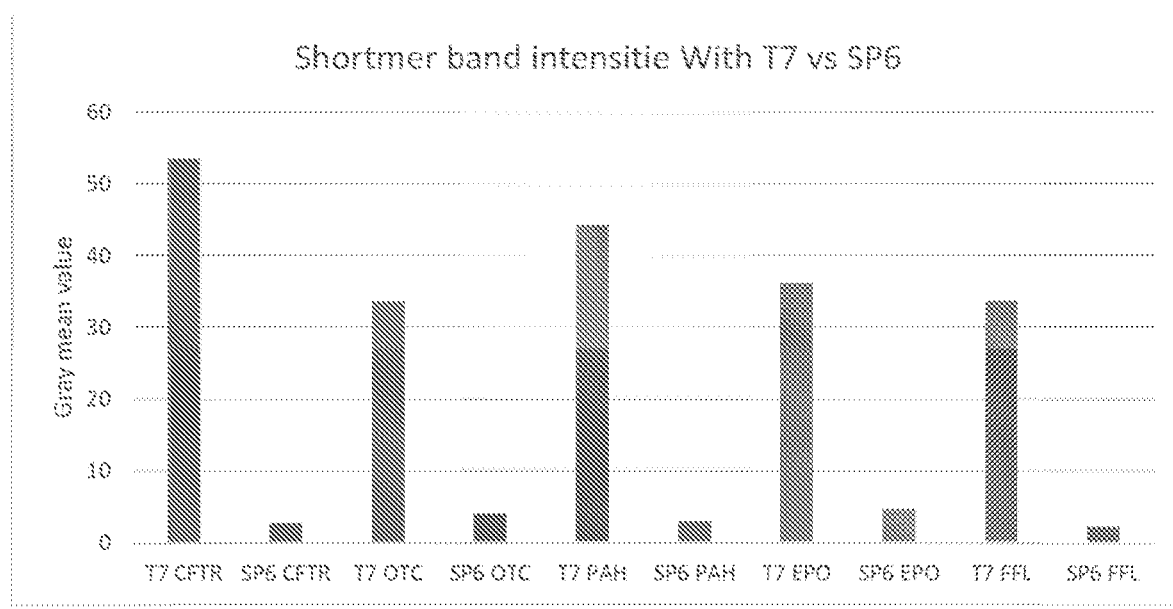

FIG. 8 depicts a graph of densitometric scan values of the shortmer bands from T7-derived and SP6-derived mRNA samples.

Figure 9:
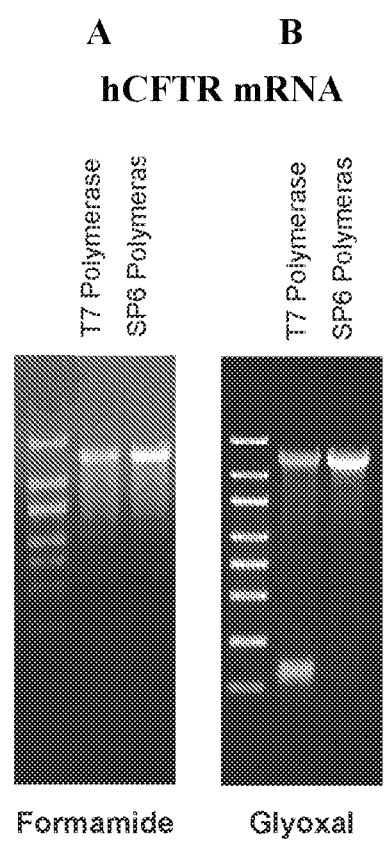

FIG. 9A-B are digital images of agarose gel of human CFTR mRNA transcribed with SP6 versus T7 polymerase run on a 1% agarose gel in Formamide gel loading dye (FIG. 9A) and on a 1% agarose gel in Glyoxal gel loading dye (FIG. 9B) for 60 minutes. Lanes (FIGS. 9A and 9B): lane 1, CFTR mRNA transcribed with SP6, after C/T; lane 2, CFTR mRNA transcribed with T7, after C/T.

Figure 10:
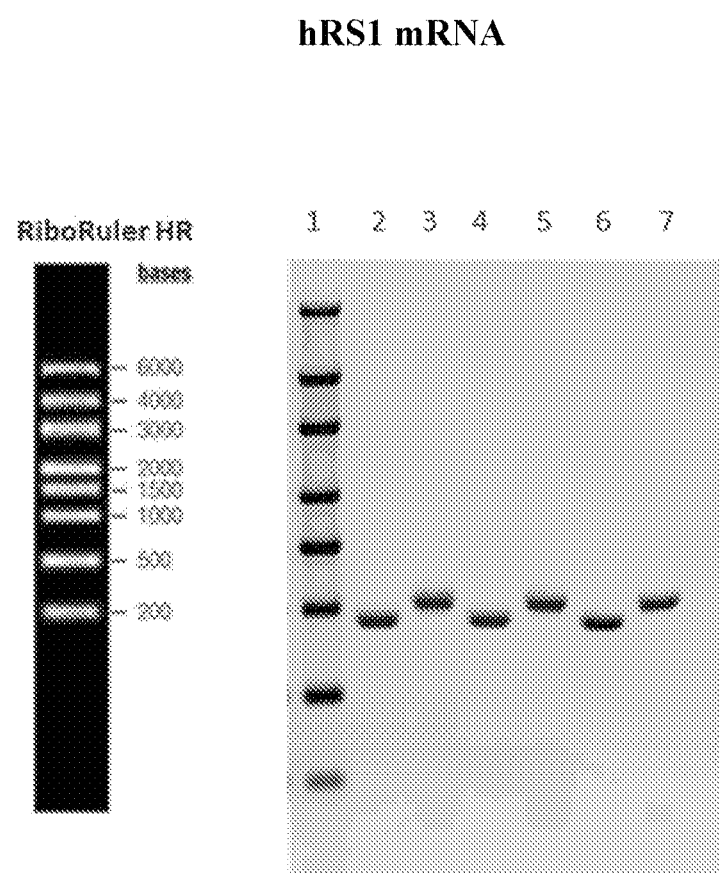

FIG. 10 shows digital images of agarose gel of human Retinoschisin 1 (RS1) mRNA transcribed with SP6 polymerase, with or without capping and tailing. The mRNA preparations were resolved in a 1% agarose gel in Glyoxal gel loading dye for 60 minutes. Lanes: lane 1, Riboruler molecular size marker (also shown on the left panel with size indicators); lanes 2, 4, and 6 are different preparations of different codon optimized hRS1 sequences, without the 5' cap and 3' poly A tail; lanes 3, 5 and 7 are capped and tailed mRNA, corresponding to the preparation samples in lanes 2, 4, and 6.

Figure 11:
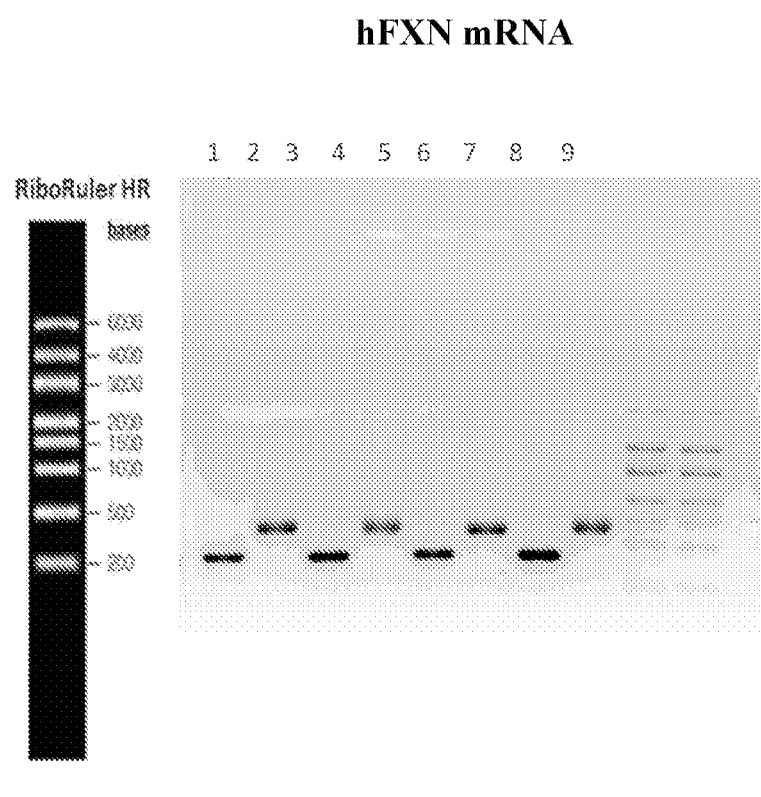

FIG. 11 shows digital images of agarose gel of human Frataxin (FXN) mRNA transcribed with SP6 polymerase, with or without capping and tailing. The mRNA preparations were resolved in a 1% agarose gel in Glyoxal gel loading dye for 60 minutes. Lanes: lanes 1, 3, 5 and 7 are different preparations of different codon optimized FXN mRNA sequences, without the 5' cap and 3' poly A tail; lanes 2, 4 6 and 8 are capped and tailed mRNA, corresponding to the preparation samples in lanes 1, 3, 5 and 7 respectively; lanes 10 and 11: Riboruler molecular size marker (also shown on the left panel with size indicators)

Figure 12A:
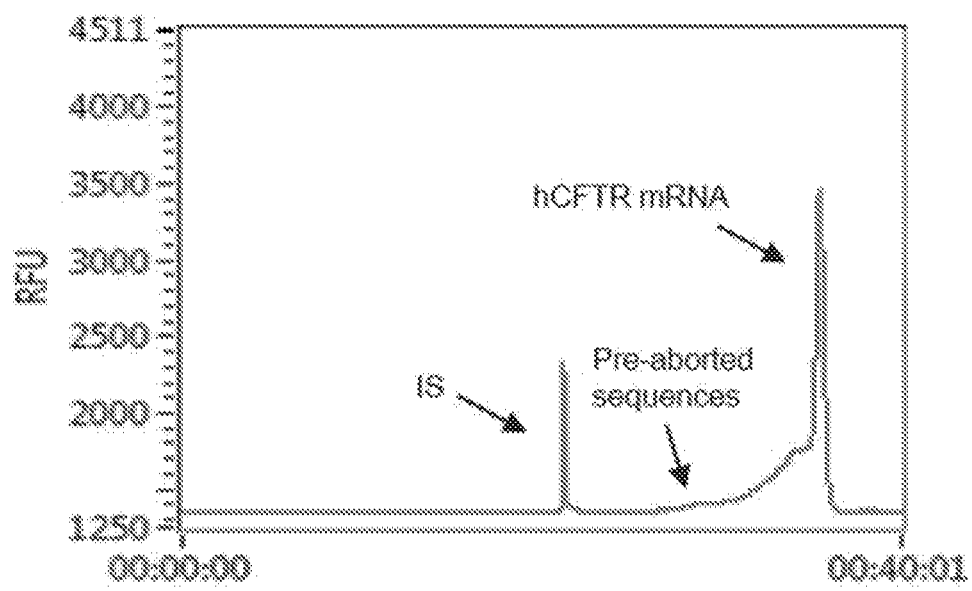
Figure 12B:
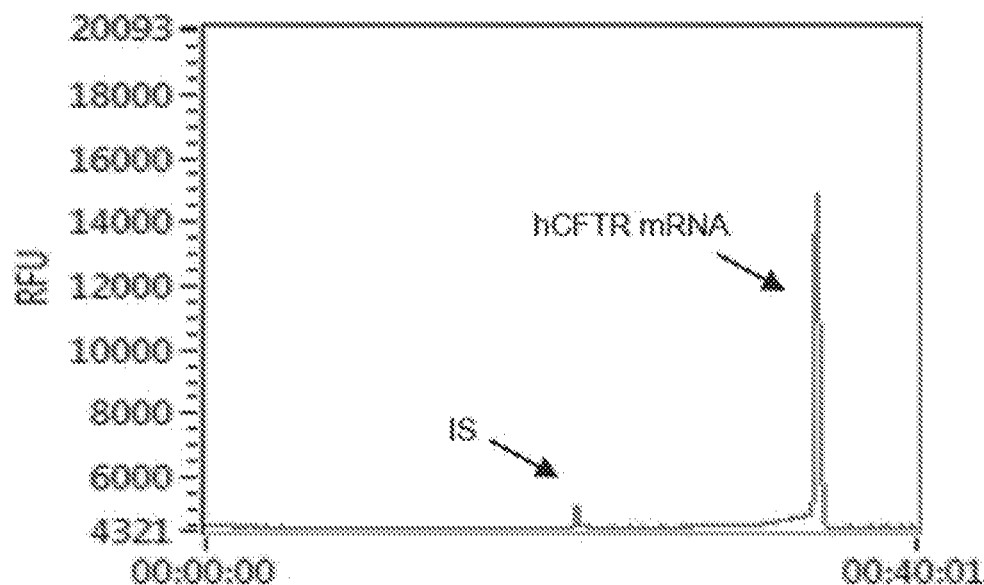

FIG. 12A and FIG. 12B are electropherograms showing fluorescence-based capillary electrophoresis profiles of codon-optimized hCFTR (CO-hCFTR) mRNA synthesized with T7 versus SP6 polymerase. The separation was performed using the SS RNA analysis kit and absorbance is plotted as a function of nucleotide size. CO-hCFTR T7 transcribed mRNA (FIG. 12A) after capping and tailing and CO-hCFTR SP6 transcribed mRNA (FIG. 10B) after capping and tailing.

Figure 13A:
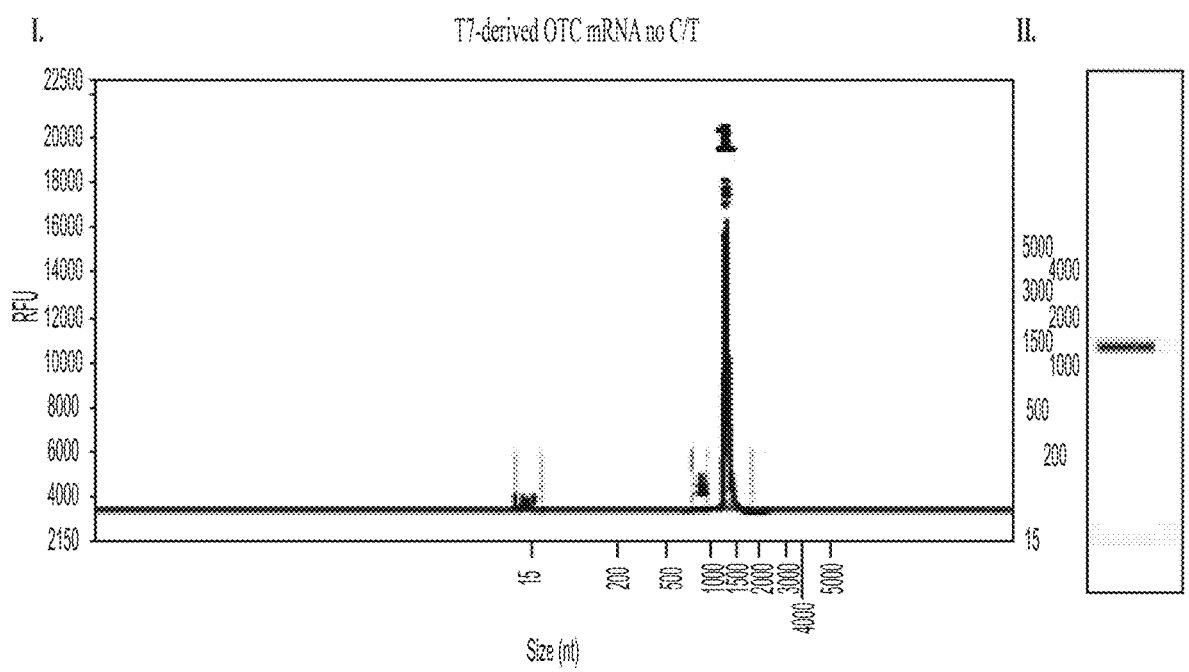
Figure 13B:
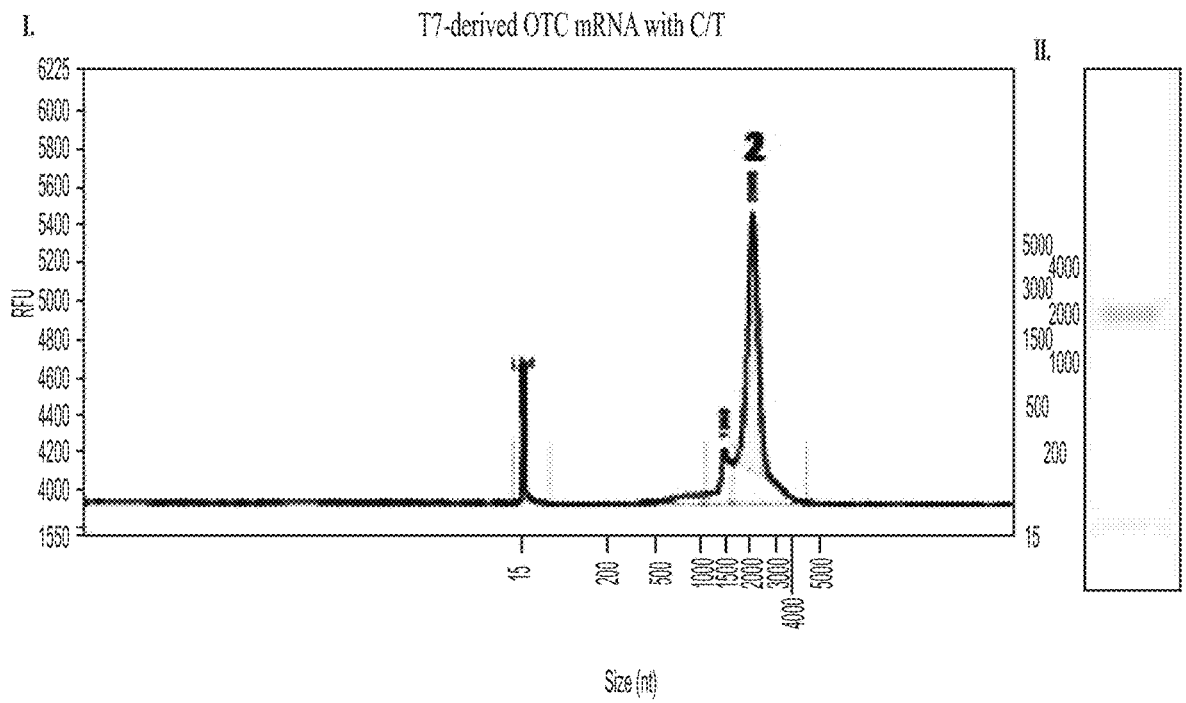
Figure 13C:
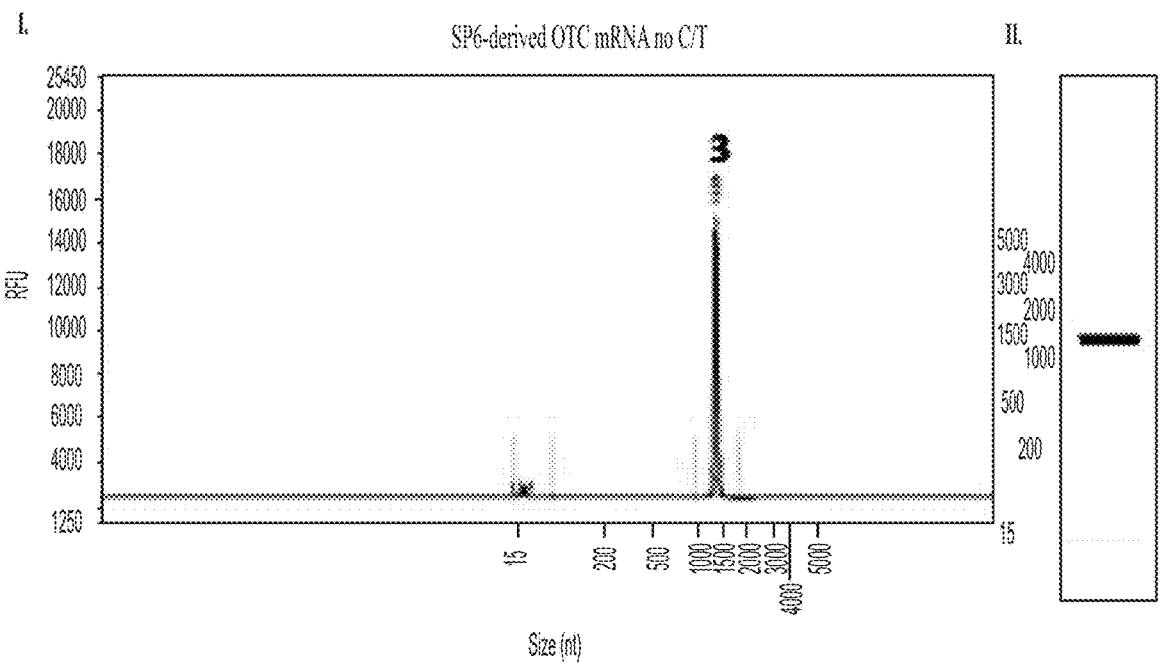
Figure 13D:
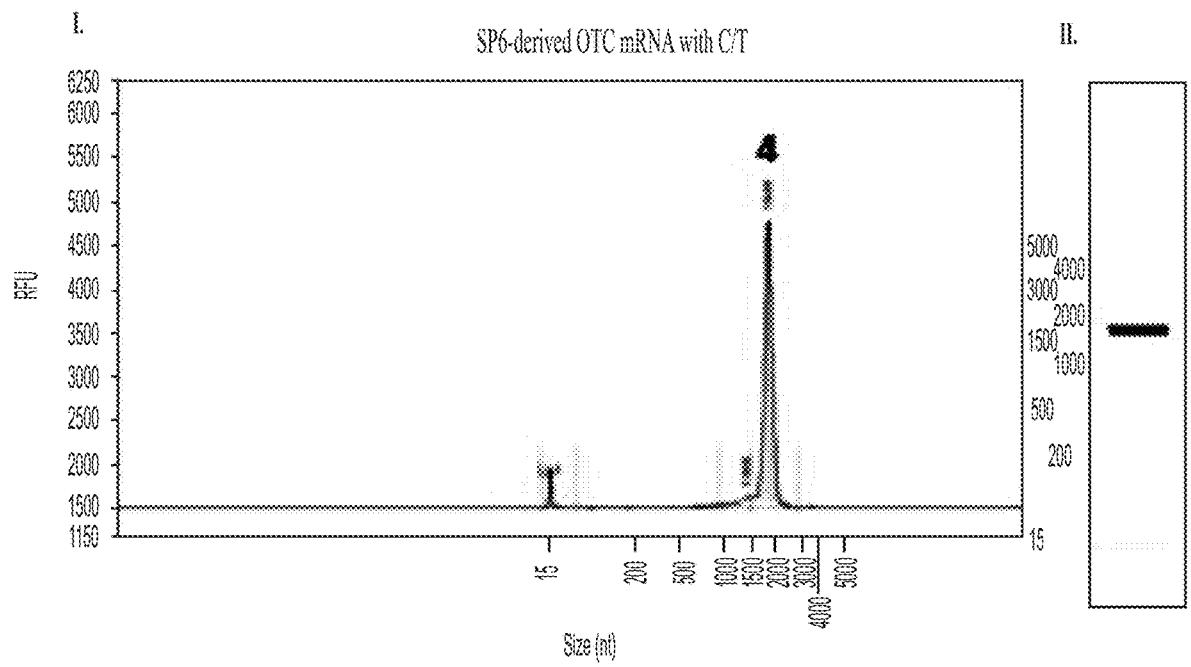

FIG. 13A to FIG. 13D compare OTC mRNA synthesized with T7 versus SP6 polymerase. In each Figure, sections I are electropherograms showing Capillary Electrophoresis profiles with total RNA absorbance plotted as a function of nucleotide size; sections II are digital gel images generated from the quantitative analysis of the total RNA. The separation was performed using the SS RNA analysis kit (15nt) and absorbance was plotted as a function of nucleotide size. OTC T7 transcribed mRNA in absence of capping and tailing (FIG. 13A), OTC T7 transcribed mRNA after capping and tailing (FIG. 13B) and OTC SP6 transcribed mRNA in absence of capping and tailing (FIG. 13C), OTC SP6 transcribed mRNA after capping and tailing (FIG. 13D).

Figure 14A:
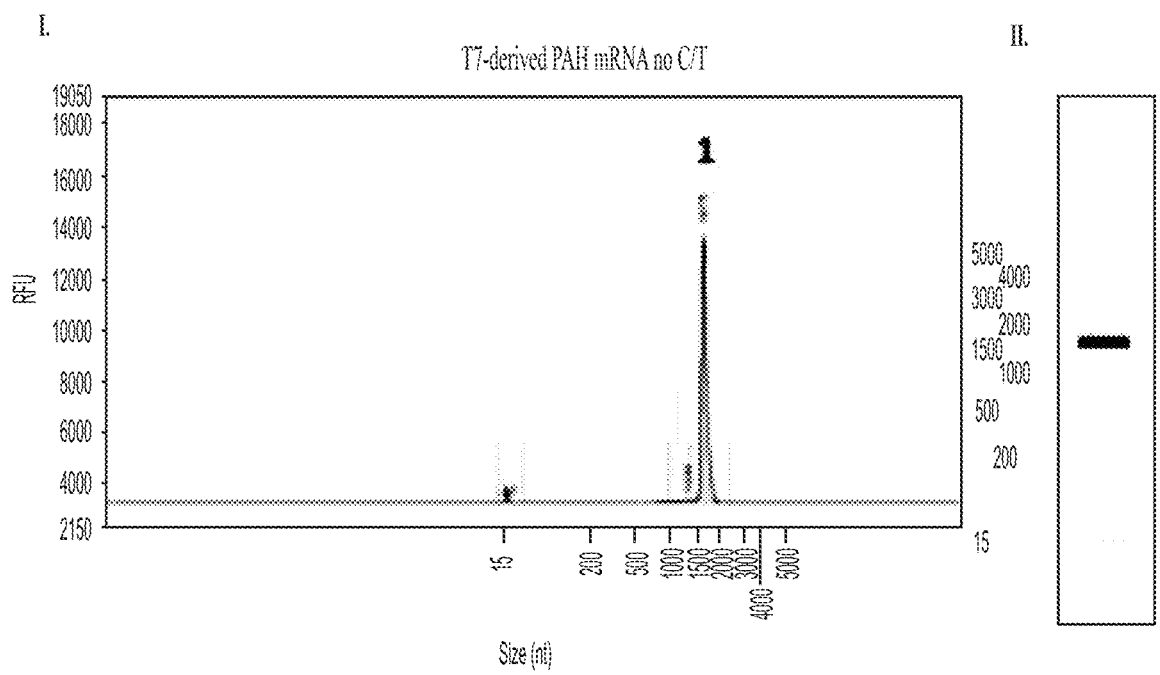
Figure 14B:
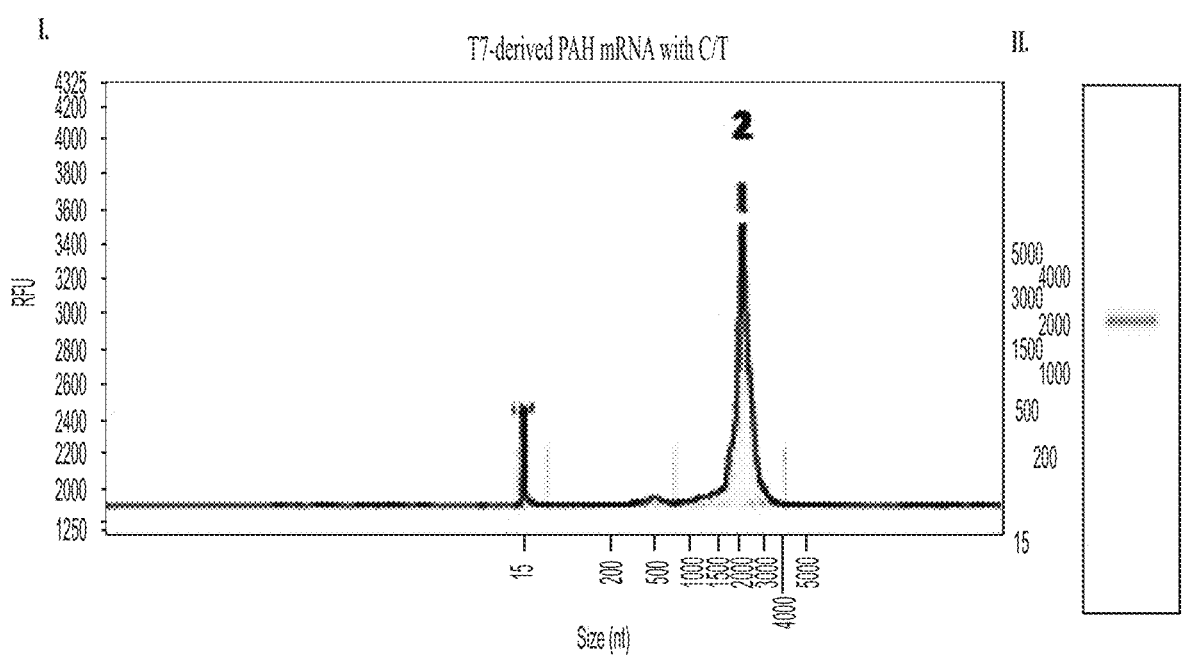
Figure 14C:
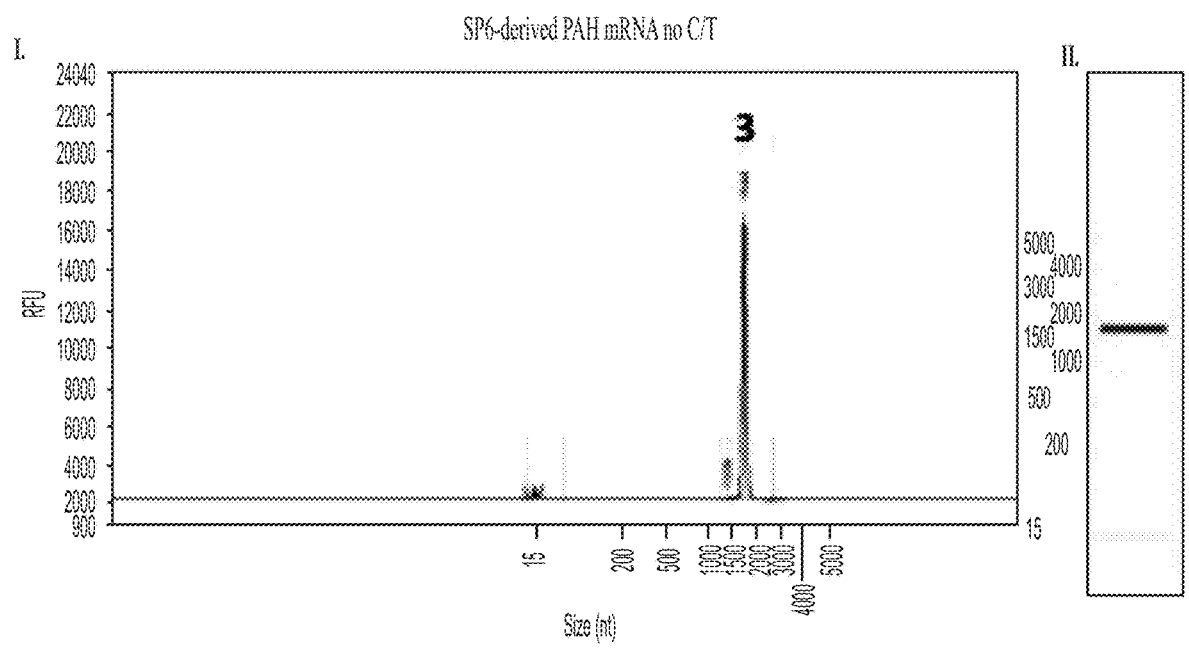
Figure 14D:
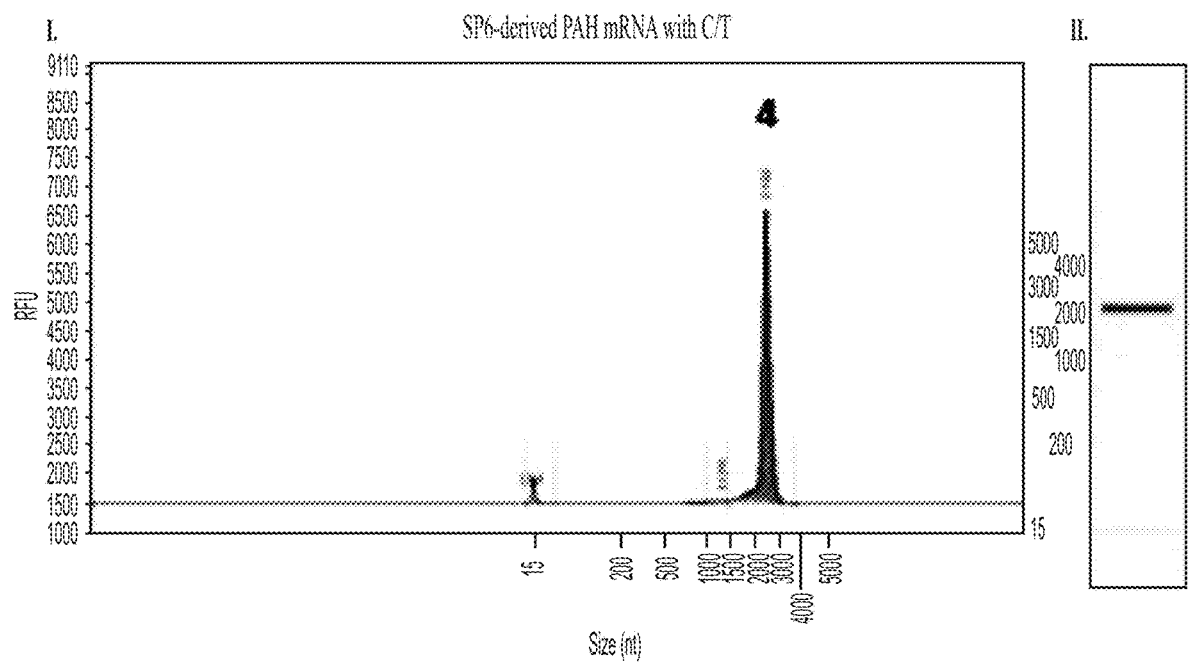

FIG. 14A to FIG. 14D compare PAH mRNA synthesized with T7 versus SP6 polymerase. In each Figure, sections I are electropherograms showing Capillary Electrophoresis profiles with total RNA absorbance plotted as a function of nucleotide size; sections II are digital gel images generated from the quantitative analysis of the total RNA. The separation was performed using the SS RNA analysis kit (15nt) and absorbance is plotted as a function of nucleotide size. PAH T7 transcribed mRNA in absence of capping and tailing (FIG. 14A), PAH T7 transcribed mRNA after capping and tailing (FIG. 14B); and PAH SP6 transcribed mRNA in absence of capping and tailing (FIG. 14C), and PAH SP6 transcribed mRNA after capping and tailing (FIG. 14D).

Figure 15A:
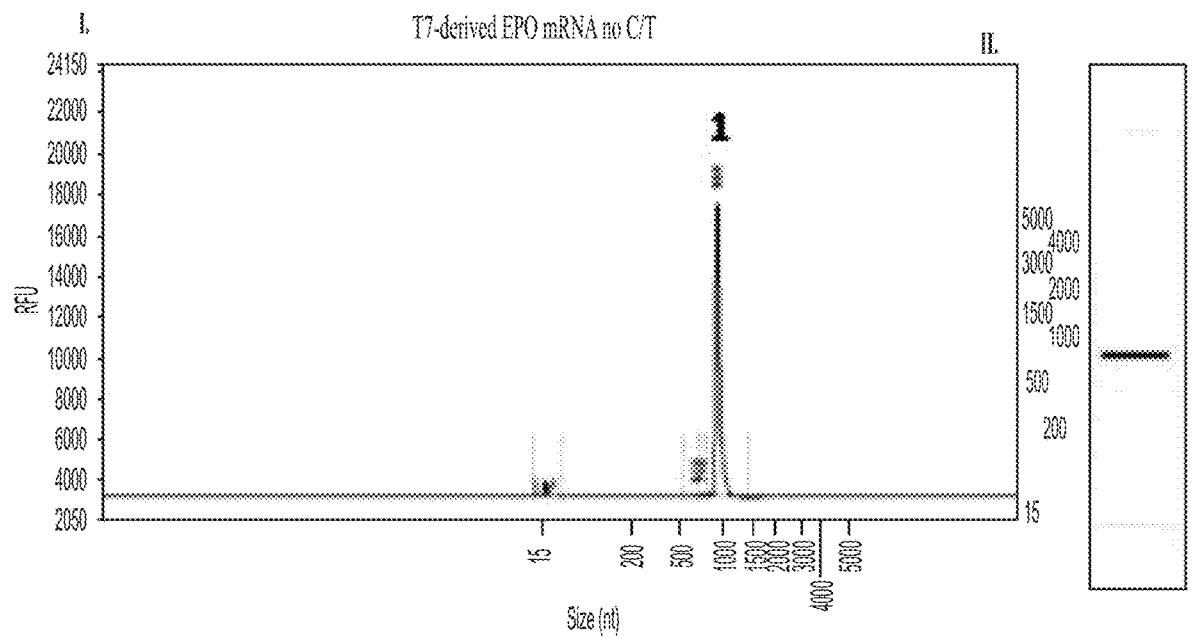
Figure 15B:
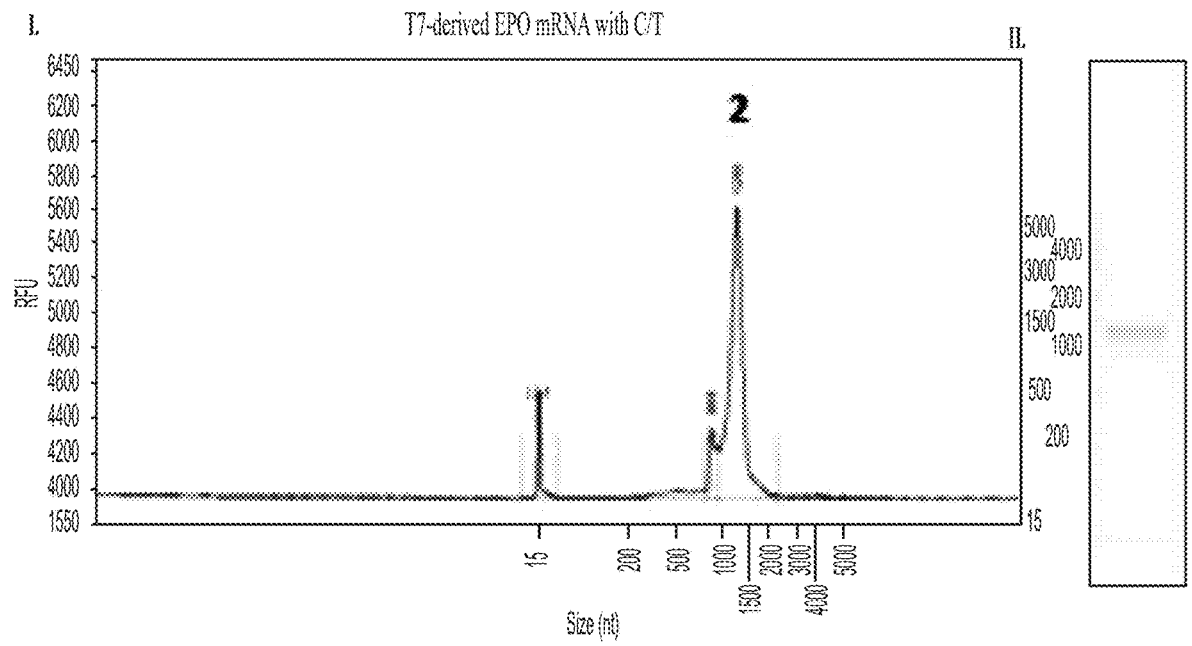
Figure 15C:
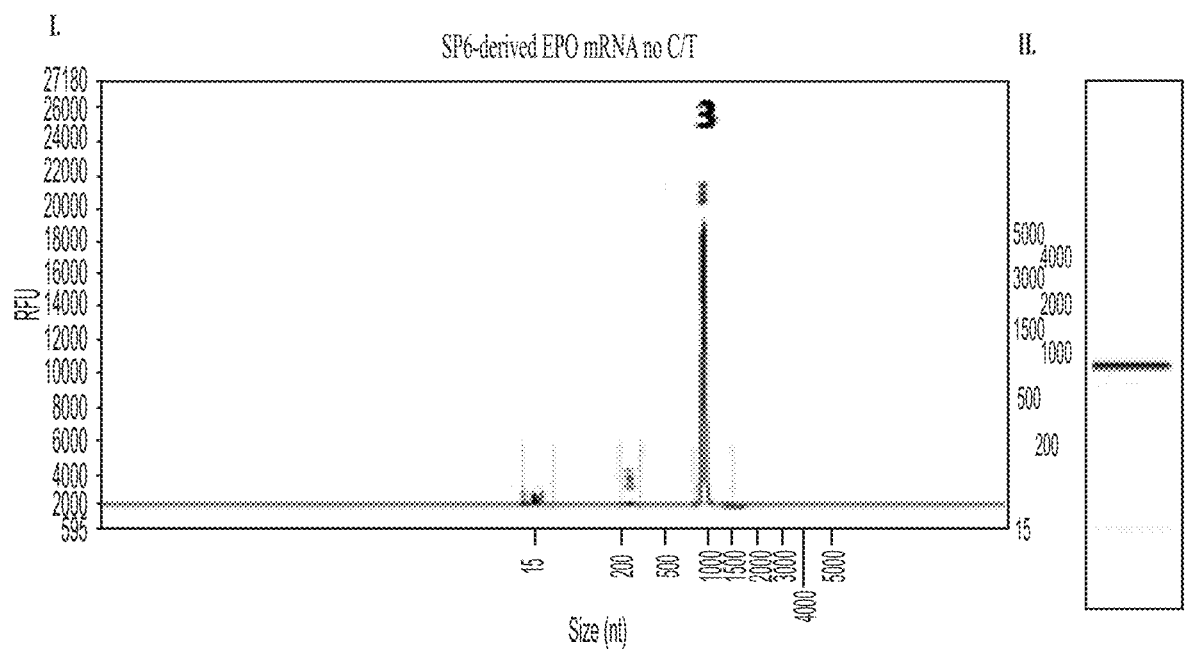
Figure 15D:
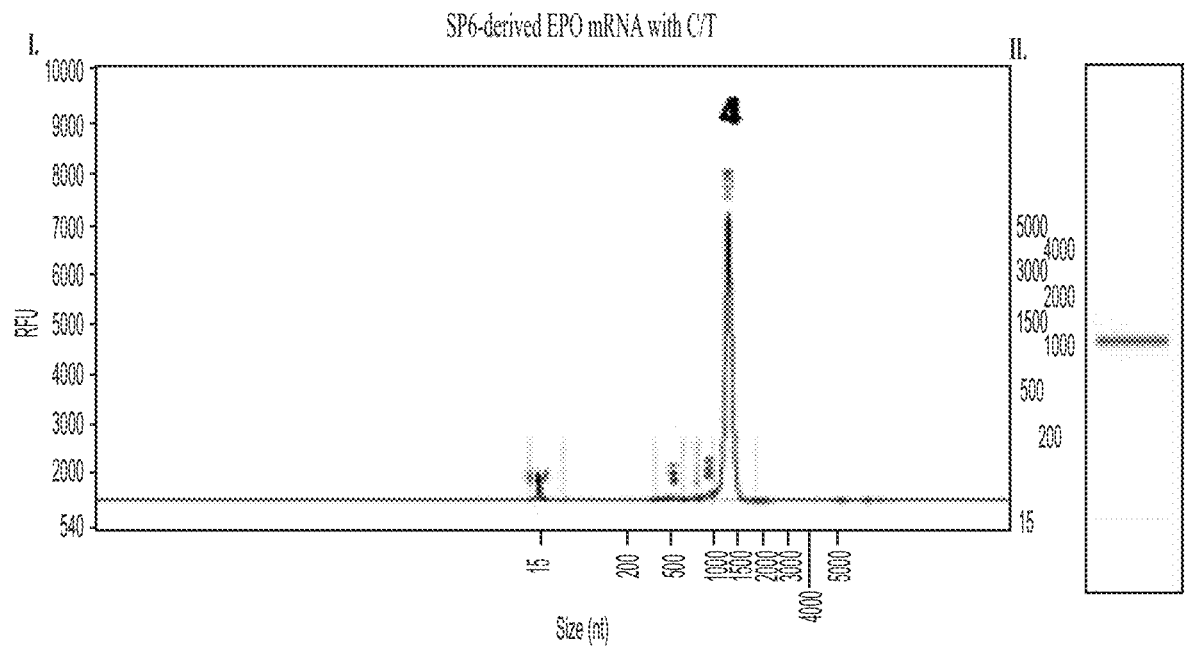

FIG. 15A to FIG. 15D compare EPO mRNA synthesized with T7 versus SP6 polymerase. In each Figure, sections I are electropherograms showing Capillary Electrophoresis profiles with total RNA absorbance plotted as a function of nucleotide size; sections II are digital gel images generated from the quantitative analysis of the total RNA. The separation was performed using the SS RNA analysis kit (15nt) and absorbance is plotted as a function of nucleotide size. EPO T7 transcribed mRNA in absence of capping and tailing (FIG. 15A), after capping and tailing (FIG. 15B) and EPO SP6 transcribed mRNA in absence of capping and tailing (FIG. 15C), EPO SP6 transcribed mRNA after capping and tailing (FIG. 15D).

Figure 16A:
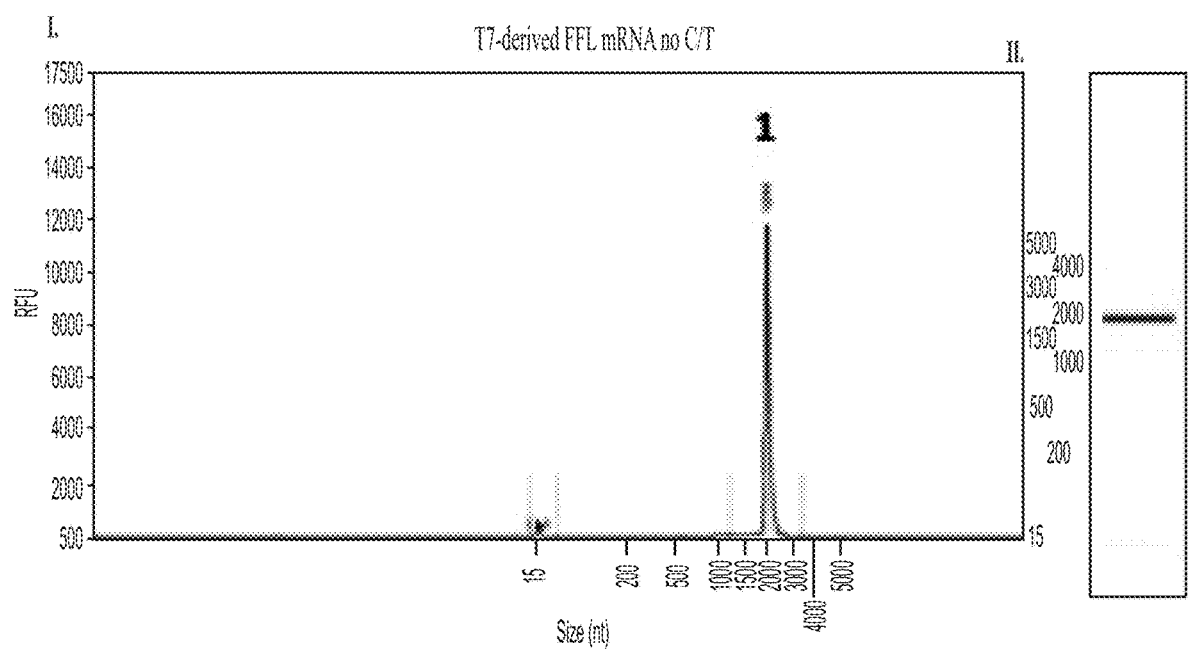
Figure 16B:
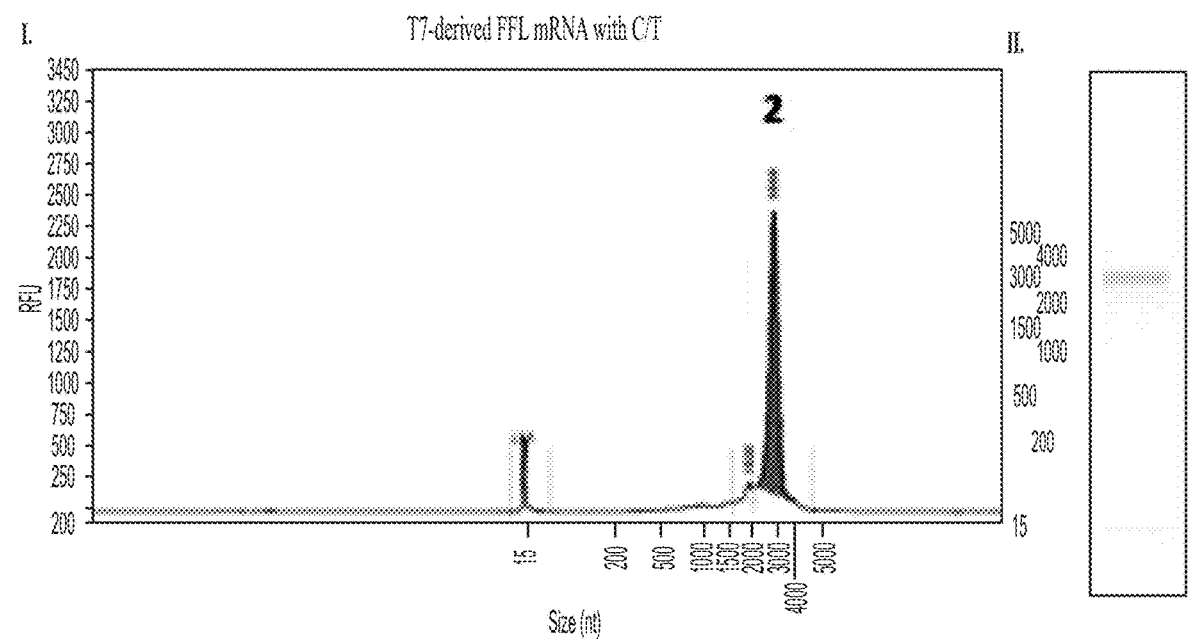
Figure 16C:
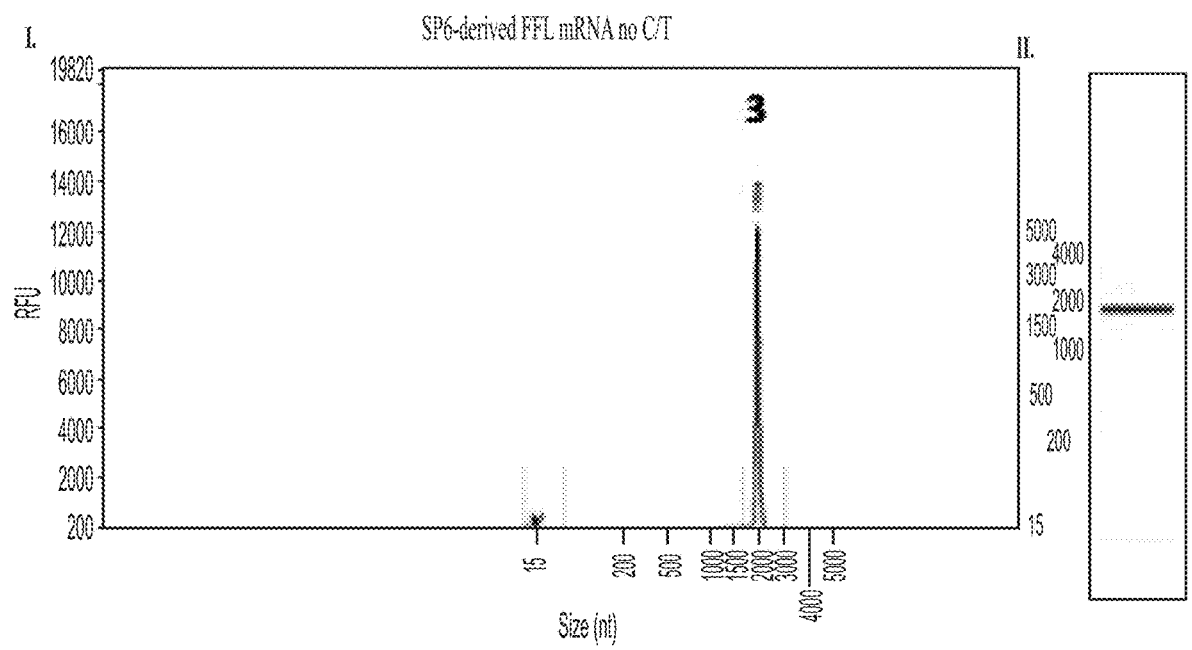
Figure 16D:
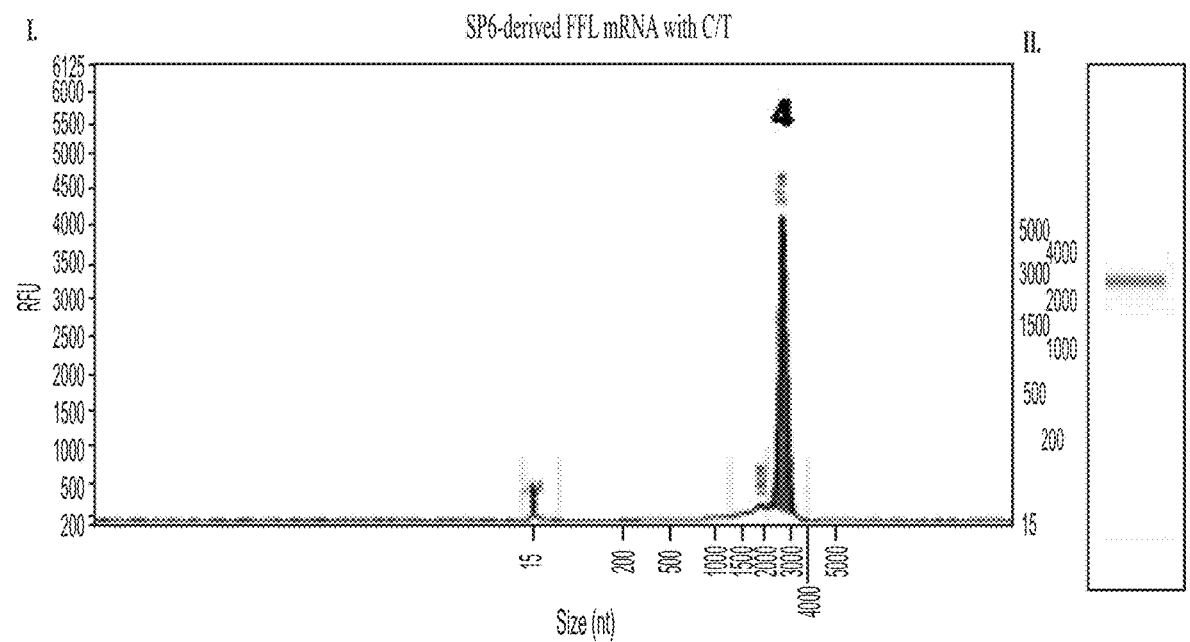

FIG. 16A to FIG. 16D compare FFL mRNA synthesized with T7 versus SP6 polymerase. In each Figure, sections I are electropherograms showing Capillary Electrophoresis profiles with total RNA absorbance plotted as a function of nucleotide size; sections II are digital gel images generated from the quantitative analysis of the total RNA. The separation was performed using the SS RNA analysis kit (15nt) and absorbance is plotted as a function of nucleotide size. FFL T7 transcribed mRNA in absence of capping and tailing (FIG. 16A); FFL T7 transcribed mRNA after capping and tailing (FIG. 16B) and FFL SP6 transcribed mRNA in absence of capping and tailing (FIG. 16C) FFL SP6 transcribed mRNA after capping and tailing (FIG. 16D).

Figure 17A:
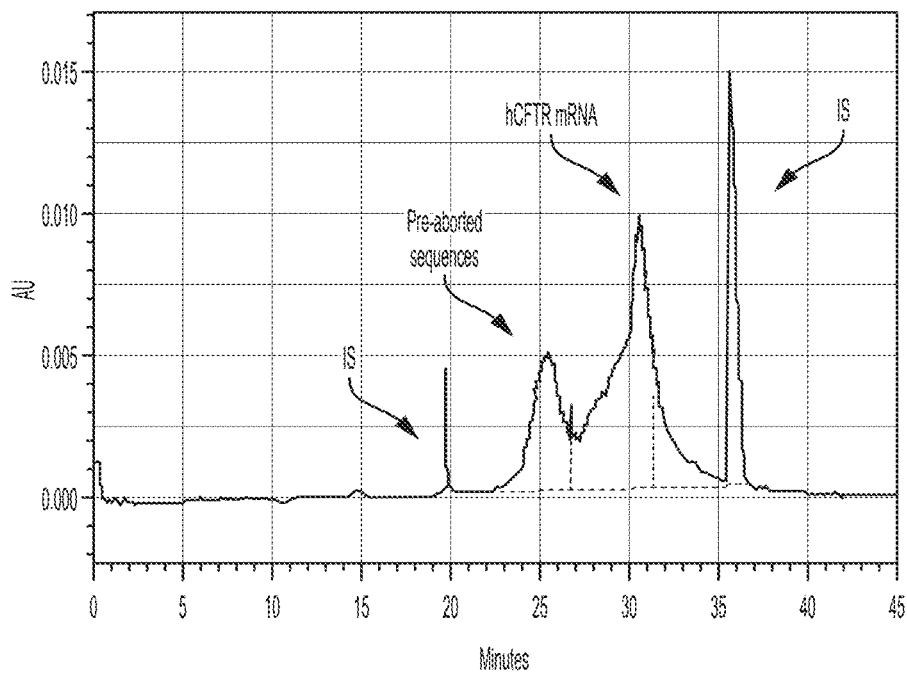
Figure 17B:
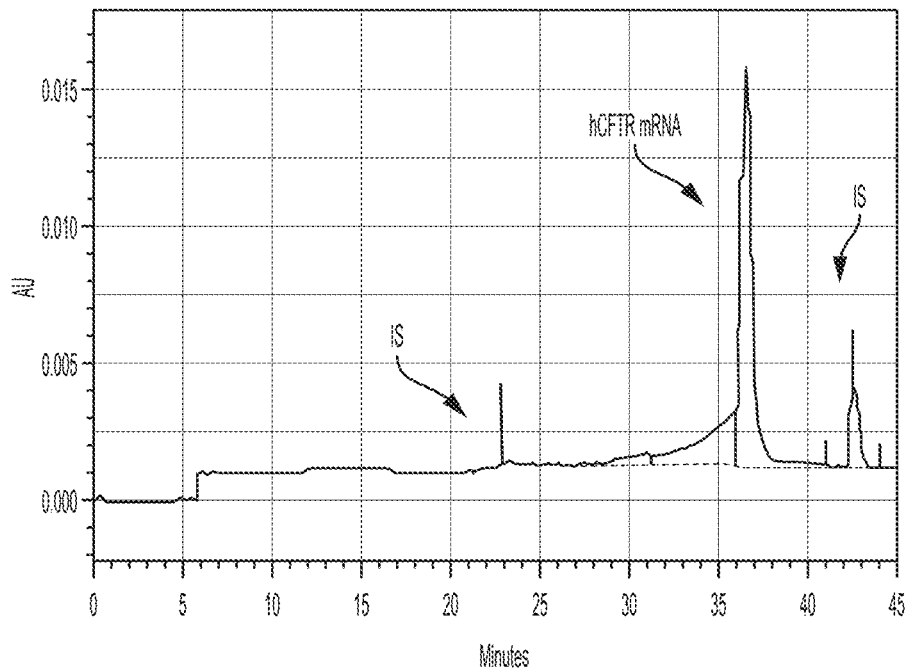

FIG. 17A and FIG. 17B are electropherograms showing UV absorption spectroscopy-based capillary electrophoresis profiles of CO-hCFTR mRNA synthesized with T7 versus SP6 polymerase. CO-hCFTR T7 transcribed mRNA (FIG. 17A) after capping and tailing and CO-hCFTR SP6 transcribed mRNA (FIG. 17B) after capping and tailing. Internal Standard (IS) is shown.

Figure 18:
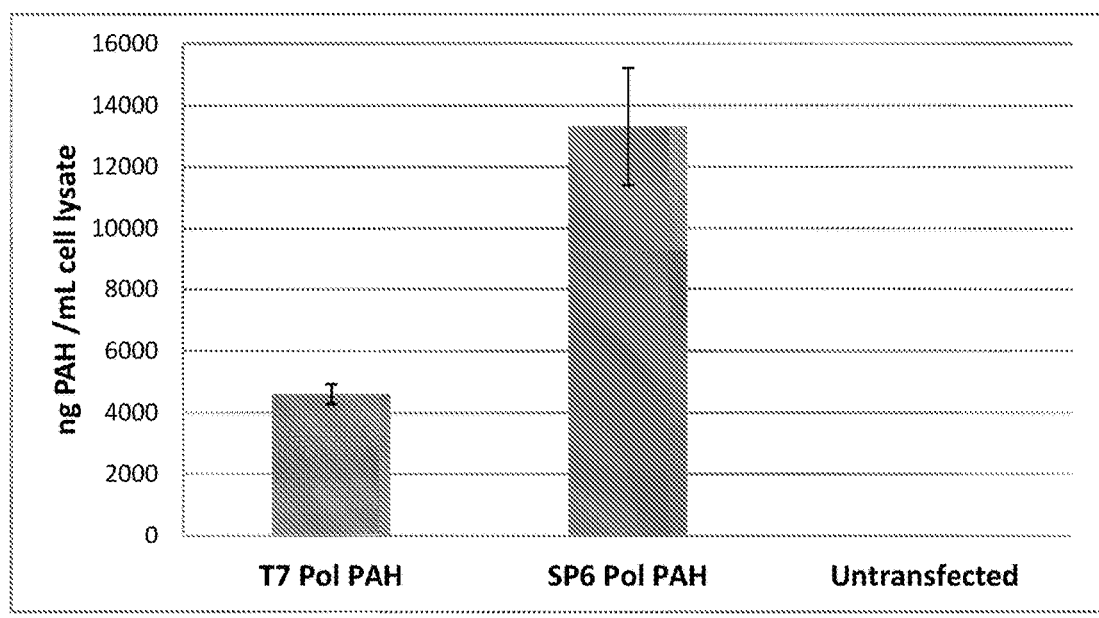

FIG. 18 is a graph showing human PAH protein expression in HEK293 cells following transfection of T7- or SP6-derived PAH transcripts.

Figure 19:
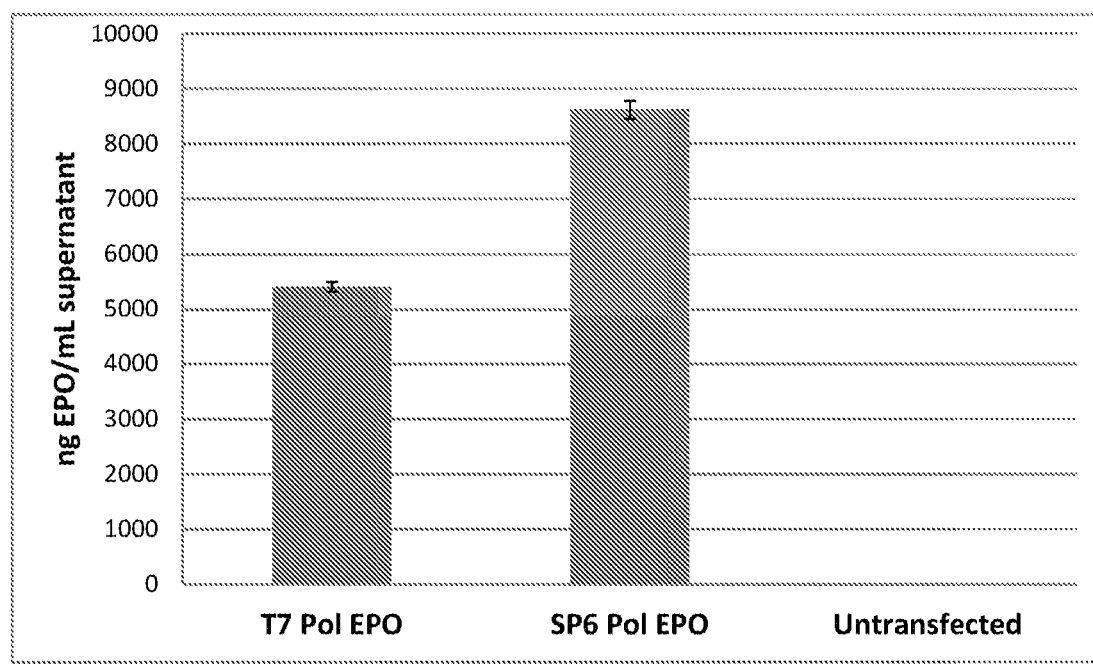

FIG. 19 is a graph showing human EPO protein expression in HEK293 cells following transfection of T7- or SP6-derived EPO transcripts.

Figure 20:
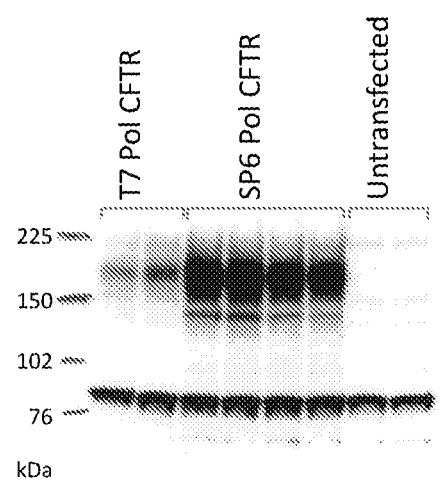

FIG. 20 is a Western blot showing CFTR protein expression in HEK293 cells following transfection of T7- or SP6-derived CFTR transcripts. Equivalent amounts of template DNA was used in the transcription reactions. Equivalent amounts of transcripts were transfected into the HEK293 cells.

Figure 21:
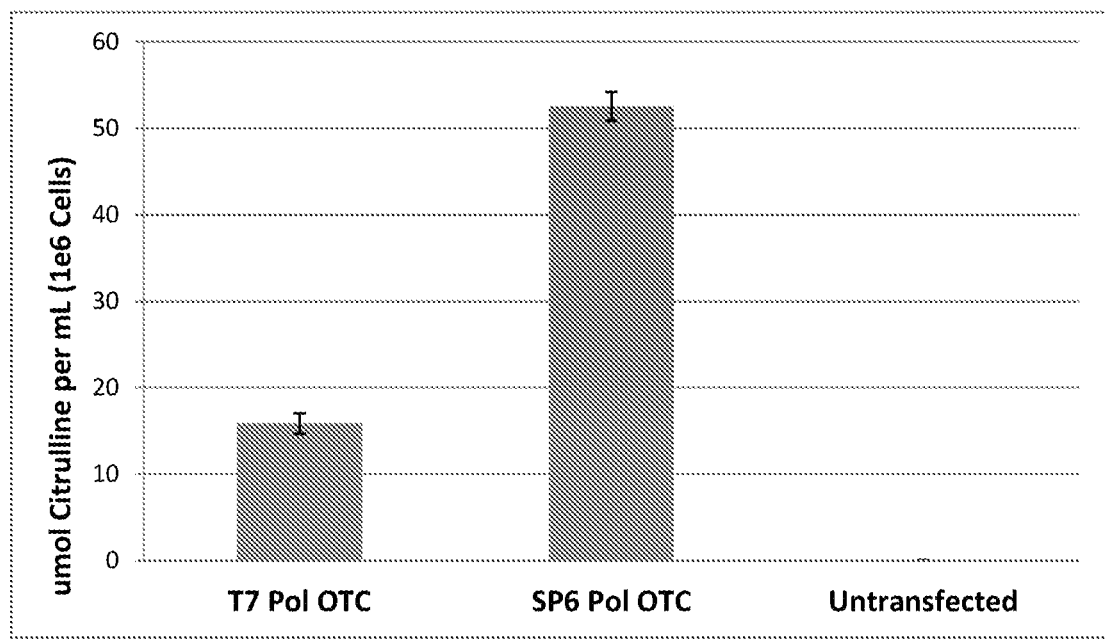

FIG. 21 is a graph showing citrulline production, which demonstrates human OTC protein activity in HEK293 cells following transfection of T7- or SP6-derived hOTC transcripts. Equivalent amounts of template DNA was used in the transcription reactions. Equivalent amounts of transcripts were transfected into the HEK293 cells.

Figure 22:
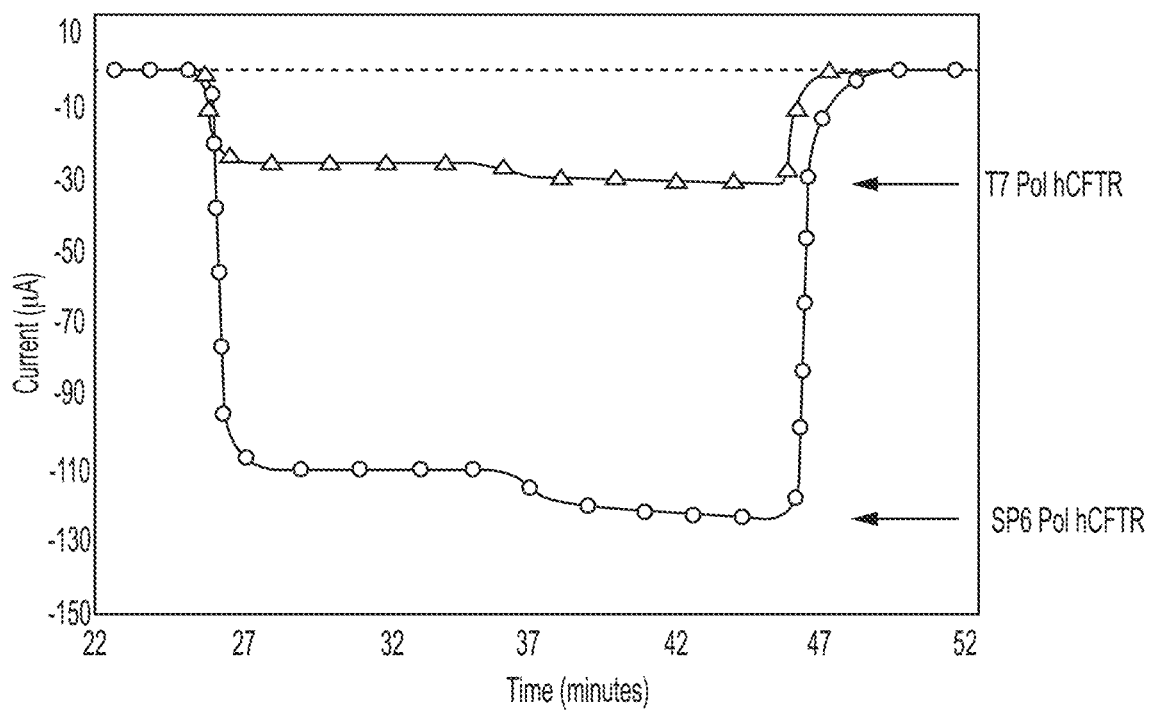

FIG. 22 is a graph showing chamber electrophysiological data, which demonstrates current generated in Fisher Rat thyroid cells from CFTR protein expressed following transfection of T7- or SP6-derived transcripts.

Figure 23:
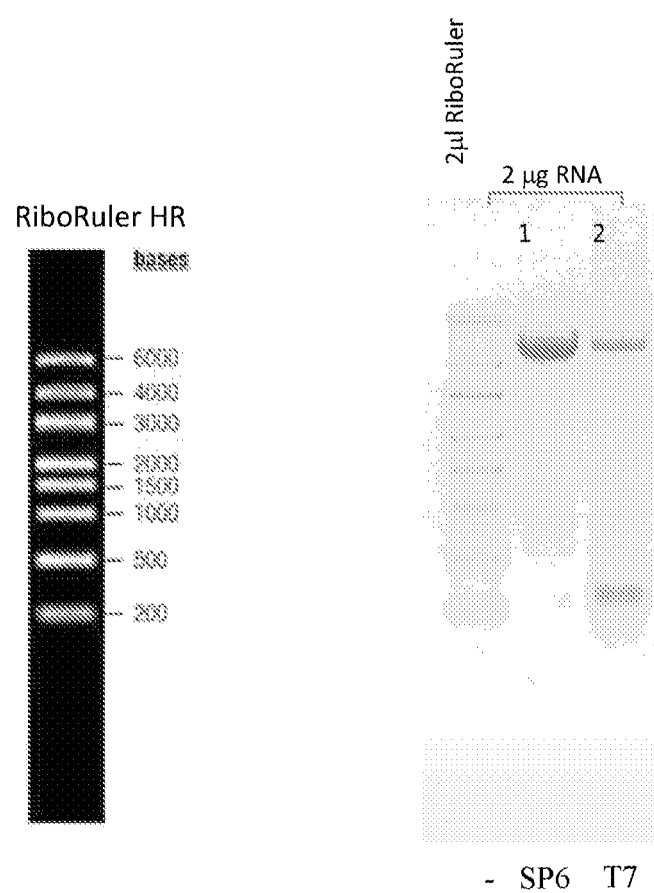

FIG. 23 is a digital image of an agarose gel of large scale human CFTR mRNA transcribed with SP6 versus T7 polymerase, capped and tailed product. 2 micrograms of a 10 gram batch preparation was run per lane of a 1% agarose gel in Glyoxal gel loading dye for 60 minutes. Left panel, migration of RiboRuler reference RNA molecular weight marker run in the same agarose gel and the respective molecular weights of the migrating bands.

Figure 24A:
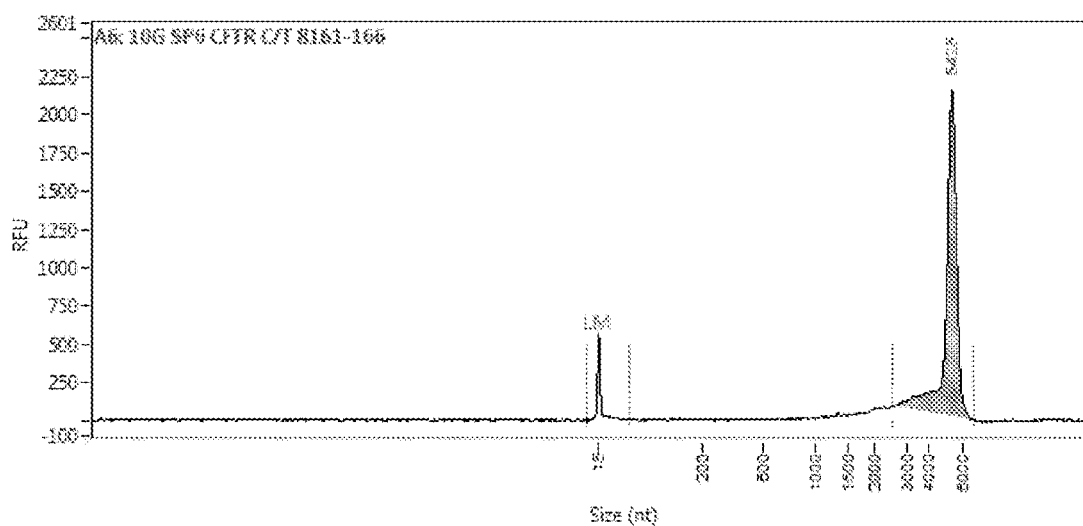
Figure 24B:
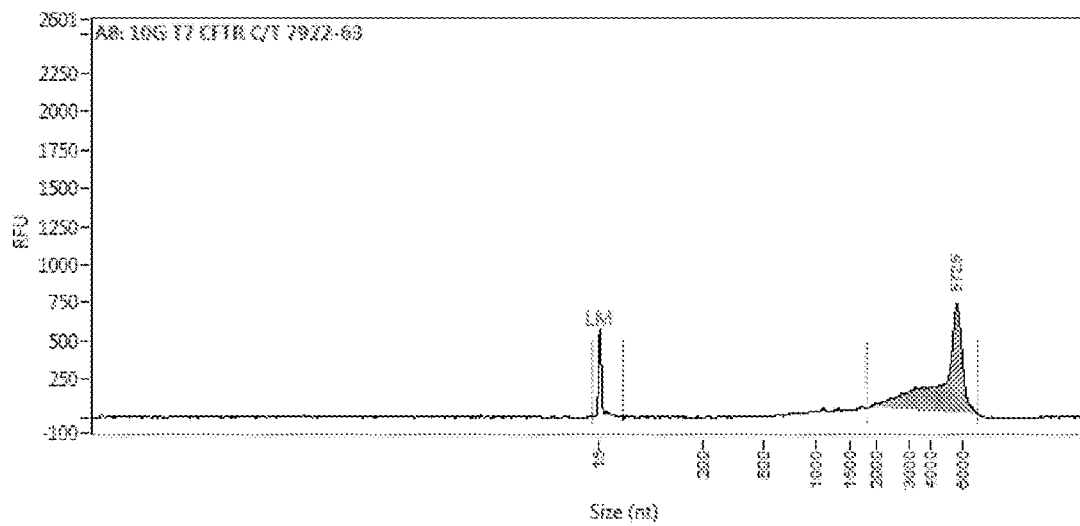
Figure 24C:
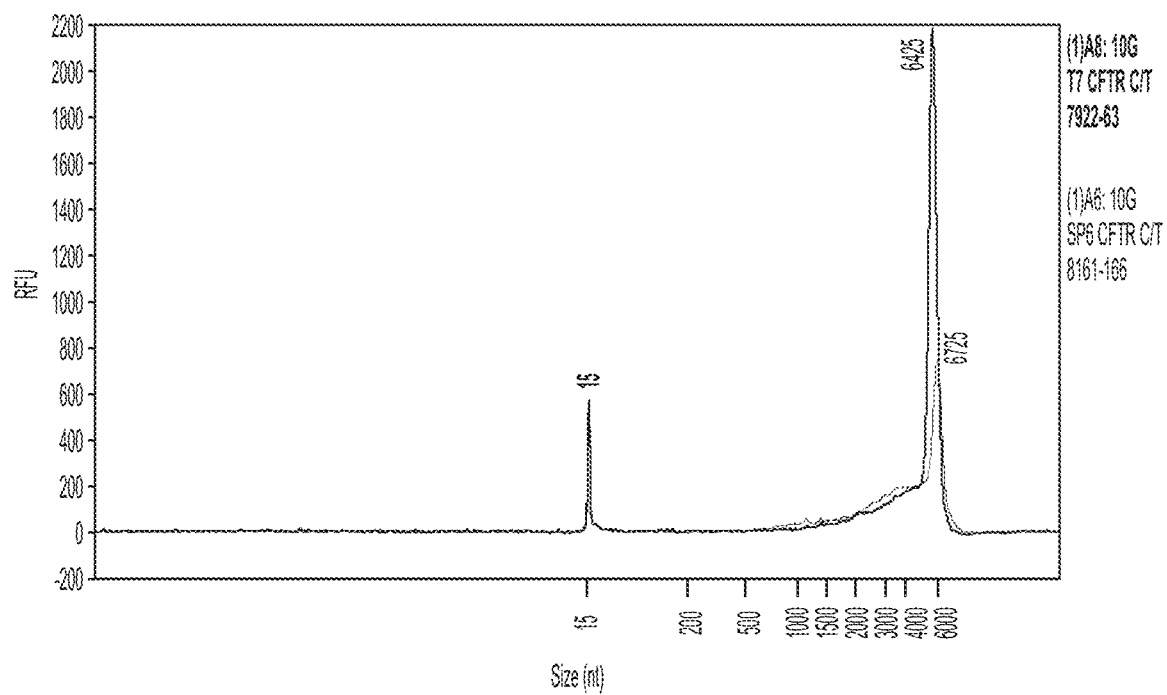

FIG. 24A-C are electropherograms showing fluorescence-based capillary electrophoresis profiles of a 10-gram batch preparation of codon-optimized hCFTR (CO-hCFTR) mRNA synthesized with SP6 versus T7 polymerase. The separation was performed using the SS RNA analysis kit and absorbance is plotted as a function of nucleotide size. CO-hCFTR SP6 transcribed RNA (FIG. 24A) after capping and tailing and CO-hCFTR T7 transcribed RNA (FIG. 24B) after capping and tailing. FIG. 24C shows superimposition of the electropherograms corresponding to SP6-derived 10-gram batch preparation of mRNA and T7-derived 10-gram batch preparation of mRNA showing relative peak heights.

Figure 25:
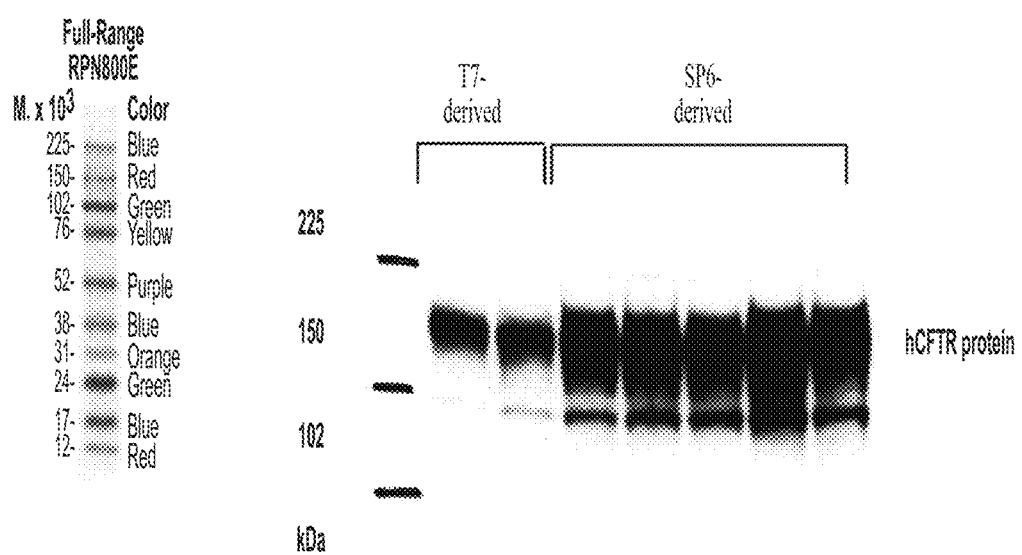

FIG. 25 is a western blot of human CFTR, using protein extracts from cells transfected with large scale preparation of hCFTR mRNA using SP6. Human embryonic kidney (HEK 293) cells were transfected with multiple preparations of SP-6 derived human CFTR mRNA prepared at 10-gram scale. Equivalent amounts of template DNA was used in the transcription reactions. Equivalent amounts of transcripts were then transfected into the HEK293 cells. A distinct hCFTR protein product was detected in each case. Upper panel, cells were transfected with 4 µg of mRNA. Lower panel, cells were transfected with 1 µg of mRNA.

Figure 26:
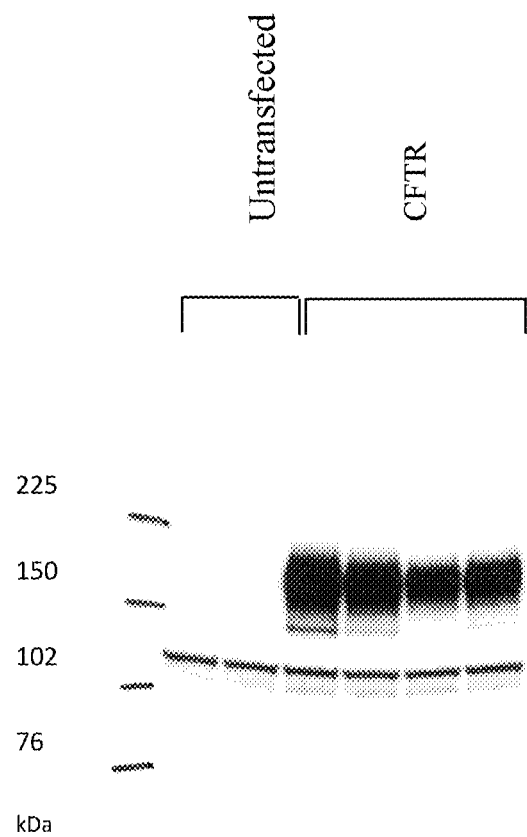

FIG. 26 depicts hCFTR protein expression detected by western blot analysis of hCFTR mRNA transfected HEK 293 cell extracts. The mRNAs were synthesized in 25-gram batches, using SP6 for IVT.

Figure 27:
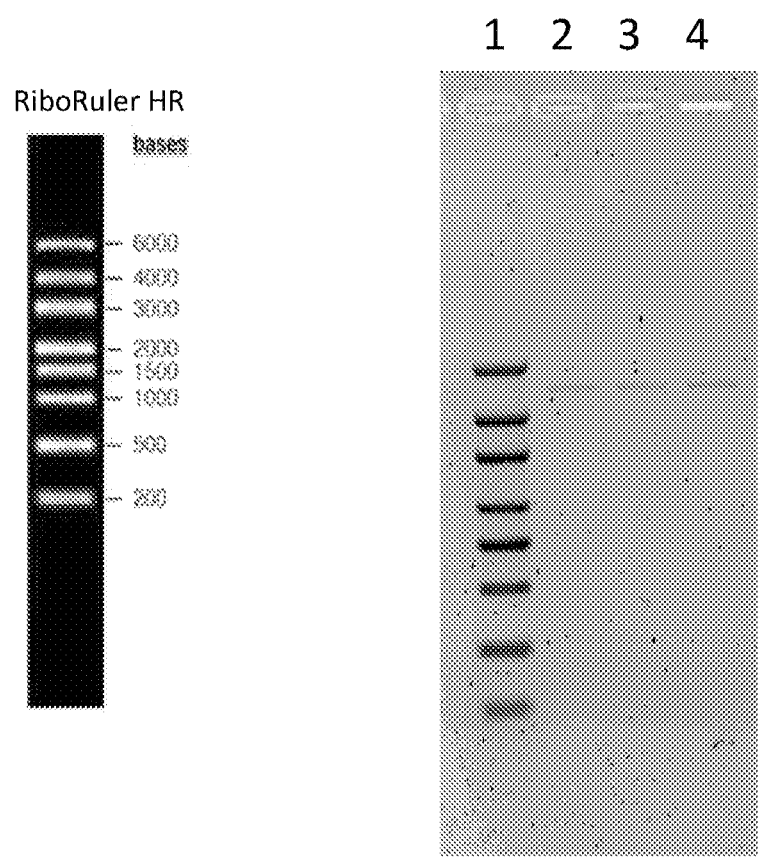

FIG. 27 shows agarose gel electrophoresis bands of 50-gram scale preparations of CFTR mRNA run in parallel with a 10-gram batch preparation. Lane 1, molecular weight marker, Lanes 2 and 3, aliquots from the 50-gram batch synthesized mRNA using SP6, Lane 4, 10-gram batch synthesized mRNA as control.

DEFINITIONS

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or evident from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein reflects normal fluctuations that can be appreciated by a skilled artisan.

As used herein, term "abortive transcript" or "pre-aborted transcript" or the like, in its broadest sense, is any transcript that is shorter than a full-length mRNA molecule encoded by the DNA template. In some embodiments, an abortive transcript may be less than 90% of the length of the full-length mRNA molecule that is transcribed from the target DNA molecule, e.g., less than 80%, 70%, 60%, 50%, 40%, 30%, 20%, 10%, 5%, 1% of the length of the full-length mRNA molecule.

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "batch" would not mean mRNA synthesized at different times that are combined to achieve the desired amount.

As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

As used herein, the terms "drug", "medication", "therapeutic", "active agent", "therapeutic compound", "composition", or "compound" are used interchangeably and refer to any chemical entity, pharmaceutical, drug, biological, botanical, and the like that can be used to treat or prevent a disease, illness, condition, or disorder of bodily function. A drug may comprise both known and potentially therapeutic compounds. A drug may be determined to be therapeutic by screening using the screening known to those having ordinary skill in the art. A "known therapeutic compound", "drug", or "medication" refers to a therapeutic compound that has been shown (e.g., through animal trials or prior experience with administration to humans) to be effective in such treatment. A "therapeutic regimen" relates to a treatment comprising a "drug", "medication", "therapeutic", "active agent", "therapeutic compound", "composition", or "compound" as disclosed herein and/or a treatment comprising behavioral modification by the subject and/or a treatment comprising a surgical means.

As used herein, the term "encapsulation," or grammatical equivalent, refers to the process of confining an mRNA molecule within a nanoparticle. The process of incorporation of a desired mRNA into a nanoparticle is often referred to as "loading". Exemplary methods are described in Lasic, et al., FEBS Lett., 312: 255-258, 1992, which is incorporated herein by reference. The nanoparticle-incorporated nucleic acids may be completely or partially located in the interior space of the nanoparticle, within the bilayer membrane (for liposomal nanoparticles), or associated with the exterior surface of the nanoparticle.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalent, are used interchangeably.

As used herein, "full-length mRNA" is as characterized when using a specific assay, e.g., gel electrophoresis and detection using UV and UV absorption spectroscopy with separation by capillary electrophoresis. The length of an mRNA molecule that encodes a full-length polypeptide is at least 50% of the length of a full-length mRNA molecule that is transcribed from the target DNA, e.g., at least 60%, 70%, 80%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the length of a full-length mRNA molecule that is transcribed from the target DNA.

As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

As used herein, the term "impurities" refers to substances inside a confined amount of liquid, gas, or solid, which differ from the chemical composition of the target material or compound. Impurities are also referred to as contaminants.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man.

As used herein, the term "messenger RNA (mRNA)" refers to a polyribonucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, in vitro transcribed, or chemically synthesized.

mRNA is typically thought of as the type of RNA that carries information from DNA to the ribosome. The existence of mRNA is usually very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby poly A moiety is added to the 3' end of the mRNA molecule. The presence of this "tail" serves to protect the mRNA from exonuclease degradation. Messenger RNA typically is translated by the ribosomes into a series of amino acids that make up a protein.

As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone As used herein, the term "shortmer" is used to specifically refer to prematurely aborted short mRNA oligonucleotide, also called short abortive RNA transcripts, which are products of incomplete mRNA transcription during in vitro transcription reactions. Shortmers, prematurely aborted mRNA, pre-abortive mRNA, or short abortive mRNA transcripts are used interchangeably in the specification.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION OF THE INVENTION

The present invention provides large-scale in vitro synthesis methods that produce mRNA significantly enriched with full-length transcripts.

SP6 RNA Polymerase

SP6 RNA Polymerase is a DNA-dependent RNA polymerase with high sequence specificity for SP6 promoter sequences. Typically, this polymerase catalyzes the 5'→3' in vitro synthesis of RNA on either single-stranded DNA or double-stranded DNA downstream from its promoter; it incorporates native ribonucleotides and/or modified ribonucleotides into the polymerized transcript.

The sequence for bacteriophage SP6 RNA polymerase was initially described (GenBank: Y00105.1) as having the following amino acid sequence:

```
                                            (SEQ ID NO: 1)
MQDLHAIQLQLEEEMFNGGIRRFEADQQRQIAAGSESDTAWNRRLLSEL

IAPMAEGIQAYKEEYEGKKGRAPRALAFLQCVENEVAAYITMKVVMDML

NTDATLQAIAMSVAERIEDQVRFSKLEGHAAKYFEKVKKSLKASRTKSY

RHAHNVAVVAEKSVAEKDADFDRWEAWPKETQLQIGTTLLEILEGSVFY

NGEPVFMRAMRTYGGKTIYYLQTSESVGQWISAFKEHVAQLSPAYAPCV

IPPRPWRTPFNGGFHTEKVASRIRLVKGNREHVRKLTQKQMPKVYKAIN

ALQNTQWQINKDVLAVIEEVIRLDLGYGVPSFKPLIDKENKPANPVPVE

FQHLRGRELKEMLSPEQWQQFINWKGECARLYTAETKRGSKSAAVVRMV

GQARKYSAFESIYFVYAMDSRSRVYVQSSTLSPQSNDLGKALLRFTEGR

PVNGVEALKWFCINGANLWGWDKKTFDVRVSNVLDEEFQDMCRDIAADP

LTFTQWAKADAPYEFLAWCFEYAQYLDLVDEGRADEFRTHLPVHQDGSC

SGIQHYSAMLRDEVGAKAVNLKPSDAPQDIYGAVAQVVIKKNALYMDAD

DATTFTSGSVTLSGTELRAMASAWDSIGITRSLTKKPVMTLPYGSTRLT

CRESVIDYIVDLEEKEAQKAVAEGRTANKVHPFEDDRQDYLTPGAAYNY

MTALIWPSISEVVKAPIVAMKMIRQLARFAAKRNEGLMYTLPTGFILEQ

KIMATEMLRVRTCLMGDIKMSLQVETDIVDEAAMMGAAAPNFVHGHDAS

HLILTVCELVDKGVTSIAVIHDSFGTHADNTLTLRVALKGQMVAMYIDG

NALQKLLEEHEVRWMVDTGIEVPEQGEFDLNEIMDSEYVFA.
```

An SP6 RNA polymerase suitable for the present invention can be any enzyme having substantially the same polymerase activity as bacteriophage SP6 RNA polymerase. Thus, in some embodiments, an SP6 RNA polymerase suitable for the present invention may be modified from SEQ ID NO: 1. For example, a suitable SP6 RNA polymerase may contain one or more amino acid substitutions, deletions, or additions. In some embodiments, a suitable SP6 RNA polymerase has an amino acid sequence about 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, or 60% identical or homologous to SEQ ID NO: 1. In some embodiments, a suitable SP6 RNA polymerase may be a truncated protein (from N-terminus, C-terminus, or internally) but retain the polymerase activity. In some embodiments, a suitable SP6 RNA polymerase is a fusion protein.

In some embodiments, an SP6 RNA Polymerase is encoded by a gene having the following nucleotide sequence:

```
                                            (SEQ ID NO: 2)
ATGCAAGATTTACACGCTATCCAGCTTCAATTAGAAGAAGAGATGTTTA

ATGGTGGCATTCGTCGCTTCGAAGCAGATCAACAACGCCAGATTGCAGC

AGGTAGCGAGAGCGACACAGCATGGAACCGCCGCCTGTTGTCAGAACTT

ATTGCACCTATGGCTGAAGGCATTCAGGCTTATAAAGAAGAGTACGAAG

GTAAGAAAGGTCGTGCACCTCGCGCATTGGCTTTCTTACAATGTGTAGA

AAATGAAGTTGCAGCATACATCACTATGAAAGTTGTTATGGATATGCTG

AATACGGATGCTACCCTTCAGGCTATTGCAATGAGTGTAGCAGAACGCA

TTGAAGACCAAGTGCGCTTTTCTAAGCTAGAAGGTCACGCCGCTAAATA

CTTTGAGAAGGTTAAGAAGTCACTCAAGGCTAGCCGTACTAAGTCATAT

CGTCACGCTCATAACGTAGCTGTAGTTGCTGAAAAATCAGTTGCAGAAA

AGGACGCGGACTTTGACCGTTGGGAGGCGTGGCCAAAAGAAACTCAATT

GCAGATTGGTACTACCTTGCTTGAAATCTTAGAAGGTAGCGTTTTCTAT

AATGGTGAACCTGTATTTATGCGTGCTATGCGCACTTATGGCGGAAAGA

CTATTTACTACTTACAAACTTCTGAAAGTGTAGGCCAGTGGATTAGCGC

ATTCAAAGAGCACGTAGCGCAATTAAGCCCAGCTTATGCCCCTTGCGTA

ATCCCTCCTCGTCCTTGGAGAACTCCATTTAATGGAGGGTTCCATACTG
```

-continued

```
AGAAGGTAGCTAGCCGTATCCGTCTTGTAAAAGGTAACCGTGAGCATGT

ACGCAAGTTGACTCAAAAGCAAATGCCAAAGGTTTATAAGGCTATCAAC

GCATTACAAAATACACAATGGCAAATCAACAAGGATGTATTAGCAGTTA

TTGAAGAAGTAATCCGCTTAGACCTTGGTTATGGTGTACCTTCCTTCAA

GCCACTGATTGACAAGGAGAACAAGCCAGCTAACCCGGTACCTGTTGAA

TTCCAACACCTGCGCGGTCGTGAACTGAAAGAGATGCTATCACCTGAGC

AGTGGCAACAATTCATTAACTGGAAAGGCGAATGCGCGCGCCTATATAC

CGCAGAAACTAAGCGCGGTTCAAAGTCCGCCGCCGTTGTTCGCATGGTA

GGACAGGCCCGTAAATATAGCGCCTTTGAATCCATTTACTTCGTGTACG

CAATGGATAGCCGCAGCCGTGTCTATGTGCAATCTAGCACGCTCTCTCC

GCAGTCTAACGACTTAGGTAAGGCATTACTCCGCTTTACCGAGGGACGC

CCTGTGAATGGCGTAGAAGCGCTTAAATGGTTCTGCATCAATGGTGCTA

ACCTTTGGGGATGGGACAAGAAAACTTTTGATGTGCGCGTGTCTAACGT

ATTAGATGAGGAATTCCAAGATATGTGTCGAGACATCGCCGCAGACCCT

CTCACATTCACCCAATGGGCTAAAGCTGATGCACCTTATGAATTCCTCG

CTTGGTGCTTTGAGTATGCTCAATACCTTGATTTGGTGGATGAAGGAAG

GGCCGACGAATTCCGCACTCACCTACCAGTACATCAGGACGGGTCTTGT

TCAGGCATTCAGCACTATAGTGCTATGCTTCGCGACGAAGTAGGGGCCA

AAGCTGTTAACCTGAAACCCTCCGATGCACCGCAGGATATCTATGGGGC

GGTGGCGCAAGTGGTTATCAAGAAGAATGCGCTATATATGGATGCGGAC

GATGCAACCACGTTTACTTCTGGTAGCGTCACGCTGTCCGGTACAGAAC

TGCGAGCAATGGCTAGCGCATGGGATAGTATTGGTATTACCCGTAGCTT

AACCAAAAAGCCCGTGATGACCTTGCCATATGGTTCTACTCGCTTAACT

TGCCGTGAATCTGTGATTGATTACATCGTAGACTTAGAGGAAAAAGAGG

CGCAGAAGGCAGTAGCAGAAGGGCGGACGGCAAACAAGGTACATCCTTT

TGAAGACGATCGTCAAGATTACTTGACTCCGGGCGCAGCTTACAACTAC

ATGACGGCACTAATCTGGCCTTCTATTTCTGAAGTAGTTAAGGCACCGA

TAGTAGCTATGAAGATGATACGCCAGCTTGCACGCTTTGCAGCGAAACG

TAATGAAGGCCTGATGTACACCCTGCCTACTGGCTTCATCTTAGAACAG

AAGATCATGGCAACCGAGATGCTACGCGTGCGTACCTGTCTGATGGGTG

ATATCAAGATGTCCCTTCAGGTTGAAACGGATATCGTAGATGAAGCCGC

TATGATGGGAGCAGCAGCACCTAATTTCGTACACGGTCATGACGCAAGT

CACCTTATCCTTACCGTATGTGAATTGGTAGACAAGGGCGTAACTAGTA

TCGCTGTAATCCACGACTCTTTTGGTACTCATGCAGACAACACCCTCAC

TCTTAGAGTGGCACTTAAAGGGCAGATGGTTGCAATGTATATTGATGGT

AATGCGCTTCAGAAACTACTGGAGGAGCATGAAGTGCGCTGGATGGTTG

ATACAGGTATCGAAGTACCTGAGCAAGGGGAGTTCGACCTTAACGAAAT

CATGGATTCTGAATACGTATTTGCCTAA.
```

A suitable gene encoding the SP6 RNA polymerase suitable in the present may be about 99%, 98%, 97%, 96%, 95%, 94%, 93%, 92%, 91%, 90%, 89%, 88%, 87%, 86%, 85%, 84%, 83%, 82%, 81%, or 80% identical or homologous to SEQ ID NO: 2.

An SP6 RNA polymerase suitable for the invention may be a commercially-available product, e.g., from Ambion, New England Biolabs (NEB), Promega, and Roche. The SP6 may be ordered and/or custom designed from a commercial source or a non-commercial source according to the amino acid sequence of SEQ ID NO: 1 or a variant of SEQ ID NO: 1 as described herein. The SP6 may be a standard-fidelity polymerase or may be a high-fidelity/high-efficiency/high-capacity which has been modified to promote RNA polymerase activities, e.g., mutations in the SP6 RNA polymerase gene or post-translational modifications of the SP6 RNA polymerase itself. Examples of such modified SP6 include SP6 RNA Polymerase-Plus™ from Ambion, HiScribe™ SP6 from NEB, and RiboMAX™ and Riboprobe® Systems from Promega.

In some embodiments, a suitable SP6 RNA polymerase is a fusion protein. For example, an SP6 RNA polymerase may include one or more tags to promote isolation, purification, or solubility of the enzyme. A suitable tag may be located at the N-terminus, C-terminus, and/or internally. Non-limiting examples of a suitable tag include Calmodulin-binding protein (CBP); *Fasciola hepatica* 8-kDa antigen (Fh8); FLAG tag peptide; glutathione-S-transferase (GST); Histidine tag (e.g., hexahistidine tag (His6)); maltose-binding protein (MBP); N-utilization substance (NusA); small ubiquitin related modifier (SUMO) fusion tag; Streptavidin binding peptide (STREP); Tandem affinity purification (TAP); and thioredoxin (TrxA). Other tags may be used in the present invention. These and other fusion tags have been described, e.g., Costa et al. Frontiers in Microbiology 5 (2014): 63 and in PCT/US16/57044, the contents of which are incorporated herein by reference in their entireties. In some embodiments, a His tag is located at SP6's N-terminus.

SP6 Promoter

Any promoter that can be recognized by an SP6 RNA polymerase may be used in the present invention. Typically, an SP6 promoter comprises 5' ATTTAGGTGACACTATAG-3' (SEQ ID NO: 3). Variants of the SP6 promoter have been discovered and/or created to optimize recognition and/or binding of SP6 to its promoter. Non-limiting variants include but are not limited to:

```
                               (SEQ ID NO: 4 to SEQ ID NO: 13)
5'-ATTTAGGGGACACTATAGAAGAG-3';

5'-ATTTAGGGGACACTATAGAAGG-3';

5'-ATTTAGGGGACACTATAGAAGGG-3';

5'-ATTTAGGTGACACTATAGAA-3';

5'-ATTTAGGTGACACTATAGAAGA-3';

5'-ATTTAGGTGACACTATAGAAGAG-3';

5'-ATTTAGGTGACACTATAGAAGG-3';

5'-ATTTAGGTGACACTATAGAAGGG-3';

5'-ATTTAGGTGACACTATAGAAGNG-3';
and

5'-CATACGATTTAGGTGACACTATAG-3'.
```

In addition, a suitable SP6 promoter for the present invention may be about 95%, 90%, 85%, 80% m, 75%, or 70% identical or homologous to any one of SEQ ID NO: 3 to SEQ ID NO: 13. Moreover, an SP6 promoter suitable in the present invention may include one or more additional nucleotides 5' and/or 3' to any of the promoter sequences described herein.

DNA Template

Various nucleic acid templates may be used in the present invention. Typically, DNA templates which are either entirely double-stranded or mostly single-stranded with a double-stranded SP6 promoter sequence can be used.

Linearized plasmid DNA (linearized via one or more restriction enzymes), linearized genomic DNA fragments (via restriction enzyme and/or physical means), PCR products, and/or synthetic DNA oligonucleotides can be used as templates for in vitro transcription with SP6, provided that they contain a double-stranded SP6 promoter upstream (and in the correct orientation) of the DNA sequence to be transcribed.

In some embodiments, the linearized DNA template has a blunt-end.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription;

the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer™ by ThermoFisher and OptimumGene™, which is described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, and citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Large-Scale mRNA Synthesis

The present invention relates to large-scale production of mRNA. In some embodiments, a method according to the invention synthesizes mRNA at least 100 mg, 150 mg, 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more at a single batch. As used herein, the term "batch" refers to a quantity or amount of mRNA synthesized at one time, e.g., produced according to a single manufacturing setting. A batch may refer to an amount of mRNA synthesized in one reaction that occurs via a single aliquot of enzyme and/or a single aliquot of DNA template for continuous synthesis under one set of conditions. mRNA synthesized at a single batch would not include mRNA synthesized at different times that are combined to achieve the desired amount. Generally, a reaction mixture includes SP6 RNA polymerase, a linear DNA template, and an RNA polymerase reaction buffer (which may include ribonucleotides or may require addition of ribonucleotides).

According to the present invention, 1-100 mg of SP6 polymerase is typically used per gram (g) of mRNA produced. In some embodiments, about 1-90 mg, 1-80 mg, 1-60 mg, 1-50 mg, 1-40 mg, 10-100 mg, 10-80 mg, 10-60 mg, 10-50 mg of SP6 polymerase is used per gram of mRNA produced. In some embodiments, about 5-20 mg of SP6 polymerase is used to produce about 1 gram of mRNA. In some embodiments, about 0.5 to 2 grams of SP6 polymerase is used to produce about 100 grams of mRNA. In some embodiments, about 5 to 20 grams of SP6 polymerase is used to about 1 kilogram of mRNA. In some embodiments, at least 5 mg of SP6 polymerase is used to produce at least 1 gram of mRNA. In some embodiments, at least 500 mg of SP6 polymerase is used to produce at least 100 grams of mRNA. In some embodiments, at least 5 grams of SP6 polymerase is used to produce at least 1 kilogram of mRNA. In some embodiments, about 10 mg, 20 mg, 30 mg, 40 mg, 50 mg, 60 mg, 70 mg, 80 mg, 90 mg, or 100 mg of plasmid DNA is used per gram of mRNA produced. In some embodiments, about 10-30 mg of plasmid DNA is used to produce about 1 gram of mRNA. In some embodiments, about 1 to 3 grams of plasmid DNA is used to produce about 100 grams of mRNA. In some embodiments, about 10 to 30 grams of plasmid DNA is used to about 1 kilogram of mRNA. In some embodiments, at least 10 mg of plasmid DNA is used to produce at least 1 gram of mRNA. In some embodiments, at least 1 gram of plasmid DNA is used to produce at least 100 grams of mRNA. In some embodiments, at least 10 grams of plasmid DNA is used to produce at least 1 kilogram of mRNA.

In some embodiments, the concentration of the SP6 RNA polymerase in the reaction mixture may be from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. In certain embodiments, the concentration of the SP6 RNA polymerase is from about 10 to 50 nM, 20 to 50 nM, or 30 to 50 nM. A concentration of 100 to 10000

Units/ml of the SP6 RNA polymerase may be used, as examples, concentrations of 100 to 9000 Units/ml, 100 to 8000 Units/ml, 100 to 7000 Units/ml, 100 to 6000 Units/ml, 100 to 5000 Units/ml, 100 to 1000 Units/ml, 200 to 2000 Units/ml, 500 to 1000 Units/ml, 500 to 2000 Units/ml, 500 to 3000 Units/ml, 500 to 4000 Units/ml, 500 to 5000 Units/ml, 500 to 6000 Units/ml, 1000 to 7500 Units/ml, and 2500 to 5000 Units/ml may be used.

The concentration of each ribonucleotide (e.g., ATP, UTP, GTP, and CTP) in a reaction mixture is between about 0.1 mM and about 10 mM, e.g., between about 1 mM and about 10 mM, between about 2 mM and about 10 mM, between about 3 mM and about 10 mM, between about 1 mM and about 8 mM, between about 1 mM and about 6 mM, between about 3 mM and about 10 mM, between about 3 mM and about 8 mM, between about 3 mM and about 6 mM, between about 4 mM and about 5 mM. In some embodiments, each ribonucleotide is at about 5 mM in a reaction mixture. In some embodiments, the total concentration of rNTPs (for example, ATP, GTP, CTP and UTPs combined) used in the reaction range between 1 mM and 40 mM. In some embodiments, the total concentration of rNTPs (for example, ATP, GTP, CTP and UTPs combined) used in the reaction range between 1 mM and 30 mM, or between 1 mM and 28 mM, or between 1 mM to 25 mM, or between 1 mM and 20 mM. In some embodiments, the total rNTPs concentration is less than 30 mM. In some embodiments, the total rNTPs concentration is less than 25 mM. In some embodiments, the total rNTPs concentration is less than 20 mM. In some embodiments, the total rNTPs concentration is less than 15 mM. In some embodiments, the total rNTPs concentration is less than 10 mM.

The RNA polymerase reaction buffer typically includes a salt/buffering agent, e.g., Tris, HEPES, ammonium sulfate, sodium bicarbonate, sodium citrate, sodium acetate, potassium phosphate sodium phosphate, sodium chloride, and magnesium chloride.

The pH of the reaction mixture may be between about 6 to 8.5, from 6.5 to 8.0, from 7.0 to 7.5, and in some embodiments, the pH is 7.5.

Linear or linearized DNA template (e.g., as described above and in an amount/concentration sufficient to provide a desired amount of RNA), the RNA polymerase reaction buffer, and SP6 RNA polymerase are combined to form the reaction mixture. The reaction mixture is incubated at between about 37° C. and about 42° C. for thirty minutes to six hours, e.g., about sixty to about ninety minutes.

In some embodiments, about 5 mM NTPs, about 0.05 mg/mL SP6 polymerase, and about 0.1 mg/ml DNA template in a suitable RNA polymerase reaction buffer (final reaction mixture pH of about 7.5) is incubated at about 37° C. to about 42° C. for sixty to ninety minutes.

In some embodiments, a reaction mixture contains linearized double stranded DNA template with an SP6 polymerase-specific promoter, SP6 RNA polymerase, RNase inhibitor, pyrophosphatase, 29 mM NTPs, 10 mM DTT and a reaction buffer (when at 10× is 800 mM HEPES, 20 mM spermidine, 250 mM $MgCl_2$, pH 7.7) and quantity sufficient (QS) to a desired reaction volume with RNase-free water; this reaction mixture is then incubated at 37° C. for 60 minutes. The polymerase reaction is then quenched by addition of DNase I and a DNase I buffer (when at 10× is 100 mM Tris-HCl, 5 mM $MgCl_2$ and 25 mM $CaCl_2$, pH 7.6) to facilitate digestion of the double-stranded DNA template in preparation for purification. This embodiment has been shown to be sufficient to produce 100 grams of mRNA.

In some embodiments, a reaction mixture includes NTPs at a concentration ranging from 1-10 mM, DNA template at a concentration ranging from 0.01-0.5 mg/ml, and SP6 RNA polymerase at a concentration ranging from 0.01-0.1 mg/ml, e.g., the reaction mixture comprises NTPs at a concentration of 5 mM, the DNA template at a concentration of 0.1 mg/ml, and the SP6 RNA polymerase at a concentration of 0.05 mg/ml.

Nucleotides

Various naturally-occurring or modified nucleosides may be used to product mRNA according to the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("ψU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Synthesized mRNA

The present invention provides high quality in vitro synthesized mRNA. For example, the present invention provides uniformity/homogeneity of synthesized mRNA. In particular, a composition of the present invention includes a plurality of mRNA molecules which are substantially full-length. For example, at least 81%, 82%, 83%, 84%, 85%, 86%, 87%, 88%, 89%, 90%, 91%, 92%, 93%, 94%, 95%, 96%, 97%, 98%, 99%, of the mRNA molecules are full-length mRNA molecules. Such a composition is said to be "enriched" for full-length mRNA molecules. In some embodiments, mRNA synthesized according to the present invention is substantially full-length. A composition of the present invention has a greater percentage of full-length mRNA molecules than a composition that is not enriched for full-length mRNA molecules, e.g., a composition including mRNA synthesized using T7 or T3 RNA Polymerase.

In some embodiments of the present invention, a composition or a batch is prepared without a step of specifically removing mRNA molecules that are not full-length mRNA molecules (i.e., abortive or aborted transcripts).

In some embodiments, the mRNA molecules synthesized by the present invention are greater than 500, 600, 700, 800, 900, 1000, 2000, 3000, 4000, 5000, 10,000, or more nucleotides in length; also included in the present invention is mRNA having any length in between.

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

Purification of mRNA mRNA synthesized according to the present invention may be used without further purification. In particular, mRNA synthesized according to the present invention may be used without a step of removing shortmers. In some embodiments, mRNA synthesized according to the present invention may be further purified. Various methods may be used to purify mRNA synthesized according to the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol: chloroform: isoamyl alcohol solution, well known to one of skill in the art. In some embodiments, the mRNA is purified using Tangential Flow Filtration. Suitable purification methods include those described in US 2016/0040154, US 2015/0376220, PCT application PCT/US18/19954 entitled "METHODS FOR PURIFICATION OF MESSENGER RNA" filed on Feb. 27, 2018, and PCT application PCT/US18/19978 entitled "METHODS FOR PURIFICATION OF MESSENGER RNA" filed on Feb. 27, 2018, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing.

In some embodiments, the mRNA is purified either before or after or both before and after capping and tailing, by centrifugation.

In some embodiments, the mRNA is purified either before or after or both before and after capping and tailing, by filtration.

In some embodiments, the mRNA is purified either before or after or both before and after capping and tailing, by Tangential Flow Filtration (TFF).

In some embodiments, the mRNA is purified either before or after or both before and after capping and tailing by chromatography.

Characterization of mRNA

Full-length or abortive transcripts of mRNA may be detected and quantified using any methods available in the art. In some embodiments, the synthesized mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention. In some embodiments, the synthesized mRNA molecules are detected using UV absorption spectroscopy with separation by capillary electrophoresis. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

In some embodiments, mRNA generated by the method disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full-length mRNA. The impurities include IVT contaminants, e.g., proteins, enzymes, free nucleotides and/or shortmers.

In some embodiments, mRNA produced according to the invention is substantially free of shortmers or abortive transcripts. In particular, mRNA produced according to the invention contains undetectable level of shortmers or abortive transcripts by capillary electrophoresis or Glyoxal gel electrophoresis. As used herein, the term "shortmers" or "abortive transcripts" refers to any transcripts that are less than full-length. In some embodiments, "shortmers" or "abortive transcripts" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail.

Protein Expression mRNA synthesized according to the present invention results in more efficient protein translation. In some embodiments, mRNA synthesized according to the present invention results in an increased protein expression once transfected into cells, e.g., by at least 2-fold, 3-fold, 4-fold, 5-fold, 10-fold, 20-fold, 30-fold, 40-fold, 50-fold, 100-fold, 500-fold, 1000-fold, or more, relative to the same amount of mRNA synthesized using T7 or T3 RNA Polymerase.

In some embodiments, mRNA synthesized according to the present invention results in an increased protein activity encoded by the mRNA once transfected into cells, e.g., by at least 2-fold, 3-fold, 4-fold, 5-fold, 10-fold, 20-fold, 30-fold, 40-fold, 50-fold, 100-fold, 500-fold, 1000-fold, or more, relative to the same amount of mRNA synthesized using T7 or T3 RNA Polymerase.

Any mRNA may be synthesized using the present invention. In some embodiments, an mRNA encodes one or more naturally occurring peptides. In some embodiments, an mRNA encodes one or more modified or non-natural peptides.

In some embodiments an mRNA encodes an intracellular protein. In some embodiments, an mRNA encodes a cytosolic protein. In some embodiments, an mRNA encodes a protein associated with the actin cytoskeleton. In some embodiments, an mRNA encodes a protein associated with the plasma membrane. In some specific embodiments, an mRNA encodes a transmembrane protein. In some specific embodiments an mRNA encodes an ion channel protein. In some embodiments, an mRNA encodes a perinuclear protein. In some embodiments, an mRNA encodes a nuclear protein. In some specific embodiments, an mRNA encodes a transcription factor. In some embodiments, an mRNA encodes a chaperone protein. In some embodiments, an mRNA encodes an intracellular enzyme (e.g., mRNA encoding an enzyme associated with urea cycle or lysosomal storage metabolic disorders). In some embodiments, an mRNA encodes a protein involved in cellular metabolism, DNA repair, transcription and/or translation. In some embodiments, an mRNA encodes an extracellular protein. In some embodiments, an mRNA encodes a protein associated with the extracellular matrix. In some embodiments an mRNA encodes a secreted protein. In specific embodiments, an mRNA used in the composition and methods of the invention may be used to express functional proteins or enzymes that are excreted or secreted by one or more target cells into the surrounding extracellular fluid (e.g., mRNA encoding hormones and/or neurotransmitters).

The present invention provides methods for producing a therapeutic composition enriched with full-length mRNA molecules encoding a peptide or polypeptide of interest for use in the delivery to or treatment of a subject, e.g., a human subject or a cell of a human subject or a cell that is treated and delivered to a human subject.

Accordingly, in certain embodiments the present invention provides a method for producing a therapeutic composition enriched with full-length mRNA that encodes a peptide or polypeptide for use in the delivery to or treatment of the lung of a subject or a lung cell. In certain embodiments the present invention provides a method for producing a therapeutic composition enriched with full-length mRNA that encodes for cystic fibrosis transmembrane conductance regulator (CFTR) protein. In certain embodiments the present invention provides a method for producing a therapeutic composition enriched with full-length mRNA that encodes for ATP-binding cassette sub-family A member 3 protein. In certain embodiments the present invention provides a method for producing a therapeutic composition enriched with full-length mRNA that encodes for dynein axonemal intermediate chain 1 protein. In certain embodiments the present invention provides a method for producing a therapeutic composition enriched with full-length mRNA that encodes for dynein axonemal heavy chain 5 (DNAH5) protein. In certain embodiments the present invention provides a method for producing a therapeutic composition enriched with full-length mRNA that encodes for alpha-1-antitrypsin protein. In certain embodiments the present invention provides a method for producing a therapeutic composition enriched with full-length mRNA that encodes for forkhead box P3 (FOXP3) protein. In certain embodiments the present invention provides a method for producing a therapeutic composition enriched with full-length mRNA that encodes one or more surfactant protein, e.g., one or more of surfactant A protein, surfactant B protein, surfactant C protein, and surfactant D protein.

In certain embodiments the present invention provides a method for producing a therapeutic composition enriched with full-length mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition enriched with full-length mRNA that encodes for a protein associated with a urea cycle disorder. In certain embodiments the present invention provides a method for producing a therapeutic composition enriched with full-length mRNA that encodes for ornithine transcarbamylase (OTC) protein. In certain embodiments the present invention provides a method for producing a therapeutic composition enriched with full-length mRNA that encodes for arginosuccinate synthetase 1 protein. In certain embodiments the present invention provides a method for producing a therapeutic composition enriched with full-length mRNA that encodes for carbamoyl phosphate synthetase I protein. In certain embodiments the present invention provides a method for producing a therapeutic composition enriched with full-length mRNA that encodes for arginosuccinate lyase protein. In certain embodiments the present invention provides a method for producing a therapeutic composition enriched with full-length mRNA that encodes for arginase protein.

In certain embodiments the present invention provides a method for producing a therapeutic composition enriched with full-length mRNA that encodes for a protein associated with a lysosomal storage disorder. In certain embodiments the present invention provides a method for producing a therapeutic composition enriched with full-length mRNA that encodes for alpha galactosidase protein. In certain embodiments the present invention provides a method for producing a therapeutic composition enriched with full-length mRNA that encodes for glucocerebrosidase protein. In certain embodiments the present invention provides a method for producing a therapeutic composition enriched with full-length mRNA that encodes for iduronate-2-sulfatase protein. In certain embodiments the present invention provides a method for producing a therapeutic composition enriched with full-length mRNA that encodes for iduronidase protein. In certain embodiments the present invention provides a method for producing a therapeutic composition enriched with full-length mRNA that encodes for N-acetyl-alpha-D-glucosaminidase protein. In certain embodiments the present invention provides a method for producing a therapeutic composition enriched with full-length mRNA that encodes for heparan N-sulfatase protein. In certain embodiments the present invention provides a method for producing a therapeutic composition enriched with full-length mRNA that encodes for galactosamine-6 sulfatase protein. In certain embodiments the present invention provides a method for producing a therapeutic composition enriched with full-length mRNA that encodes for beta-galactosidase protein. In certain embodiments the present invention provides a method for producing a therapeutic composition enriched with full-length mRNA that encodes for lysosomal lipase protein. In certain embodiments the present invention provides a method for producing a therapeutic composition enriched with full-length mRNA that encodes for arylsulfatase B (N-acetylgalactosamine-4-sulfatase) protein. In certain embodiments the present invention provides a method for producing a therapeutic composition enriched with full-length mRNA that encodes for transcription factor EB (TFEB).

In certain embodiments the present invention provides a method for producing a therapeutic composition enriched with full-length mRNA that encodes for a protein associated with a glycogen storage disorder. In certain embodiments the present invention provides a method for producing a therapeutic composition enriched with full-length mRNA that encodes for acid alpha-glucosidase protein. In certain embodiments the present invention provides a method for producing a therapeutic composition enriched with full-length mRNA that encodes for glucose-6-phosphatase (G6PC) protein. In certain embodiments the present invention provides a method for producing a therapeutic composition enriched with full-length mRNA that encodes for liver glycogen phosphorylase protein. In certain embodiments the present invention provides a method for producing a therapeutic composition enriched with full-length mRNA that encodes for muscle phosphoglycerate mutase protein. In certain embodiments the present invention provides a method for producing a therapeutic composition enriched with full-length mRNA that encodes for glycogen debranching enzyme.

In certain embodiments the present invention provides a method for producing a therapeutic composition enriched with full-length mRNA that encodes for a protein associated with amino acid metabolism. In certain embodiments the present invention provides a method for producing a therapeutic composition enriched with full-length mRNA that encodes for phenylalanine hydroxylase enzyme. In certain embodiments the present invention provides a method for producing a therapeutic composition enriched with full-length mRNA that encodes for glutaryl-CoA dehydrogenase enzyme. In certain embodiments the present invention provides a method for producing a therapeutic composition enriched with full-length mRNA that encodes for propionyl-CoA caboxylase enzyme. In certain embodiments the present invention provides a method for producing a therapeutic composition enriched with full-length mRNA that encodes for oxalase alanine-glyoxylate aminotransferase enzyme.

In certain embodiments the present invention provides a method for producing a therapeutic composition enriched with full-length mRNA that encodes for a protein associated with a lipid metabolism or fibrotic disorder. In certain embodiments the present invention provides a method for producing a therapeutic composition enriched with full-length mRNA that encodes for a mTOR inhibitor. In certain embodiments the present invention provides a method for producing a therapeutic composition enriched with full-length mRNA that encodes for ATPase phospholipid transporting 8B1 (ATP8B1) protein. In certain embodiments the present invention provides a method for producing a therapeutic composition enriched with full-length mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition enriched with full-length mRNA that encodes for PPAR-gamma protein or an active variant.

In certain embodiments the present invention provides a method for producing a therapeutic composition enriched with full-length mRNA that encodes for a protein associated with methylmalonic acidemia. For example, in certain embodiments the present invention provides a method for producing a therapeutic composition enriched with full-length mRNA that encodes for methylmalonyl CoA mutase protein. In certain embodiments the present invention provides a method for producing a therapeutic composition enriched with full-length mRNA that encodes for methylmalonyl CoA epimerase protein.

In certain embodiments the present invention provides a method for producing a therapeutic composition enriched with full-length mRNA for which delivery to or treatment of the liver can provide therapeutic benefit. In certain embodiments the present invention provides a method for producing a therapeutic composition enriched with full-length mRNA that encodes for ATP7B protein, also known as Wilson disease protein. In certain embodiments the present invention provides a method for producing a therapeutic composition enriched with full-length mRNA that encodes for porphobilinogen deaminase enzyme. In certain embodiments the present invention provides a method for producing a therapeutic composition enriched with full-length mRNA that encodes for one or clotting enzymes, such as Factor VIII, Factor IX, Factor VII, and Factor X. In certain embodiments the present invention provides a method for producing a therapeutic composition enriched with full-length mRNA that encodes for human hemochromatosis (HFE) protein.

In certain embodiments the present invention provides a method for producing a therapeutic composition enriched with full-length mRNA that encodes a peptide or polypeptide for use in the delivery to or treatment of the cardiovasculature of a subject or a cardiovascular cell. In certain embodiments the present invention provides a method for producing a therapeutic composition enriched with full-length mRNA that encodes for vascular endothelial growth factor A protein. In certain embodiments the present invention provides a method for producing a therapeutic composition enriched with full-length mRNA that encodes for relaxin protein. In certain embodiments the present invention provides a method for producing a therapeutic composition enriched with full-length mRNA that encodes for bone morphogenetic protein-9 protein. In certain embodiments the present invention provides a method for producing a therapeutic composition enriched with full-length mRNA that encodes for bone morphogenetic protein-2 receptor protein.

In certain embodiments the present invention provides a method for producing a therapeutic composition enriched with full-length mRNA that encodes a peptide or polypeptide for use in the delivery to or treatment of the muscle of a subject or a muscle cell. In certain embodiments the present invention provides a method for producing a therapeutic composition enriched with full-length mRNA that encodes for dystrophin protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes a peptide or polypeptide for use in the delivery to or treatment of the cardiac muscle of a subject or a cardiac muscle cell. In certain embodiments the present invention provides a method for producing a therapeutic composition enriched with full-length mRNA that encodes for a protein that modulates one or both of a potassium channel and a sodium channel in muscle tissue or in a muscle cell. In certain embodiments the present invention provides a method for producing a therapeutic composition enriched with full-length mRNA that encodes for a protein that modulates a Kv7.1 channel in muscle tissue or in a muscle cell. In certain embodiments the present invention provides a method for producing a therapeutic composition enriched with full-length mRNA that encodes for a protein that modulates a Nav1.5 channel in muscle tissue or in a muscle cell.

In certain embodiments the present invention provides a method for producing a therapeutic composition enriched with full-length mRNA that encodes a peptide or polypeptide for use in the delivery to or treatment of the nervous system of a subject or a nervous system cell. For example, in certain embodiments the present invention provides a method for producing a therapeutic composition enriched with full-length mRNA that encodes for survival motor neuron 1 protein. For example, in certain embodiments the present invention provides a method for producing a therapeutic composition enriched with full-length mRNA that encodes for survival motor neuron 2 protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes for ATP binding cassette sub-family D member 1 (ABCD1) protein. In certain embodiments the present invention provides a method for producing a therapeutic composition enriched with full-length mRNA that encodes for CLN3 protein.

In certain embodiments the present invention provides a method for producing a therapeutic composition enriched with full-length mRNA that encodes a peptide or polypeptide for use in the delivery to or treatment of the blood or bone marrow of a subject or a blood or bone marrow cell. In certain embodiments the present invention provides a method for producing a therapeutic composition enriched with full-length mRNA that encodes for beta globin protein. In certain embodiments the present invention provides a method for producing a therapeutic composition enriched with full-length mRNA that encodes for Bruton's tyrosine kinase protein. In certain embodiments the present invention provides a method for producing a therapeutic composition enriched with full-length mRNA that encodes for one or clotting enzymes, such as Factor VIII, Factor IX, Factor VII, and Factor X.

In certain embodiments the present invention provides a method for producing a therapeutic composition enriched with full-length mRNA that encodes a peptide or polypeptide for use in the delivery to or treatment of the kidney of a subject or a kidney cell. In certain embodiments the present invention provides a method for producing a therapeutic composition enriched with full-length mRNA that encodes for collagen type IV alpha 5 chain (COL4A5) protein.

In certain embodiments the present invention provides a method for producing a therapeutic composition enriched with full-length mRNA that encodes a peptide or polypeptide for use in the delivery to or treatment of the eye of a subject or an eye cell. In certain embodiments the present invention provides a method for producing a therapeutic composition enriched with full-length mRNA that encodes for ATP-binding cassette sub-family A member 4 (ABCA4) protein. In certain embodiments the present invention provides a method for producing a therapeutic composition enriched with full-length mRNA that encodes for retinoschisin protein. In certain embodiments the present invention provides a method for producing a therapeutic composition enriched with full-length mRNA that encodes for retinal pigment epithelium-specific 65 kDa (RPE65) protein. In certain embodiments the present invention provides a method for producing a therapeutic composition enriched with full-length mRNA that encodes for centrosomal protein of 290 kDa (CEP290).

In certain embodiments the present invention provides a method for producing a therapeutic composition enriched with full-length mRNA that encodes a peptide or polypeptide for use in the delivery of or treatment with a vaccine for a subject or a cell of a subject. For example, in certain embodiments the present invention provides a method for producing a therapeutic composition enriched with full-length mRNA that encodes for an antigen from an infectious agent, such as a virus. In certain embodiments the present invention provides a method for producing a therapeutic composition enriched with full-length mRNA that encodes for an antigen from influenza virus. In certain embodiments the present invention provides a method for producing a therapeutic composition enriched with full-length mRNA that encodes for an antigen from respiratory syncytial virus. In certain embodiments the present invention provides a method for producing a therapeutic composition enriched with full-length mRNA that encodes for an antigen from rabies virus. In certain embodiments the present invention provides a method for producing a therapeutic composition enriched with full-length mRNA that encodes for an antigen from cytomegalovirus. In certain embodiments the present invention provides a method for producing a therapeutic composition enriched with full-length mRNA that encodes for an antigen from rotavirus. In certain embodiments the present invention provides a method for producing a therapeutic composition enriched with full-length mRNA that encodes for an antigen from a hepatitis virus, such as hepatitis A virus, hepatitis B virus, or hepatis C virus. In certain embodiments the present invention provides a method for producing a therapeutic composition enriched with full-length mRNA that encodes for an antigen from human papillomavirus. In certain embodiments the present invention provides a method for producing a therapeutic composition enriched with full-length mRNA that encodes for an antigen from a herpes simplex virus, such as herpes simplex virus 1 or herpes simplex virus 2. In certain embodiments the present invention provides a method for producing a therapeutic composition enriched with full-length mRNA that encodes for an antigen from a human immunodeficiency virus, such as human immunodeficiency virus type 1 or human immunodeficiency virus type 2. In certain embodiments the present invention provides a method for producing a therapeutic composition enriched with full-length mRNA that encodes for an antigen from a human metapneumovirus. In certain embodiments the present invention provides a method for producing a therapeutic composition enriched with full-length mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition enriched with full-length mRNA that encodes for an antigen from malaria virus. In certain embodiments the present invention provides a method for producing a therapeutic composition enriched with full-length mRNA that encodes for an antigen from zika virus. In certain embodiments the present invention provides a method for producing a therapeutic composition enriched with full-length mRNA that encodes for an antigen from chikungunya virus.

In certain embodiments the present invention provides a method for producing a therapeutic composition enriched with full-length mRNA that encodes for an antigen associated with a cancer of a subject or identified from a cancer cell of a subject. In certain embodiments the present invention provides a method for producing a therapeutic composition enriched with full-length mRNA that encodes for an antigen determined from a subject's own cancer cell, i.e., to provide a personalized cancer vaccine. In certain embodiments the present invention provides a method for producing a therapeutic composition enriched with full-length mRNA that encodes for an antigen expressed from a mutant KRAS gene.

In certain embodiments the present invention provides a method for producing a therapeutic composition enriched with full-length mRNA that encodes for an antibody. In certain embodiments, the antibody can be a bi-specific antibody. In certain embodiments, the antibody can be part of a fusion protein. In certain embodiments the present invention provides a method for producing a therapeutic composition enriched with full-length mRNA that encodes for an antibody to OX40. In certain embodiments the present invention provides a method for producing a therapeutic composition enriched with full-length mRNA that encodes for an antibody to VEGF. In certain embodiments the present invention provides a method for producing a therapeutic composition enriched with full-length mRNA that encodes for an antibody to tissue necrosis factor alpha. In certain embodiments the present invention provides a method for producing a therapeutic composition enriched with full-length mRNA that encodes for an antibody to CD3. In certain embodiments the present invention provides a method for producing a therapeutic composition enriched with full-length mRNA that encodes for an antibody to CD19.

In certain embodiments the present invention provides a method for producing a therapeutic composition enriched with full-length mRNA that encodes for an immunomodulator. In certain embodiments the present invention provides a method for producing a therapeutic composition enriched with full-length mRNA that encodes for Interleukin 12. In certain embodiments the present invention provides a method for producing a therapeutic composition enriched with full-length mRNA that encodes for Interleukin 23. In certain embodiments the present invention provides a method for producing a therapeutic composition enriched with full-length mRNA that encodes for Interleukin 36 gamma. In certain embodiments the present invention provides a method for producing a therapeutic composition enriched with full-length mRNA that encodes for a constitutively active variant of one or more stimulator of interferon genes (STING) proteins.

In certain embodiments the present invention provides a method for producing a therapeutic composition enriched with full-length mRNA that encodes for an endonuclease. In certain embodiments the present invention provides a method for producing a therapeutic composition enriched with full-length mRNA that encodes for an RNA-guided DNA endonuclease protein, such as Cas 9 protein. In certain embodiments the present invention provides a method for producing a therapeutic composition enriched with full-length mRNA that encodes for a meganuclease protein. In certain embodiments the present invention provides a method for producing a therapeutic composition enriched with full-length mRNA that encodes for a transcription activator-like effector nuclease protein. In certain embodiments the present invention provides a method for producing a therapeutic composition enriched with full-length mRNA that encodes for a zinc finger nuclease protein.

Lipid Nanoparticles mRNA synthesized according to the present invention may be formulated and delivered for in vivo protein production using any method. In some embodiments, mRNA is encapsulated, into a transfer vehicle, such as a nanoparticle. Among other things, one purpose of such encapsulation is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue. In some embodiments, nanoparticles may be lipid-based nanoparticles, e.g., comprising a liposome, or polymer-based nanoparticles. In some embodiments, a nanoparticle may have a diameter of less than about 40-100 nm. A nanoparticle may include at least 1 µg, 10 µg, 100 µg, 1 mg, 10 mg, 100 mg, 1 g, or more mRNA.

In some embodiments, the transfer vehicle is a liposomal vesicle, or other means to facilitate the transfer of a nucleic acid to target cells and tissues. Suitable transfer vehicles include, but are not limited to, liposomes, nanoliposomes, ceramide-containing nanoliposomes, proteoliposomes, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

A liposome may include one or more cationic lipids, one or more non-cationic lipids, one or more sterol-based lipids, and/or one or more PEG-modified lipids. A liposome may include three or more distinct components of lipids, one distinct component of lipids being sterol-based cationic lipids. In some embodiments, the sterol-based cationic lipid is an imidazole cholesterol ester or "ICE" lipid (see, WO 2011/068810, which is incorporated by reference in its entirety). In some embodiments, sterol-based cationic lipids constitute no more than 70% (e.g., no more than 65% and 60%) of the total lipids in a lipid nanoparticle (e.g., liposome).

Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides).

Non-limiting examples of cationic lipids include C12-200, MC3, DLinDMA, DLinkC2DMA, cKK-E12, ICE (Imidazole-based), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, and HGT4003, or a combination thereof.

Non-limiting examples of non-cationic lipids include ceramide; cephalin; cerebrosides; diacylglycerols; 1,2-dipalmitoyl-sn-glycero-3-phosphorylglycerol sodium salt (DPPG); 1,2-distearoyl-sn-glycero-3-phosphoethanolamine (DSPE); 1,2-distearoyl-sn-glycero-3-phosphocholine (DSPC); 1,2-dipalmitoyl-sn-glycero-3-phosphocholine (DPPC); 1,2-dioleyl-sn-glycero-3-phosphoethanolamine (DOPE); 1,2-dioleyl-sn-glycero-3-phosphotidylcholine (DOPC); 1,2-dipalmitoyl-sn-glycero-3-phosphoethanolamine (DPPE); 1,2-dimyristoyl-sn-glycero-3-phosphoethanolamine (DMPE); and 1,2-dioleoyl-sn-glycero-3-phospho-(1'-rac-glycerol) (DOPG), 1-palmitoyl-2-oleoyl-phosphatidyletha-nolamine (POPE); 1-palmitoyl-2-oleoyl-sn-glycero-3-phos-phocholine (POPC); 1-stearoyl-2-oleoyl-phosphatidylethanolamine (SOPE); sphingomyelin; or a combination thereof.

In some embodiments, a PEG-modified lipid may be a poly(ethylene) glycol chain of up to 5 kDa in length covalently attached to a lipid with alkyl chain(s) of C6-C20 length. Non-limiting examples of PEG-modified lipids include DMG-PEG, DMG-PEG2K, C8-PEG, DOG PEG, ceramide PEG, and DSPE-PEG, or a combination thereof.

Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. A polymer-based nanoparticles may include polyethylenimine (PEI), e.g., a branched PEI.

Additional teaching relevant to the present invention are described in one or more of the following: WO 2011/068810, WO 2012/075040, U.S. Ser. No. 15/294,249, U.S. 62/420,421, and U.S. 62/421,021, and the related applications filed Feb. 27, 2017 by Applicants entitled "METHODS FOR PURIFICATION OF MESSENGER RNA", "NOVEL CODON-OPTIMIZED CFTR SEQUENCE", and "METHODS FOR PURIFICATION OF MESSENGER RNA", each of which is incorporated by reference in its entirety.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

EXAMPLES

Example 1: Exemplary Experimental Design for mRNA Synthesis Using SP6 RNA Polymerase and Characterization This example illustrates exemplary conditions for SP6 polymerase based mRNA synthesis, transfection, and characterization of the same.

Messenger RNA Material

Firefly Luciferase (FFL), human erythropoietin (EPO), human Phenylalanine Hydroxylase (PAH), human Cystic Fibrosis Transmembrane Conductance Regulator (CFTR), Arginosuccinate Synthase (ASS1), and Ornithine Trans Carbamylase (OTC) were synthesized by in vitro transcription from plasmid DNA encoding the corresponding gene. The T7 transcription reaction consisted of 1×T7 transcription buffer (80 mM HEPES pH 8.0, 2 mM Spermidine, and 25 mM $MgCl_2$ with a final pH of 7.7), 10 mM DTT, 7.25 mM each ATP, GTP, CTP, and UTP, RNAse Inhibitor, Pyrophosphatase, and T7 Polymerase. The SP6 reaction included 5 mM of each NTP, about 0.05 mg/mL SP6 polymerase DNA, and about 0.1 mg/mL template DNA; other components of transcription buffer varied. The reactions were performed for 60 to 90 minutes (unless otherwise noted) at 37 C. DNAseI was added to stop the reaction and incubated for 15 more minutes at 37° C. The in vitro transcribed mRNA was purified using the Qiagen RNA maxi column following manufacturer's recommendations. The purified mRNA product from the aforementioned in vitro transcription step was treated with portions of GTP (1.0 mM), S-adenosyl methionine, RNAse inhibitor, 2'-O-Methyltransferase and guanylyl transferase are mixed together with reaction buffer (10×, 500 mM Tris-HCl (pH 8.0), 60 mM KCl, 12.5 mM $MgCl_2$). The combined solution was incubated for a range of time at 37° C. for 30 to 90 minutes. Upon completion, aliquots of ATP (2.0 mM), PolyA Polymerase and tailing reaction buffer (10×, 500 mM Tris-HCl (pH 8.0), 2.5 M NaCl, 100 mM $MgCl_2$) were added and the total reaction mixture was further incubated at 37° C. for a range of time from 20 to 45 minutes. Upon completion, the final reaction mixture was quenched and purified accordingly.

The IVT reaction is scaled up in the following manner: Briefly, for each gram of mRNA transcribed, a reaction containing 20 mg of a linearized double stranded DNA plasmid with an RNA polymerase-specific promoter, 10 mg RNA polymerase, RNase inhibitor, pyrophosphatase, 5 mM NTPs, 10 mM DTT and a reaction buffer (10×-250 mM Tris-HCl, pH 7.5, 20 mM spirmidine, 50 mM NaCl,) was used and quantity sufficient (QS) to 200 ml with RNase-free water then incubated at 37 C for 60 min. The reaction was then quenched by the addition of DNase I and a DNase I buffer (10×-100 mM Tris-HCl, 5 mM $MgCl_2$ and 25 mM $CaCl_2$, pH 7.6) to facilitate digestion of the double-stranded DNA template in preparation for purification. The final reaction volume was 226 ml. Cap and Tail (C/T') Reaction:

Purified in vitro transcribed mRNA was modified enzymatically by the addition of a 5' $N^7$-methylguanylate cap 0 structure using guanylate transferase and the addition of a methyl group at the 2' 0 position of the penultimate nucleotide resulting in a Cap 1 structure using 2' O-methyltransferase as described by (Fechter, P.; Brownlee, G. G. "Recognition of mRNA cap structures by viral and cellular proteins" *J. Gen. Virology* 2005, 86, 1239-1249). Following addition of the Cap 1 structure, a poly-adenylate tail was added to the 3' end of the in vitro transcribed mRNA enzymatically using poly-A polymerase. Briefly, a capping reaction was set up for every gram of purified IVT containing 2.5 mM GTP, 246 µM S-adenosyl methionine, RNase inhibitor, 2'-Omethyl transferase, guanylyl transferase, a reaction buffer (10×-500 mM Tris-HCl pH 8.0, 60 mM $MgCl_2$, and 12.5 mM $MgCl_2$) and QS to 650 ml with RNase-free $H_2O$ then incubated at 37 C for 60 minutes. Following the incubation, a tailing reaction was initiated by adding tailing buffer (10×-500 mM Tris-HCl pH 8.0, 2.5 M NaCl, 100 mM $MgCl_2$), 3.7 mM ATP, poly-A polymerase and QS to 800 ml with RNase-free $H_2O$. The tailing reaction was carried out at 37° C. for 30 minutes before the addition of 12.5 mM EDTA to quench.
RNA Precipitation:

Generally, for every gram of mRNA (IVT reaction, C/T reaction, or previously-purified aqueous mRNA) salt-EtOH precipitations were performed as follows. The mRNA was brought to 1 g/l using RNase-free $H_2O$ and then an equal volume of GSCN buffer containing 4M guanidine thiocynate, 25 mM sodium citrate pH 6.5 and 0.5% N-lauroylsarcosine was added. The mRNA solution was mixed thoroughly and incubated at ambient temperature for five minutes with continual mixing. An equal volume of absolute ethanol was then added to the mRNA-GSCN solution and continuously mixed for 5 minutes at ambient temperature to facilitate precipitation.
Purification Large scale preparation of mRNA is purified by the following method. 50 grams of C/T mRNA was QS to ten liters with RNase-free $H_2O$ and precipitated with equal volumes of GSCN buffer and EtOH then loaded onto the vertical filtering centrifuge through the sample feed port with centrifuge set to 3000 RPM. The RNA precipitate collected on the centrifuge filter was washed with five liters of GSCN-EtOH wash solution (57.6% GSCN and 42.4% EtOH) through the sample feed port with centrifuge running at 3000 RPM. The RNA precipitate was then de-salted with a twenty liter 80% EtOH wash through the sample feed port with centrifuge remaining at 3000 RPM. The RNA precipitate was dried for thirty minutes while spinning at 3000 RPM with all ports open to ambient conditions. The dried RNA precipitate was manually harvested from the filter membrane, sectioned into manageable pieces and stored in a 500 ml sterile bottle at −20° C. for long term storage.
Agarose Gel Electrophoresis:

1% Agarose gels were prepared using 0.5 g Agarose in 50 ml TAE buffer. 1 to 2 µg of RNA was treated with 2× Glyoxal gel loading dye or 2× Formamide gel loading dye, loaded on the Agarose gel and run at 130V for 30 or 60 minutes.
Capillary Electrophoresis:

The standard sensitivity RNA analysis kit was (15nt) was purchased from Advanced Analytical and used in capillary electrophoresis runs on the Fragment Analyzer instrument with a twelve-capillary array (Advanced Analytical). Upon gel priming, 300 ng of total RNA was mixed with diluent marker at 1:11 (RNA:Marker) ratio and 24 µL was loaded per well in a 96-well plate. The molecular weight indicator ladder was prepared by mixing 2 µl of the standard sensitivity RNA ladder with 22 µl diluent marker. Sample injection was at 5.0 kV, 4 seconds and sample separation at 8.0 kV, 40.0 min. Electropherogram of each sample was processed through the ProSize™ 2 software (Advanced Analytical), producing tabulated sizes (bp) and abundances (ng/µl) of fragments present in the sample.
Transient Transfection:

HEK293T/17 cells were passaged according to predetermined densities to prepare the cells for transfection. Cells were plated in six-well tissue culture plates and allowed to adhere to the plate surface overnight in a standard tissue culture incubator. Target mRNA was diluted then complexed together with Lipofectamine™ 2000 in OptiMEM Reduced Serum Media. Culture medium was removed and replaced with fresh OptiMEM Reduced Serum Media, and mRNA: Lipofectamine™ 2000 complexes were added to the cells. Cells were incubated overnight, OptiMEM was aspirated from the monolayer, and cells were lysed with a prepared 1× Laemmli lysis buffer to solubilize the target protein for Western analysis.
Western Blot:

HEK293T/17 cells previously transfected with target mRNA were lysed in prepared Laemmli sample buffer and lysate was collected. The lysate was briefly incubated at 42° C. then run on a Tris-Glycine gel to separate proteins by size. The proteins were transferred onto a PVDF membrane, and any nonspecific binding sites were blocked with a prepared buffer. The membrane was incubated with a specific anti-target protein antibody followed by a species specific secondary antibody. The membrane was washed, then ECL substrate was added and blot image were captured.

Silver Staining:

15.5 µl of 1 mg/ml mRNA is treated with 4 µl RNase1 (100 U/ml) for 30 min at 37° C. The Rnase 1 digested samples were resolved in 10% Bis-Tris Gel at 200V for 35 minutes. The enzymes used in the IVT reactions and post synthesis modification reactions, such as SP6 polymerase, Guanylyl Transferase, 0-Methyl Transferase, and Poly A polymerase were also loaded as electrophoretic migration controls in the gel. The residual proteins were visualized using the SilverQuest™ silver stain kit (Invitrogen).

Citrulline Assay:

The lysate was added to a mixture of carbamoylphosphate, ornithine and triethanolamine and allowed to react at 37° C. for 30 minutes. The reaction was stopped with a mixture of phosphoric and sulfuric acid. Diacetylmonoxime was added and the plate was boiled at 95° C. for 30 minutes, allowed to cool, and read at an absorbance of 490 nm against a standard curve of citrulline solution to determine activity of samples.

Example 2: SP6-Derived Transcription Products are Enriched for Full-Length Transcripts Whereas T7-Derived Transcription Products Include Abortive Transcripts This example demonstrates that mRNA products produced by SP6 polymerase synthesis are enriched for full-length transcripts, as compared to those produced by T7 polymerase synthesis. As shown here, this discovery was made when mRNA was characterized after capping and tailing.

Figure 1:
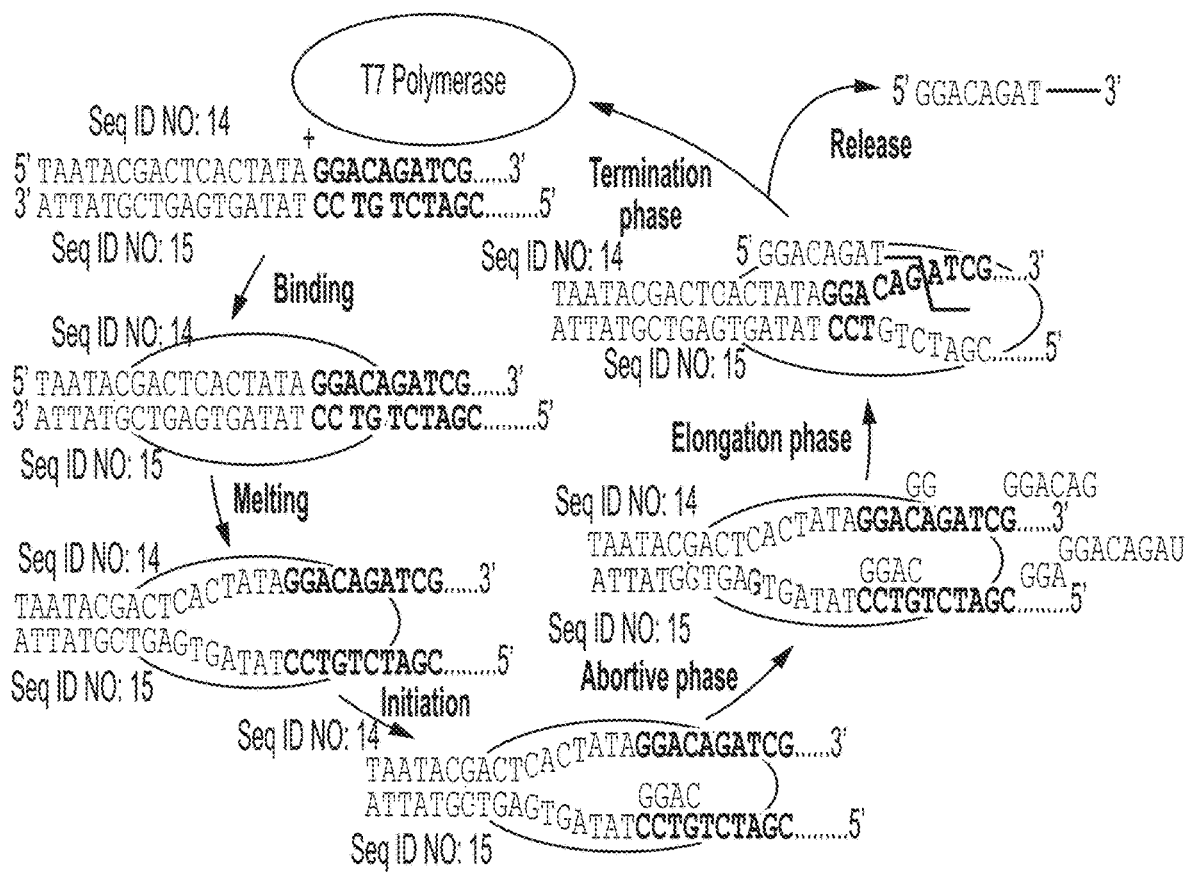
FIG. 1 is a schematic illustrating the process of transcription and including production of abortive transcripts. Here, T7 is shown as RNAP. After binding the promoter sequence, T7 undergoes a stepwise process of melting the DNA, initiation, and elongation before the enzyme is released during the termination step for a new round of transcription. Abortive transcripts are generated during the initiation phase, which is thermodynamically stable, and until the polymerase undergoes a full conformational change which forms into the elongation complex.
Figure 2:
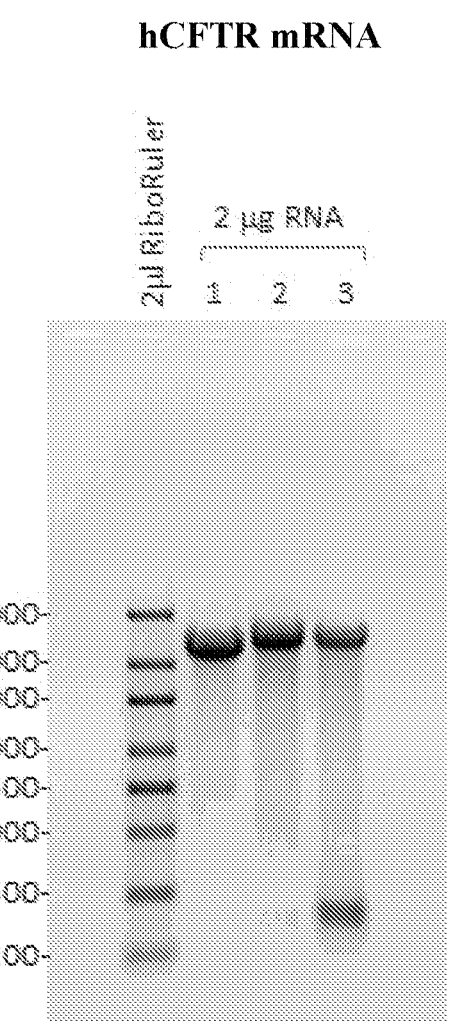
FIG. 2 is a digital image of an agarose gel of human Cystic Fibrosis Transmembrane Conductance Regulator (CFTR) RNA transcribed with SP6 versus T7 polymerase. CFTR mRNA was transcribed with SP6 or T7 polymerase and the capped and tailed (C/T) product was run on a 1% agarose gel in Glyoxal gel loading dye for 60 minutes. Lanes: lane 1, in vitro transcribed CFTR SP6 transcript; lane 2, CFTR SP6 transcript after C/T; and lane 3, CFTR T7 transcript after capping and tailing (C/T).
Figure 3:
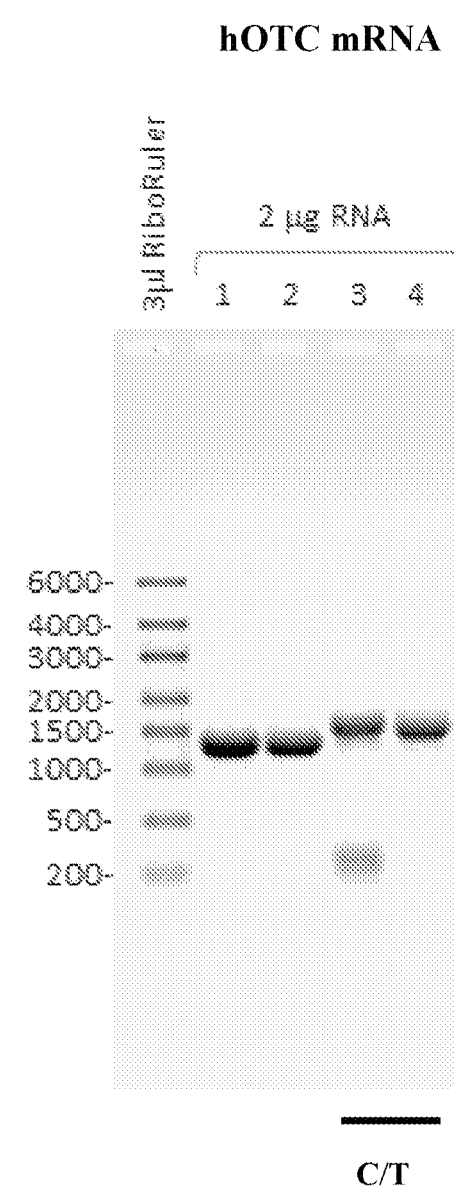
FIG. 3 is a digital image of an agarose gel of Ornithine Trans Carbamylase (OTC) mRNA transcribed with SP6 versus T7 polymerase. OTC mRNA was transcribed with SP6 or T7 polymerase and the capped and tailed product was run on a 1% agarose gel in Glyoxal gel loading dye for 60 minutes. Lanes: lane 1, OTC T7 IVT; lane 2, OTC SP6 IVT; lane 3, OTC T7 transcript after C/T; and lane 4, OTC T7 transcript after C/T.
Figure 4:
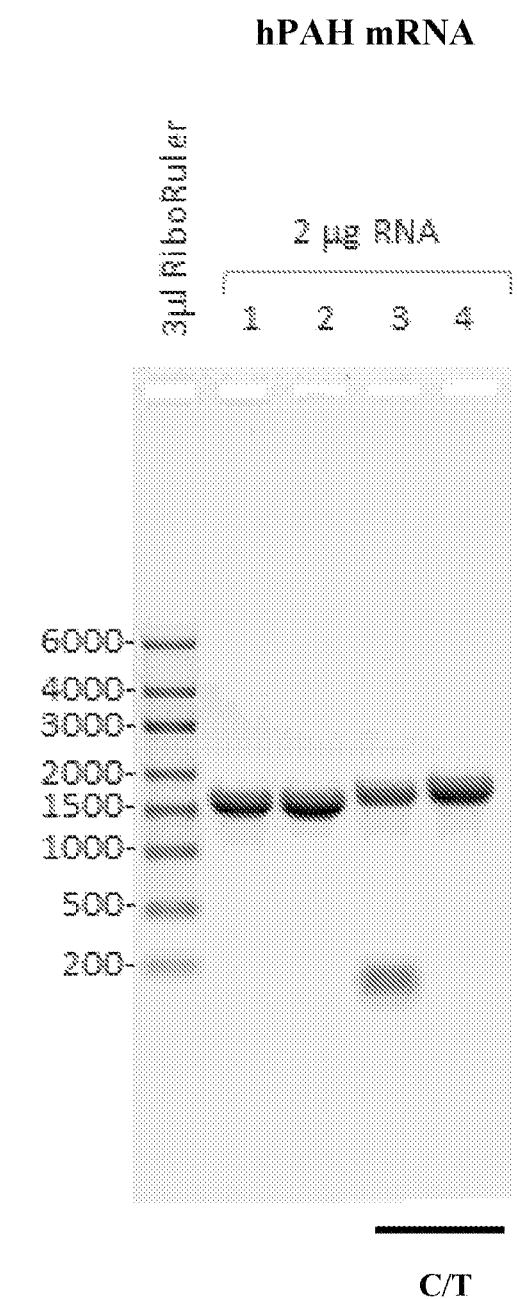
FIG. 4 is a digital image of an agarose gel of human Phenylalanine Hydroxylase (PAH) mRNA transcribed with SP6 versus T7 polymerase. PAH RNA was transcribed with SP6 or T7 polymerase and the capped and tailed product was run on a 1% agarose gel in Glyoxal gel loading dye for 60 minutes. Lanes: lane 1, PAH T7 IVT; lane 2, PAH SP6 IVT; lane 3, PAH T7 transcript after C/T; and lane 4, PAH T7 transcript after C/T.

Human Cystic Fibrosis Transmembrane Conductance Regulator (CFTR) mRNA (FIG. 2); Ornithine Trans Carbamylase (OTC) mRNA (FIG. 3); human Phenylalanine Hydroxylase (PAH) mRNA (FIG. 4); Firefly Luciferase (FFL) mRNA (FIG. 5); or human erythropoietin (EPO) mRNA (FIG. 6) was transcribed using SP6 or using T7 polymerases.

For each mRNA product detected after capping and tailing of mRNA), when T7 was used, abortive transcripts were clearly produced, whereas when SP6 was used, abortive transcripts were not detected. Upon quantitating the relative band intensities using IMAGE J analysis software, the shortmers band intensity of T7-derived CFTR mRNA preparation was found to be 20 times more intense than SP6-derived CFTR mRNA preparation (FIG. 2). Similar observations were made in case of OTC (8.47 times, FIG. 3); PAH (15.16 times, FIG. 4); EPO (7.76 times, FIG. 5); and FFL (14.95 times, FIG. 6). These results demonstrate that mRNA produced by SP6 polymerase was enriched for full-length mRNA and is substantially free of abortive transcripts.

In addition, full-length transcript yield in SP6-derived sample was relatively higher than that of T7-derived sample in each case. This is indicated by the relative band intensities of two samples in the agarose gels, since equivalent amounts of each product was loaded per lane. Importantly, the relative band intensities are proportional to the total amounts of RNA in the sample corresponding to the band. For example, relative band intensity of SP6-derived CFTR full-length transcript was 1.4 times higher than that of T7-derived sample (FIG. 2). This indicates that the full-length transcript yield of SP6-derived CFTR mRNA was approximately 1.4 times more than that of the T7-derived CFTR mRNA. Likewise, SP6-derived full-length OTC mRNA was 1.02 times higher than the T7-derived counterpart (FIG. 3); SP6-derived full-length PAH mRNA yield was 1.48 times higher than the T7-derived counterpart (FIG. 4); SP6-derived full-length EPO mRNA was 1.2 times higher than the T7-derived counterpart (FIG. 5); and SP6-derived full-length FFL mRNA was 1.36 times higher than the T7-derived counterpart (FIG. 6). A densitometric scan analysis of the agarose gels was performed on the gel electrophoresis bands. Intensities of the main bands reflecting the full-length mRNA generated using T7 polymerases and SP6 are shown in Table 1. Intensities of the shortmer bands are shown in Table 2. Comparison of main mRNA band intensities between T7 vs. SP6 is shown in FIG. 7. Comparison of shortmer mRNA band intensities between T7 vs. SP6 is shown in FIG. 8. Relative intensities comparing the main band and the shortmer band for different mRNA generated by T7 and SP6 are summarized in Table 3.

TABLE 1

Intensities of main bands corresponding to full-length mRNA

| Sample | Gray mean value[1] | Background normalized value[2] |
|---|---|---|
| T7 CFTR mRNA | 108.209 | 72.435 |
| SP6 CFTR mRNA | 139.282 | 102.294 |
| CFTR SP6/T7[3] | | 1.41 |
| T7 OTC mRNA | 85.937 | 62.209 |
| SP6 OTC mRNA | 86.295 | 63.584 |
| OTC SP6/T7[3] | | 1.02 |
| T7 PAH mRNA | 76.815 | 55.937 |
| SP6 PAH mRNA | 102.444 | 82.83 |
| PAH SP6/T7[3] | | 1.48 |
| T7 EPO mRNA | 95.546 | 71.016 |
| SP6 EPO mRNA | 112.37 | 85.865 |
| EPO SP6/T7[3] | | 1.21 |
| T7 FFL mRNA | 83.129 | 59.331 |
| SP6 FFL mRNA | 105.096 | 81.139 |
| FFL SP6/T7[3] | | 1.37 |

[1] Gray mean value corresponds to the mean densitometry measurement across the relevant gel band corresponding to full-length mRNA
[2] Background normalized value is the gray mean value minus the mean densitometry measurement of an area adjacent to the relevant gel band (i.e., minus the adjacent background intensity)
[3] Relative densitometric intensity of SP6 derived full-length mRNA band/intensity of T7 derived full-length mRNA band

TABLE 2

Intensities of low bands corresponding to shortmers with polyA tails

| Sample | Gray mean value[1] | Background normalized value[2] |
|---|---|---|
| T7 CFTR shortmer | 90.836 | 53.394 |
| SP6 CFTR shortmer | 39.076 | 2.664 |
| CFTR shortmer T7/SP6[3] | | 20.04 |
| T7 OTC shortmer | 56 | 33.656 |
| SP6 OTC shortmer | 25.2 | 3.97 |
| OTC shortmer T7/SP6[3] | | 8.48 |
| T7 PAH shortmer | 64.964 | 44.258 |
| SP6 PAH shortmer | 22.595 | 2.918 |
| PAH shortmer T7/SP6[3] | | 15.17 |
| T7 EPO shortmer | 63.307 | 36.226 |
| SP6 EPO shortmer | 30.487 | 4.664 |
| EPO shortmer T7/SP6[3] | | 7.77 |
| T7 FFL shortmer | 61.142 | 33.668 |
| SP6 FFL shortmer | 27.916 | 2.251 |
| FFL shortmer T7/SP6[3] | | 14.96 |

[1] Gray mean value corresponds to the mean densitometry measurement across the relevant gel band corresponding to shortmer mRNA
[2] Background normalized value is the gray mean value minus the mean densitometry measurement of an area adjacent to the relevant gel band (i.e., minus the adjacent background intensity)
[3] Relative densitometric intensity of T7 derived shortmer RNA band/intensity of SP6 derived shortmer mRNA band

TABLE 3

Comparing main band and shortmer band generated by T7 and SP6

|  | Main band value[1] | Shortmer band value[2] | % Shortmer[3] | Main band intensity/ Shortmer band intensity |
|---|---|---|---|---|
| CFTR T7 | 72.43 | 53.39 | 42.4% | 1.35 |
| CFTR SP6 | 102.29 | 2.66 | 2.5% | 38.45 |
| OTC T7 | 62.20 | 33.65 | 35.1% | 1.84 |
| OTC SP6 | 63.58 | 3.97 | 5.9% | 16.01 |
| PAH T7 | 55.93 | 44.25 | 44.2% | 1.26 |
| PAH SP6 | 82.83 | 2.91 | 3.4% | 28.46 |
| EPO T7 | 71.01 | 36.22 | 33.8% | 1.96 |
| EPO SP6 | 85.86 | 4.66 | 5.2% | 18.42 |
| FFL T7 | 59.33 | 33.66 | 36.2% | 1.76 |
| FFL SP6 | 81.13 | 2.25 | 2.7% | 36.05 |

[1]Main band values correspond to the Background normalized values of the main bands (corresponding to full-length mRNA) for each sample as described in Table 1 above
[2]Shortmer values correspond to the Background normalized values of the shortmer bands for each sample as described in Table 2 above
[3]% Shortmer is calculated as follows: Shortmer band value/(Main band value + Shortmer band value) × 100

Example 3: Abortive Transcripts are Detected by Glyoxal Gel Electrophoresis

This example further demonstrates that mRNA products produced by SP6 polymerase synthesis contain significantly reduced aborted sequence. In this experiment, a side-by-side comparison was visualized, as shown in FIG. 9A: using a Formamide denaturing gel and FIG. 9B: a Glyoxal denaturing gel. CFTR mRNA transcripts produced by in vitro transcription using T7 and SP6, capped and tailed, were resolved in otherwise identical agarose gels, but using either Formamide as denaturing agent in loading dye or Glyoxal as denaturing agent in loading dye, following the method described in Example 1. In addition to the full-length messenger RNA band, a faster migrating strong band of the capped and tailed short abortive mRNA transcripts was visualized at the lower part of the gel in the T7 polymerase-derived sample, and only in the Glyoxal gel and not in the Formamide gel. Such a band is absent in the SP6-derived sample in either gels.

The comparison also highlights a greater yield of full-length transcripts using SP6 polymerase compared to T7 polymerase. This is indicated by a band of greater intensity on the second lane of either gel comprising SP6-derived sample compared to the first lane comprising the T7-derived sample, where identical amounts of the products were loaded per lane.

Example 4: SP6-Derived Capped and Tailed hRS1 mRNA Products are Enriched in Full-Length mRNA In this example, codon optimized human RS1 transcripts were produced using SP6 RNA polymerase. Capped and tailed products were resolved on agarose gel with Glyoxal loading dye. As shown in FIG. 10, there are no detectable shortmer bands. Each band corresponds to the full-length transcript, and in the cases of C/T samples, the bands run exactly at the length corresponding to attached 3' poly A tail and 5' cap. The lengths of the mRNA in lanes 2, 4 and 6 are 928, 944 and 937 nucleotides. Lanes 3, 5 and 7 represent the capped and tailed species of the mRNA run in lanes 2, 4 and 6 respectively. In lane 3, with an addition of 286 nucleotides poly A tail to the mRNA of lane 2, the band runs at a length corresponding to 1214 nulceotides. In lane 5, the mRNA has an addition of 281 nucleotides of poly A tail to 944 nucleotides of the mRNA of lane 4, and in lane 7, the mRNA has an addition of 317 nucleotides of poly A tail to 944 nucleotides of the mRNA (lane 4). Most importantly, no additional bands corresponding to capped and tailed shortmers are detectable in any of the mRNA preparations.

Example 5: SP6-Derived Capped and Tailed hFXN mRNA Products are Enriched in Full-Length mRNA In this example, codon optimized human Frataxin (FXN) transcripts were produced using SP6 RNA polymerase. Capped and tailed products were resolved on agarose gel with Glyoxal loading dye. As shown in FIG. 11, there are no detectable shortmer bands. Moreover, each band correspond to the full-length transcript, without C/T (lanes 2, 4, and 6), and with C/T (lanes 3, 5, and 7). The mRNA in lane 2 is 804 nucleotides, and with the mRNA in lane 4 is 824 nucleotides, and the mRNA in lane 6 is 844 nucleotides. Lanes 3, 5 and 7 represent the capped and tailed mRNA of the samples run in lanes 2, 4 and 6 respectively. In lane 3, the mRNA of lane 2, after C/T, has a poly A tail of 527 nucleotides. In lane 5, the mRNA of lane 4 after C/T has a poly A tail 540 nucleotides long. In lane 7, the mRNA of lane 5 after C/T has a poly A tail 503 nucleotides long. Most importantly, no additional bands corresponding to capped and tailed shortmers are detectable in any of the mRNA preparations.

Example 6: SP6-Derived Transcription Products Contain Significantly Reduced Aborted Transcripts This example further demonstrates that mRNA products produced by SP6 polymerase synthesis contain significantly reduced aborted sequences.

In this experiment, capillary electrophoresis was used to characterize mRNA products synthesized using T7 versus SP6, respectively, after capping and tailing. Specifically, identical amounts of mRNA (150 ng) were loaded for capillary electrophoresis and the profiles were determined by the relative fluorescence units (RFU) obtained. As shown in FIG. 12A, the T7 polymerase-derived mRNA contains pre-aborted sequences present as the "shoulder" at the base of the peak which represents the full-length transcripts. In contrast, as shown in FIG. 12B, the SP6-derived product is substantially free of the "shoulder" indicative of prematurely aborted mRNA transcripts And instead, contains a more intense and sharper peak corresponding to the full-length product.

These data further demonstrates that the SP6 produced mRNA products are enriched for full-length mRNA with significantly reduced abortive sequences.

Example 7: SP6-Derived OTC mRNA Products are Enriched for Full-Length Transcripts Whereas T7-Derived Transcription Products Include Abortive Transcripts In this example, capillary electrophoresis was used to characterize mRNA produced by SP6 for transcribing RNA as compared to mRNA produced by T7. In this experiment, capillary electrophoresis was used with detection using fluorescence. mRNA species present in the sample before and after capping and tailing were analyzed by this molecular size based resolution and fluorescence based detection method.

FIG. 13A to FIG. 13D relate to OTC mRNA, FIG. 14A to FIG. 14D relate to PAH, FIG. 15A to FIG. 15D relate to EPO mRNA, and FIG. 16A to FIG. 16D relate to FFL mRNA.

Capillary electrophoresis experiments performed using the fragment analyzer on T7 versus SP6 in-vitro transcribed RNA before capping and tailing have very similar size and RNA concentrations as shown in FIG. 13A and FIG. 13C respectively; FIG. 14A and FIG. 14C respectively; and FIG. 15A and FIG. 15C respectively; and FIG. 16A and FIG. 16C respectively. Thus, abortive transcripts are not detected in this separation method due to their smaller sizes when the transcripts are not capped and tailed. However, when RNA is capped and tailed, the abortive transcripts become more noticeable due to their size (see also, FIG. 2 to FIG. 4); these abortive transcripts represent a considerable portion of the total RNA in the T7 sample. This is clearly represented in the fainter gel band intensity for the T7-derived transcripts (seen in Section II of each of FIG. 13B, FIG. 14B, FIG. 15B, and FIG. 16B) when compared the stronger gel band intensity for the SP6-derived transcripts (seen in Section II of each of FIG. 13D, FIG. 14D, FIG. 15D, and FIG. 16D respectively). Furthermore, after capping and tailing, T7 transcribed mRNA show a shoulder at the base and shorter height (designating amount of mRNA present) of peak 2 in each FIG. 13B, 14B, 15B, 16B, which correspond primarily to size of the full-length messenger RNA transcript of each indicated gene. On the other hand, the SP6 transcribed mRNA have a narrower base and taller peak, seen in peaks 3 of sections I in FIGS. 13C, 14C, 15C, and 16C which represent full-length mRNA before capping and tailing, as well as in peaks 4 of sections I of FIG. 13D, FIG. 14D, FIG. 15D and FIG. 16D, which represent the full-length mRNA after capping and tailing. Specifically, the lack of a shoulder at the base of peaks 4 in each figure, indicate that there is one molecular species of the same size. The taller peaks (compared to that of T7) indicate that yield of the full-length messenger RNA is higher than that of T7. Additionally, section II of each figure show higher intensity bands in both C and D, compared to A and B respectively, when equal amounts of total mRNA was loaded in each case, indicating greater yield of the full-length transcript with SP6-derived mRNA in each case. Therefore, after capping and tailing the Sp6 generated mRNA bands correspond to the same size, did not reveal any capped and tailed shortmers, and that the full-length mRNA transcript is the primary product.

These data clearly indicate that using a suitable and sensitive assay the short prematurely aborted mRNA transcripts can be detected after capping and tailing, and that SP6 produces a product that is enriched for full-length mRNA at greater proportions than T7 mediated process.

Example 8: SP6-Derived CFTR mRNA Products are Enriched for Full-Length Transcripts Whereas T7-Derived Transcription Products Include Abortive Transcripts In this example, the SP6 and T7 mediated transcription products were characterized using capillary electrophoresis, coupled with UV absorption spectroscopy to visualize the RNA products.

As shown in preceding examples (Examples 4-5) and figures (FIGS. 12-16), abortive transcripts were detectable using a fluorescence-based nucleic acid binding dye. The abortive transcripts were indicated by a broader base (shoulder) around the main peak of the primary transcript of T7 derived mRNA. On the other hand, lack of the shoulder, yielding a narrower and sharper peak was indicative of cleaner mature transcript and lack of the shortmers. However, as shown in the present Example, the prematurely aborted shortmers are more readily visible with UV in place of a fluorescent binding dye. Therefore, the true ratio of abortive transcripts to full-length transcripts is not realized using such a fluorescence-based detection system.

FIG. 17A and FIG. 18B, show hCFTR mRNA produced usingT7 and SP6 polymerase respectively, separated by capillary electrophoresis and detection by UV absorption spectroscopy. The T7-polymerase-based mRNA product (FIG. 17A) shows a large heterogeneous population eluting in the low molecular weight range (100-400 nt) which represents the abortive transcripts (identified as "Pre-aborted sequences"), preceding a taller peak representing the full-length hCFTR mRNA. The transcripts have been capped and tailed using poly-A polymerase. Notably, the SP6-derived mRNA product shows much more homogeneity of full-length product with a drastic minimization of any abortive transcripts. In addition, the SP6-derived product (FIG. 17B) displays a sharper and more intense signal at the molecular weight (transcript length) corresponding to the full-length hCFTR mRNA as compared to the T7-derived product (FIG. 17A), see, for instance the clear resolution of the Internal Standard (IS). This is due to the significant increase in full-length product being present in the SP6-derived product, for an identical amount of total mRNA loaded, as compared to the T7-derived product.

The greater abundance of abortive transcripts in T7-derived sample is consistent with agarose gel visualizations of FIG. 2.

These data clearly shows that SP6 produces a product enriched for full-length mRNA and substantially lack abortive transcripts and also demonstrate the superior applicability of UV spectroscopic detection and analysis of contaminant RNA species in a CE assay, compared to use of fluorescence based nucleotide binding dye.

Example 9: SP6-Derived Transcription Products Produce Increased Quantity of Full-Length Polypeptides Relative to T7-Derived Transcription Products In this example, the translation products of SP6-derived and T7 derived mRNA were compared. Human PAH protein expression was analyzed in HEK293 cells following transfection with T7- or SP6 derived PAH transcripts is shown in FIG. 18. Human EPO protein expression in HEK293 cells following transfection of T7- or SP6 derived EPO transcripts are shown in FIG. 19. CFTR protein expression in HEK293 cells following transfection of T7- or SP6 derived CFTR transcripts are shown in FIG. 20. Same amount of mRNA were used for transfection.

These data show that SP6-derived samples provided a significantly increased quantity of polypeptide products relative to the T7-derived samples.

Example 10: SP6-Derived Transcription Products Produce Polypeptides Having Increased Activity Relative to T7-Derived Polypeptides In this example, SP6-derived transcription products to produce polypeptides having functional activity were compared to the ability of T7-derived transcription products.

Citrulline production, which demonstrates human OTC protein activity in HEK293 cells following transfection of T7- or SP6-derived hOTC transcripts are demonstrated in FIG. 21. Chamber electrophysiological data, which demonstrates current generated in Fisher Rat thyroid cells from CFTR protein expressed following transfection of T7- or SP6-derived transcripts is shown in FIG. 22. These data demonstrate that SP6-derived samples provide polypeptides having significantly increased functional activity relative to the T7-derived samples.

Example 11: Large Scale mRNA Production Using SP6 RNA Polymerase

In this Example, a 10 gram batch of CFTR mRNA was synthesized using SP6- and T7-RNA Polymerase respectively, based on the conditions described in Example 1. As shown in FIG. 23, 2 micrograms of capped and tailed CFTR mRNA taken from the sample prepared using SP6 and T7 were resolved in 1% agarose gel using 10 microliters of Glyoxal denaturing loading dye, at 130V, for 60 minutes. Lane 1 corresponds to SP6-derived product and Lane 2 corresponds to T7-derived product. Lane 2 shows distinct faster migrating band at the lower end of the gel corresponding to the capped and tailed shortmers. In agreement with the observation at smaller scale (Examples 2-8), SP6-derived mRNA produces a clean full-length single band, free of the shortmer band as seen in the T7 derived sample. This demonstrates that SP6-mediated mRNA synthesis may be scaled up without affecting the quality of the mRNA product.

FIG. 24 demonstrates capillary electrophoresis of 10-gram batch preparations of CFTR mRNA using SP6 (FIG. 24A) and T7 (FIG. 24B), both visualized by fluorescent dye mediated detection and analysis. In agreement with the previous observation, the large scale preparation of CFTR using SP6 generated a single peak which is narrower and sharper at the base, lacking the shoulder compared to T7-derived mRNA peak. Presence of the shoulder and the shorter peak in T7-derived mRNA indicates the presence of shortmers and poorer yield of full-length mRNA product. A superimposition of the SP6 and T7 Electropherogram is depicted in FIG. 24C, for direct comparison.

The difference in the quality of mRNA generated by SP6 and T7 polymerase is further demonstrated when the T7-derived and SP-6 derived mRNA were transfected and protein expression levels were determined by western blotting. In this experiment, equal amounts of total mRNA taken from a 10 G batch synthesis produced by T7 IVT or SP6 IVT were transfected under identical conditions to equal number of human embryonic kidney cells (HEK 293 cells). Total protein was extracted from the transfected cells, and equal amounts of the total protein was subjected to western blot analysis using human CFTR specific antibody for detection of the protein expressed by the transcribed mRNA. FIG. 25 demonstrates the comparison of hCFTR protein expression in HEK293 cells, after being transfected with 4 µg of either T7-derived or SP6-derived 10 gram batch synthesized mRNA. Each lane signifies a single transfection set. The first two lanes on the left are proteins extracted from T7-derived mRNA transfected cells, and the remaining 5 lanes are proteins from SP6-derived mRNA transfected samples. Equivalent amounts of total protein were loaded from the cell extracts. The striking difference in the CFTR protein band intensities is due to differences in protein expression efficiency of the transfected mRNA. As can be seen, SP6-derived mRNA resulted in significantly higher protein expression as compared to T7-derived mRNA, which indicates that SP6 based large scale mRNA production resulted in high quality mRNA product and unexpectedly high efficiency in protein expression.

Example 12: Scaling Up Human CFTR mRNA Synthesis Using SP6 Polymerase for IVT 25 gram and 50 gram batches of CFTR mRNA were produced using SP6 polymerase. The mRNA from 25-gram mRNA batch synthesis lots were shown to be expressed successfully when transfected in mammalian cells. Specifically, $1 \times 10^6$ HEK293T cells were transfected with 2 µg of mRNA and the cells were lysed in 0.5 ml 1× Laemmli buffer with 100 mM DTT, and protease inhibitors. The protein extracts were resolved in 6% Tris Glycine gel and blotted with anti-CFTR antibody. FIG. 26 shows a representative western blot analysis. Lanes 1-2 have non-transfected control extracts and lanes 3-6 have CFTR mRNA-transfected cell lysates. Each of the lanes 3-6 show robust expression of CFTR protein. The protein loading control is indicated by the lower band which is uniform in all lanes.

In another experiment, 50-gram batch preparations of CFTR mRNA were analyzed. Capped and tailed purified mRNA aliquots were resolved in a Glyoxal denaturing gel, as shown in FIG. 27. The result demonstrates that SP6 RNA polymerase synthesis can be scaled up to meet commercial production of high quality mRNA substantially free of abortive transcripts.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method for large-scale production of a composition enriched for full-length mRNA molecules comprising synthesizing in vitro mRNA using a recombinant SP6 RNA polymerase having 90% identity to SEQ ID NO: 1, wherein the mRNA is synthesized in about 1 gram to 250 gram quantities in a single batch in a reaction mixture comprising NTPs at a concentration ranging from 1-10 mM each NTP, a DNA template at a concentration ranging from 0.01-0.5 mg/ml, the recombinant SP6 RNA polymerase at a concentration ranging from 0.01-0.1 mg/ml, and a salt or buffering agent, at pH 6.5-8.0, and wherein the reaction is incubated for 60-120 minutes at between 37° C.–42° C.

2. The method of claim 1, wherein at least 80% of the synthesized mRNA molecules are full-length.

3. The method of claim 1, wherein at least 81%, 82%, 83%, 84%, 85%, 86%, 87%, 88%, 89%, 90%, 91%, 92%, 93%, 94%, 95%, 96%, 97%, 98%, 99%, 99.5%, or 99.9% of the synthesized mRNA molecules are full-length.

4. The method of claim 1, wherein the composition comprises less than 20%, 19%, 18%, 17%, 16%, 15%, 14%, 13%, 12%, 11%, 10%, 9%, 8%, 7%, 6%, 5%, 4%, 3%, 2%, 1%, 0.5%, or 0.1% of abortive transcripts.

5. The method of claim 3 or 4, wherein the full-length or abortive transcripts of mRNA are detected by agarose gel electrophoresis.

6. The method of claim 5, wherein the mRNA is denatured by glyoxal before agarose gel electrophoresis ("glyoxal agarose gel electrophoresis").

7. The method of claim 3 or 4, wherein the full-length or abortive transcripts of mRNA are detected by capillary electrophoresis.

8. The method of claim 7, wherein the capillary electrophoresis is coupled with a fluorescence-based detection.

9. The method of claim 7, wherein the capillary electrophoresis is coupled with UV absorption spectroscopy detection.

10. The method of claim 1, wherein the composition is substantially free of abortive transcripts.

11. The method of claim 1, wherein the method further comprises a step of capping and/or tailing the synthesized mRNA.

12. The method of claim 1, wherein the full-length mRNA molecule is at least 100 bases, 200 bases, 300 bases, 400 bases, 500 bases, 600 bases, 700 bases, 800 bases, 900 bases, 1 kb, 1.5 kb, 2 kb, 2.5 kb, 3 kb, 3.5 kb, 4 kb, 4.5 kb, or 5 kb in length.

13. The method of claim 1, wherein the method further comprises a step of purifying synthesized mRNA to remove abortive transcripts.

14. The method of claim 1, wherein the recombinant SP6 RNA polymerase has the amino acid sequence of SEQ ID NO: 1.

15. The method of claim 14, wherein the recombinant SP6 RNA polymerase further comprises a tag.

16. The method of claim 1, wherein the DNA template is sequence optimized.

17. The method of claim 1, wherein the NTPs comprise one or more modified NTPs.

18. The method of claim 1, wherein the mRNA is codon optimized.

* * * * *